US012584173B2

(12) United States Patent
Wang et al.

(10) Patent No.: US 12,584,173 B2
(45) Date of Patent: Mar. 24, 2026

(54) METHODS FOR DISEASE TREATMENT AND DRUG DISCOVERY

(71) Applicant: The Scripps Research Institute, La Jolla, CA (US)

(72) Inventors: Chao Wang, San Diego, CA (US); William E. Balch, San Diego, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 1186 days.

(21) Appl. No.: 17/266,922

(22) PCT Filed: Aug. 9, 2019

(86) PCT No.: PCT/US2019/046028
§ 371 (c)(1),
(2) Date: Feb. 8, 2021

(87) PCT Pub. No.: WO2020/033907
PCT Pub. Date: Feb. 13, 2020

(65) Prior Publication Data
US 2021/0324474 A1 Oct. 21, 2021

Related U.S. Application Data

(60) Provisional application No. 62/716,491, filed on Aug. 9, 2018.

(51) Int. Cl.
| | |
|---|---|
| *C12Q 1/6883* | (2018.01) |
| *G16B 15/20* | (2019.01) |
| *G16B 20/40* | (2019.01) |
| *G16B 40/30* | (2019.01) |
| *G16B 45/00* | (2019.01) |

(52) U.S. Cl.
CPC ........... *C12Q 1/6883* (2013.01); *G16B 15/20* (2019.02); *G16B 20/40* (2019.02); *G16B 40/30* (2019.02); *G16B 45/00* (2019.02); *C12Q 2600/106* (2013.01); *C12Q 2600/136* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 2014/0128447 A1 | 5/2014 | Kapoor et al. | |
| 2015/0241420 A1 | 8/2015 | Johnston et al. | |
| 2016/0312284 A1 | 10/2016 | Grossman et al. | |
| 2017/0309025 A1* | 10/2017 | O'Rourke ............. | G06T 7/0012 |
| 2024/0404621 A1 | 12/2024 | Wang et al. | |

FOREIGN PATENT DOCUMENTS

| | | |
|---|---|---|
| WO | 2020033907 A1 | 2/2020 |
| WO | 2023014982 A2 | 2/2023 |

OTHER PUBLICATIONS

Aurora et al (Genome-wide hepatitis C virus amino acid covariance networks can predict response to antiviral therapy in humans. J Clin Invest. 2009;119(1):225-236) (Year: 2009).*
Watson (Risk Assessment Using the Three Dimensions of Probability (Likelihood), Severity, and Level of Control. Conference Paper, Fourth International Association for the Advancement of Space Safety. (2010)), (Year: 2010).*
Seeburger (2012). (Year: 2012).*
Hopf, T et al, Three-Dimensional Structures of Membrane Proteins from Genomic Sequencing. Cell, Jun. 22, 2012, pp. 1607-1621, 149, Elsevier Inc.
International Search Report and Written Opinion mailed Jan. 13, 2023 in PCT/US2022/039594.
Aurora, R et al., Genome-wide hepatitis C virus amino acid covariance networks can predict response to antiviral therapy in humans, J Clin Invest. Jan. 5, 2009; 119(1): 225-236.
Gianola, D et al., On marker-assisted prediction of genetic value: beyond the ridge, Genetics Jan. 1, 2003 vol. 163 No. 1 347-365.
Han ST, Rab A, Pellicore MJ, et al. Residual function of cystic fibrosis mutants predicts response to small molecule CFTR modulators. JCI Insight. 2018;3(14):e121159. Published Jul. 26, 2018. doi:10.1172/jci.insight.121159.
International Search Report and Written Opinion mailed Dec. 12, 2019 in PCT/US2019/046028.
Pipalia, NH et al., Histone deacetylase inhibitors correct the cholesterol storage defect in most NPC1 mutant cells, Journal of Lipid Research. Feb. 13, 2017, vol. 58, No. 4, pp. 695-708, doi: 10.1194/jlr.M072140.
Subramanian, K et al., Quantitative Analysis of the Proteome Response to the Histone Deacetylase Inhibitor (HDACi) Vorinostat in Niemann-Pick Type C1 disease, Molecular & Cellular Proteomics Nov. 1, 2017, First published on Aug. 31, 2017, 16 (11) 1938-1957; https://doi.org/10.1074/mcp.M116.064949.
Wang, C et al., Managing the Spatial Covariance of Genetic Diversity in Niemann-Pick C1 Through Modulation of the Hsp70 Chaperone System, bioRxiv. Oct. 9, 2018, 10.1101/437764.
Wang, et al., Delivering systems pharmacogenomics towards precision medicine through mathematics. Advanced drug delivery reviews. 65. 10.1016/j.addr.2013.03.002.
Watson Risk Assessment Using the Three Dimensions of Probability (Likelihood), Severity, and Level of Control, Conference Paper, Fourth International Association for the Advancement of Space Safety; May 19, 2010-May 21, 2010; Huntsville, AL; United States, May 19, 2010; https://ntrs.nasa.gov/search.jsp?R=20100024129 2019-10-21T16:09:25+00:00Z.

(Continued)

*Primary Examiner* — Jake M Vu
(74) *Attorney, Agent, or Firm* — Veros Legal Solutions, LLP

(57) ABSTRACT

Drug administration is performed in view of variation spatial profiling (VSP) of patients or potential patients. Spatial-covariance (SCV) relationships relate the position of the disease-associated variant in the polypeptide chain with cell-based models and clinical features of disease. An understanding of SCV relationships for a sparse collection of known fiduciary variants can be used to generate the shape of phenotype landscapes that measure the differential disease behavior for unknown variants, and between distinct cell and tissue environments in patients. The phenotype landscapes can determine which pharmaceutical compounds are administered to potential patients.

10 Claims, 58 Drawing Sheets
(55 of 58 Drawing Sheet(s) Filed in Color)

(56) References Cited

OTHER PUBLICATIONS

Chiles et. al, Geostatistics: Modeling Spatial Uncertainty, Chapter 3 (2012), pp. 147-237.
ISR and Written Opinion mailed Jan. 15, 2023.
Wang, C. and Balch, W; Bridging Genomics to Phenomics at Atomic Resolution through Variation Spatial Profiling, Cell Reports 24(8) (2018), pp. 1-36.

* cited by examiner

| Percentile of prediction confidence in delta phenotype landscape in response to Ivacaftor | Number of CFTR residues | Number of CFTR residues with predicted Ivacaftor response >0.2 of WT ClCon function | Percentage of CFTR residues with predicted Ivacaftor response >0.2 of WT ClCon function |
|---|---|---|---|
| Top 1% | 636 | 338 | 53% |
| Top 5% | 969 | 555 | 57% |
| Top 10% | 1109 | 667 | 60% |
| Top 25 % | 1289 | 813 | 63% |

FIG. 9

METHODS FOR DISEASE TREATMENT AND DRUG DISCOVERY

RELATED APPLICATIONS

This application claims priority to U.S. Provisional Patent Application 62/716,491, filed on Aug. 9, 2018. The entire disclosures of all the related applications set forth in this section are hereby incorporated by reference in their entireties.

STATEMENT OF GOVERNMENT SUPPORT

This invention was made with United States government support under Grant Numbers HL095524 and DK051870 awarded by the National Institutes of Health. The government has certain rights in this invention.

BACKGROUND

The invention relates to optimizing genetic disease diagnoses, pharmaceutical treatment strategies, and drug discovery procedures.

For many diseases or other phenotypes, amino acid sequence variants in one or more proteins have been associated with the condition, and in some cases the relationship between the variant and the disease is at least partially characterized. This information can be used to evaluate and diagnose patients, develop treatment protocols and guide drug discovery. However, given unique complex genetic or environmental background of each individual, the phenotype and/or therapeutic response of variant in the population could be diverse. Moreover, for many variants, the available information is incomplete, and the relationship between the variant and a phenotype is unknown. Disease diagnoses, treatments and drug discovery protocols would benefit from additional techniques to characterize and predict the phenotypic results of variants in the context of unique physiological condition in each individual patient, and particularly for the variants that have little or no existing characterization of their biological effect.

SUMMARY

In one embodiment, a method of testing efficacy and specificity of a drug treatment for Niemann-Pick C1 disease with diverse genotypes in a clinical trial is provided. The method may comprise generating or receiving one or more predicted clinical phenotype landscapes derived from spatial covariance relationships between genotype variants of the NPC1 protein sequence or whole genome sequencing and one or more cellular phenotypes related to cellular cholesterol homeostasis; obtaining NPC1 genotype information for a plurality of subjects; selecting subjects for a clinical trial based at least in part on a comparison of the genotype information for the plurality of subjects and the one or more predicted clinical phenotype landscapes; administering the drug treatment or a placebo to each of the selected subjects gathering drug treatment response information from each of the plurality of selected subjects.

In another embodiment, a method of performing a clinical trial for treating a disease condition with a pharmaceutical, the method may comprise administering the pharmaceutical to a first set of subjects exhibiting the disease condition, administering a placebo to a second set of subjects exhibiting the disease condition, obtaining disease condition response characteristics from each of the first and second sets of subjects, obtaining genotype characteristics from each of the first and second sets of subjects, generating or receiving one or more predicted clinical phenotype landscapes derived from spatial covariance relationships between known genotype variants and one or more known cellular phenotypes, wherein the one or more predicted clinical phenotype landscapes is related to subject response to the pharmaceutical, detecting one or more genotype characteristics that correlate with the clinical phenotype characteristic based at least in part on the disease condition response characteristics, the genotype characteristics, and the one or more predicted clinical phenotype landscapes.

In another embodiment, a method of treating at least one subject with a pharmaceutical compound may comprise generating or receiving a variant-spatial-profiling plot illustrating three-dimensional visualization of a change in estimated severity values for a chemical, biological, or clinical property of a biological molecule in the presence and absence of the pharmaceutical compound, administering the pharmaceutical compound to the at least one subject based at least in part on the variant-spatial-profiling plot.

In another embodiment, a method of estimating clinical, biological and/or chemical properties of protein variants comprises retrieving or computing position values within a subject protein for each of a first plurality of clinically observed variants of the subject protein; retrieving or computing severity values of a first property exhibited by the subject protein when the subject protein contains each of the first plurality of clinically observed variants, and retrieving or computing severity values of a second property different from the first property exhibited by the protein when the protein contains each of the first plurality of clinically observed variants. The method may further comprise defining a two-dimensional coordinate for each of the plurality of clinically observed variants using the position and severity values corresponding to each of the plurality of clinically observed variants, wherein the severity values used in the defining are the severity values for the first property, calculating a distance between each different pair of defined two-dimensional coordinates, and deriving at least one relationship between the variance of severity values of the second property and the distance between two-dimensional coordinates using the calculated distances and the severity values of the second property for each of the clinically observed variants. The method may further comprise estimating severity values of the second property for at least one additional two-dimensional coordinate that is not among the two-dimensional coordinates of the plurality of clinically observed variants, wherein the estimating for the at least one additional two-dimensional coordinate is based at least in part on (1) the distance between the at least one additional two-dimensional coordinate and each of the two-dimensional coordinates corresponding to the plurality of clinically observed variants, and (2) the severity values for the second property at each of the two-dimensional coordinates corresponding to the plurality of clinically observed variants.

In another embodiment, a method of estimating a biological or chemical property of molecules that have different molecular features may comprise receiving or computing position values of a first plurality of molecular features, receiving or computing severity values of a first property exhibited by the molecule when the molecule contains each of the first plurality of molecular features, receiving or computing severity values of a second property exhibited by the molecule when the molecule contains each of the plurality of molecular features, defining a two-dimensional coordinate for each of the plurality of molecular features using the position and severity values corresponding to each of the plurality of molecular features, wherein the severity values used in the defining are the severity values for the first property, calculating a distance between each different pair of defined two dimensional coordinates, deriving at least one relationship between the variance of severity values of the second property and distance using sets of the calculated distances that fall within defined distance ranges, estimating severity values of the second property for an additional plurality of two dimensional coordinates that are not among the two dimensional coordinates of the plurality of molecular features, wherein the estimating for each additional two dimensional coordinate is based at least in part on (1) the distance between each additional two dimensional coordinate and each of the two dimensional coordinates corresponding to the plurality of molecular features, and (2) the severity value for the second property at the two dimensional coordinates corresponding to the plurality of molecular features, and generating a three-dimensional visualization of the estimated severity values for the second property as a function of the two-dimensional coordinates.

In another embodiment, a method of performing a clinical trial for a disease treatment for a disease that is caused at least in part by variants of a protein sequence is provided. The method may comprise generating or receiving one or more predicted clinical phenotype landscapes derived from spatial covariance relationships between genotype variants of the protein sequence and one or more cellular phenotypes, obtaining genotype information for a plurality of subjects, selecting subjects for a clinical trial based at least in part on a comparison of the genotype information for the plurality of subjects and the one or more predicted clinical phenotype landscapes, administering the drug treatment or a placebo to each of the selected subjects, and gathering drug treatment response information from each of the plurality of selected subjects.

Another method is for evaluating clinical trial results to subgroup genotypes for a disease treatment wherein the disease is caused at least in part by variants of a protein sequence. The method may comprise generating or receiving one or more predicted clinical phenotype landscapes derived from spatial covariance relationships between genotype variants of the protein sequence and one or more clinical response features from the patients in the clinical trial, comparing the clinical phenotype landscapes between the drug treated group and placebo group, and defining and predicting the subgroups of genotypes based on spatial covariance for evaluation and disease treatment.

It is understood that various configurations of the subject technology will become apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

Various embodiments are discussed in detail in conjunction with the Figures described below, with an emphasis on highlighting the advantageous features. These embodiments are for illustrative purposes only and any scale that may be illustrated therein does not limit the scope of the technology disclosed. These drawings include the following figures, in which like numerals indicate like parts.

FIG. 4A shows the predicted ClCon values (z-axis) in the absence of Ivacaftor as a phenotype landscape. FIG. 4B shows the predicted ClCon values (z-axis) in the presence of Ivacaftor shown as a phenotype landscape. The ClCon value of WT, F508del and G551D are indicated on the color scale bar. FDA approved variants for treatment with Ivacaftor are highlighted by the square box. Variants recently approved (http://www.cff.org/News/News-Archive/2017/FDA-Approves-Ivacaftor-for-23-Additional-CFTR-Mutations/), but originally rejected by FDA for treatment with Ivacaftor, are highlighted by black triangles illustrating the predictive power of VSP.

FIGS. 7G, 7H, and 7I shpw Var-C maps to illustrate the covariance matrix of both local and long range inter-residue associations in response to low temperature for TrIdx, absolute Band C, and function respectively. The color scale represents the range of covariance/variance value for any pairwise of residues. Top 10 responsive variants are labeled according to their residue position. If F508del is not in the top 10 response list, it is labeled as *F508del. The NBD1 domain in each Var-C map is zoomed in.

FIGS. 8D, 8E, and 8F Var-C maps showing the inter-residue covariance matrix in response to Ivacaftor, Lumacaftor, and Combo respectively. NBD1 region is zoomed in.

FIG. 9 summarizes the predicted changes (delta (A)) of ClCon in response to Ivacaftor for each amino acid residue of CFTR.

DETAILED DESCRIPTION

The following description and examples illustrate some exemplary implementations, embodiments, and arrangements of the disclosed invention in detail. Those of skill in the art will recognize that there are numerous variations and modifications of this invention that are encompassed by its scope. Accordingly, the description of a certain example embodiment should not be deemed to limit the scope of the present invention.

Implementations of the technology described herein are directed generally to optimizing pharmaceutical treatment strategies, drug discovery procedures, and genetic disease diagnoses.

Currently existing variant predictive approaches usually assess the general 'deleteriousness' of genetic variation. They cannot report cell/tissue-specific phenotype and/or differential therapeutic response for variant in each individual patient with unique complex genetic or environmental backgrounds, information that is critical for precision medicine. The reason is that these algorithms are mainly based on sequence conservation by ancestral alignments and/or protein structural snapshots captured by in vitro biophysical techniques (e.g. X-ray crystallography, cryo-EM et. al), which have limited connections to the dynamic physiological condition in each individual patient. To capture the physiological state of the polypeptide in the patient, the inventors reasoned that the variants spread across the entire polypeptide could serve as a marker of altered proteostasis-managed folding intermediates with metastable conformations responsible for function that collectively contribute to the human disease clinical phenotype. In this new way of thinking, the inventors have applied spatial covariance (SCV) values to predict in an unbiased manner the properties of protein variants that are currently incompletely characterized. This method embraces the general concept that sparse SCV relationships between variants can be used to predict unknown values across an entire landscape of variants in the context of human physiological condition.

Figure 1A:
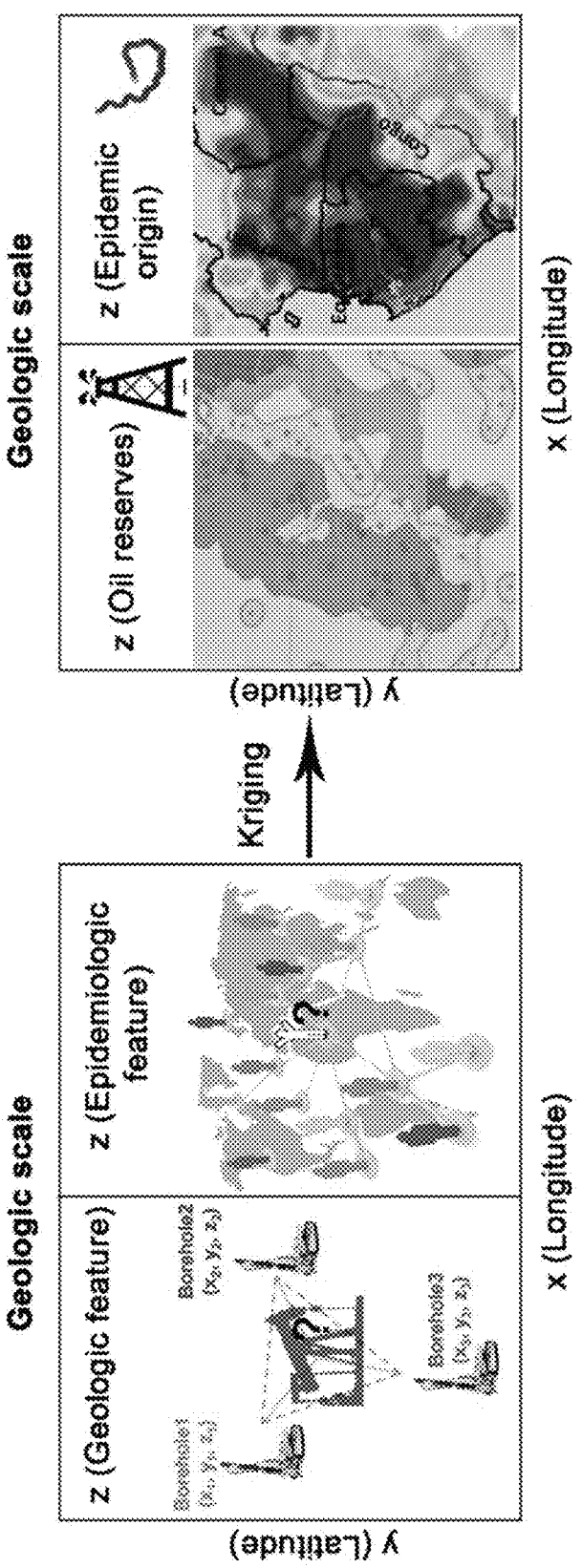
FIG. 1A shows a schematic illustrating Kriging used in oil exploration and epidemiologic studies.

This SCV principle has been used to predict, for example, the amount of oil or an epidemic value, under a particular location based on known borehole oil measurements or epidemiologic feature in population from other locations, respectively. This is known as Kriging illustrated in FIG. 1A. In Kriging (FIG. 1A), the value of the prediction for the location of the oil reserves or epidemic values at unmeasured (unknown) locations in a geological landscape (the output) is calculated by weighted averaging of the input known values based on the spatial covariance (SCV) relationships of a sparse collection of boreholes. In "molecular Kriging" (MK) (FIG. 1B) the value of the prediction for the phenotypic properties for all unmeasured amino acid sequence positions in the polypeptide chain (the output) is calculated from an input of known values for a sparse collection of variants responsible for human disease. MK generates 'phenotype landscapes' that convert the linear sequence information into multidimensional function in the complex environments of human cells, tissues and the human host. This is a generalizable and proprietary principle for predicting any phenotypic relationships assigned to the y- and z-axis coordinates or higher dimensional (4D) landscapes that could include a time coordinate. Building 'phenotype landscapes' does not require 3D structure information, but if the 3D structure is available, the predicted phenotype can be mapped onto structure to explain the static structure in the context of function (FIG. 1B, insert).

In applying this principle to human variation in biology, a plurality of variants is mapped to a position in a multidimensional space. As described in detail below, the coordinates in one implementation may be defined as a position of each variant used for the model, a measured first property of each variant used for the model, and a measured second property for each variant used for the model.

In one implementation, a particular protein may be selected, and the position of a plurality of clinically observed variants within the protein may be determined. The position of a given variant in the protein may be defined as the number of amino acids it is from the beginning to the end of the chain. For example, the N-terminus amino acid is position 1, the next is position 2, and so on until the C-terminus amino acid. It is advantageous to normalize this position value as a fraction of the full-length chain rather than as an integer number of amino acids. When this is done, the C-terminus amino acid may be assigned a value of 1, the N-terminus amino acid may be assigned a value of 1/(total amino acid count), the amino acid adjacent to the N-terminus may be assigned a value of 2/(total amino acid count), and so on. This position value is referred to herein as the variant sequence position (VarSeqP) or alternatively may be called a genotype coordinate. In FIG. 1B, this position is plotted as a distance relationship on the x-axis of a 2-dimensional (2D) coordinate plane. By linearizing position relationships along the polypeptide sequence as a normalized value, all 3-dimensional (3D) features contributed by conformational constraints typical of a folded yet dynamic full-length polypeptide are removed. The conformational state of the protein fold is highly dynamic and challenging to predict in the complex environment of the cell. The methods described herein may be based in all or part on much simpler linear sequence approaches, but the predicted function can capture the 3D structural information (FIG. 1b, insert). This can reveal conservation of function in primary sequence independent of 3D structure.

Figure 1B:
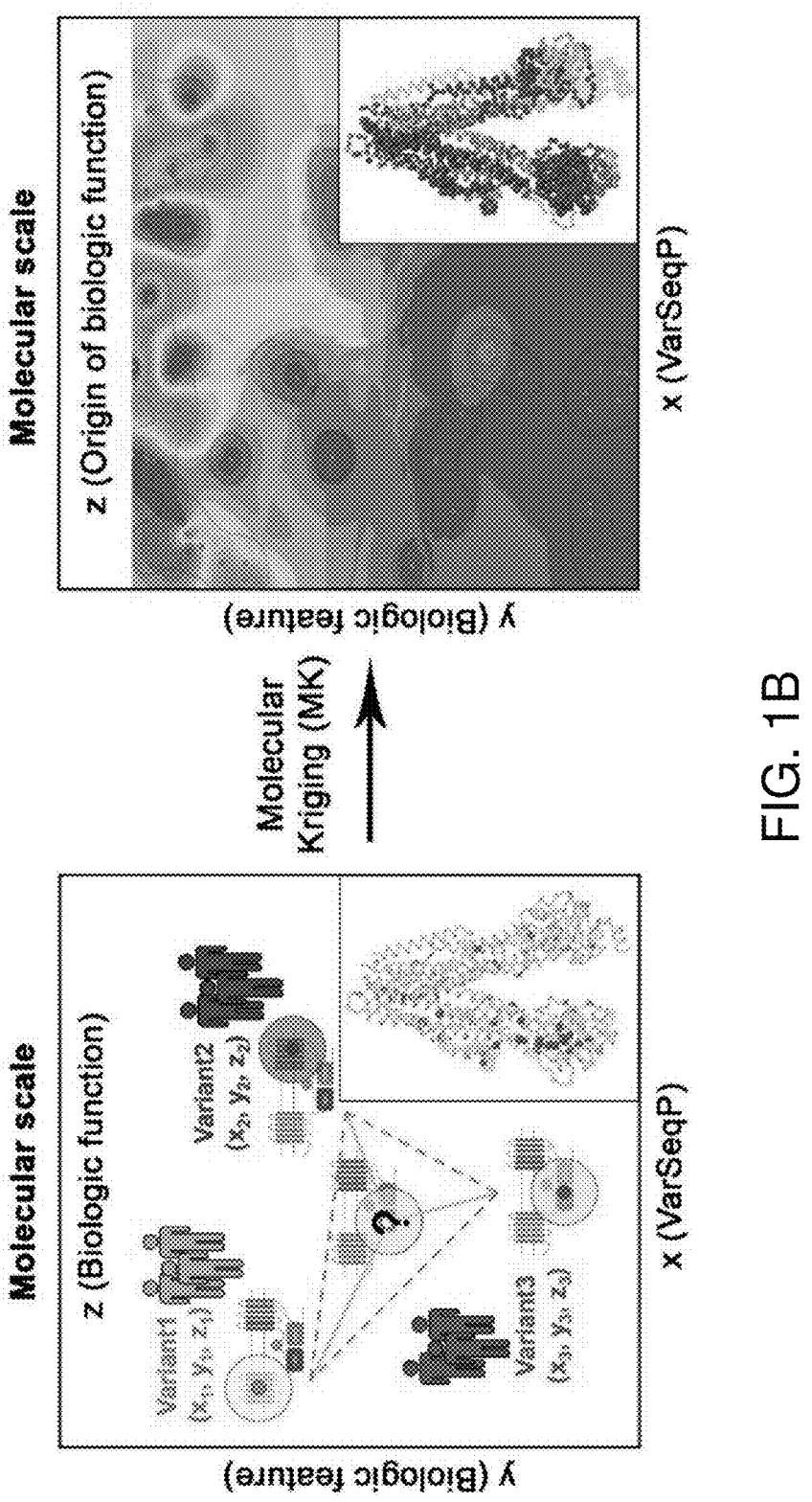
FIG. 1B shows a schematic illustrating molecular Kriging (MK) used for exploring the genotype to phenotype transformation.

To capture the value of information hidden within the linear sequence of the polypeptide chain through its phenotypic responses, that is, the genotype to phenotype transformation, the y-axis provides a second coordinate on the 2D coordinate plane and may be a measure of any selected biological, chemical, or clinical property derived from cell and/or animal models in which a variant is expressed, and/or from clinical measures provided by a patient harboring the variant (FIG. 1B, y-axis). Such a measure is sometimes referred to herein as a "severity value" of a selected chemical, biological, or clinical property for each of the clinically observed variants being used in the model. It can be advantageous to normalize the values along the y-axis as well. In some implementations, the severity value of the wild type without the variants can be set to 1, and the severity value for each variant for the property can be scaled to the wild type value.

In addition, a third dimension (z-axis) coordinate is defined for each of the plurality of variants in a manner similar to the coordinate on the y-axis for a different second measure of any biological, chemical or clinical property derived from cell and/or animal models in which a variant is expressed, and/or from clinical measures provided by a patient harboring the variant (FIG. 1B, z-axis), which may also be normalized with respect to the wild type. The z-axis value may be represented as differing colors overlaid onto the 2D coordinate plane, as is also shown in FIG. 1B. In the following examples, the x-axis is always indicated as genotype coordinate to emphasize the genotype (x-axis) to phenotype (y- and z-axis) transformation. However, it can also be any phenotype for variants to analyze phenotype to genotype or phenotype to phenotype relationships.

Although any chemical, biological, or clinical characteristics can be used for the dimensions beyond the variant position value, in some embodiments, it can be useful to make the first selected chemical, biological, or clinical property be related to a cellular level function that is affected by variants in the protein of interest. Some examples discussed below include chloride conductance and trafficking index. Then, the second selected chemical, biological, or clinical property may advantageously be an organism level clinical property such as disease onset age, drug response characteristics, disease symptom severity, or the like. In this way, hidden connections from molecular level protein properties to cell level function properties, to organism level clinical properties can be revealed in a way that is useful for drug discovery and treatment protocols.

Once the plurality of clinically observed variants are assigned coordinates in the 3D space, a 2D distance between each pair of variant coordinates is determined. This may be, for example, the distance in the x-y coordinate plane for each pair of variants. As used herein, the "distance" between points in a multidimensional space may be the Euclidean distance or may be quantified in a variety of different selected measures of distance between points such as squared Euclidean, Manhattan distance, or others known in the art. A relationship may then be derived between distance in the x-y plane between variant pairs, and the variance of the z-axis property between variant pairs. This may be called a molecular variogram which defines SCV relationships of measured features, e.g., the phenotypic correlative properties of y- and z-function values for each variant in the polypeptide sequence. The variogram represents a measure of how correlated the z-value for any selected (x,y) coordinate is with a z-value measured for a clinically observed variant at a given distance from the selected (x,y) coordinate. Using the variogram, unknown z-axis properties can be inferred in an unbiased manner for locations in the x-y plane different from the locations of the clinically observed variants of the model. This is done for a selected point (x, y) by determining the distances between the point (x,y) and each of the clinically observed variants of the model where a z value related to the second property has been measured. The z-value at the point (x,y) is estimated as a weighted combination of the known z-values for the clinically observed variants of the model, with variants that are closer to the point (x,y) usually, but not necessarily, being weighted higher. What weight to give each of the clinically observed variant z-values when estimating a z-value for the point (x,y) is determined from the molecular variogram. This can generate a phenotypic description through a landscape view, which may be referred to herein as the 'phenotype landscape'. The phenotype landscape may be produced as an output the estimated z-value as a function of position in the (x,y) plane. This allows a visual representation of the biological, chemical, or clinical variable plotted on the z-axis for different (x,y) coordinates. One useful visualization is a visualization in the form of a heatmap that assigns different colors to different z-values and places those colors on (x,y) locations of a two dimensional field, generally, but not necessarily, a flat square field. This provides a visualization of sequence position to z-function relationships for all predicted unmeasured positions spanning the entire polypeptide sequence in the context of their SCV with the measured input values (FIG. 1B, right panel). The highest confident prediction at each amino acid residue can be mapped onto the 3D structure to visualize and interpret the atom structure in the context of function (FIG. 1B, right panel, insert). Other useful visualizations are described further below. The method thus uses a collection of variants found in the human population to generate the shapes of phenotype landscapes that predict the functional impact of any patient genotype on function at the bench and/or in the clinic.

In more mathematical terms, assume we have a phenotypic coordinate 'z' (z-axis value) which is positioned by 'x' which is the amino acid residue position in the polypeptide sequence defined by its genotype and a 'y' phenotypic coordinate (referred to as x- and y-axis values) that describe the phenotype landscape. A molecular variogram is first used to describe how the spatial variance (i.e. the degree of dissimilarity) of 'z' changes according to the separation distance defined by the 'x' and 'y' coordinates which enables the calculation of the spatial covariance (SCV) relationship in the data set.

Suppose the ith (or jth) observation in a data set consists of a value '$z_i$' (or '$z_j$') at coordinates '$x_i$' (or '$x_j$') and '$y_i$' (or '$y_j$'). The distance 'h' between the ith and jth observation may be calculated by:

$$h_{(i,j)} = \sqrt{(x_i - x_j)^2 + (y_i - y_j)^2} \qquad (1)$$

and the $\gamma(h)$-variance for a given distance (h) may be defined by $$\gamma(h) = \tfrac{1}{2}(z_i - z_j)^2 \qquad (2)$$

$\gamma(h)$-variance is the semivariance of 'z' value between the two observations, which is also the whole variance of 'z' value for one observation at the given separation distance 'h'. Here, we refer $\gamma(h)$-variance as spatial variance as indicated in the y-axis of molecular variogram. By equation (1) and (2), the distance (h) and $\gamma(h)$-variance for all the data pairs are generated. Then, the average values of $\gamma(h)$-variance for different distance intervals are calculated to plot $\gamma(h)$ versus h used in the molecular variogram. Linear, spherical, exponential or Gaussian models can be used to fit the data in the molecular variogram, and the final model may be determined by the residual sums of squares of the fitting and the leave-one-out cross-validation result of the model. The distance where the model first flattens out may be referred to as the range. Sample locations separated by distances closer than the range are spatially correlated, whereas locations farther apart than the range are not. The spatial covariance (SCV) at the distance (h) is calculated by $C(h) = C(0) - \gamma(h)$, where $C(0)$ is the covariance at zero distance representing the global variance of the data points under consideration (i.e., the plateau of the molecular variogram).

According to the molecular variogram, values of the z-property when there is a close distance in the x-y plane are usually correlated and have more weight for prediction. To solve the optimum and unbiased weights of SCV relationships, the process aims to minimize the variance associated with the prediction of the unknown value at location 'u', which is generated according to the expression:

$$\sigma_u^2 = E[(z_u^* - z_u)^2] = \Sigma_{i=1}^n \Sigma_{j=1}^n \omega_i \omega_j C_{i,j} - 2\Sigma_{i=1}^n \omega_i C_{i,u} + C_{u,u} = \text{minimum} \qquad (3)$$

where '$z_u^*$' is the prediction value while '$z_u$' is the true but unknown value, '$C_{i,j}$' and '$C_{i,u}$' are SCV between data points 'i' and 'j', and data points 'i' and 'u' respectively, and '$C_{u,u}$' is the SCV within location 'u'. $\omega_i$ is the weight for data point 'i'. The SCV is obtained from the above molecular variogram analysis. The above formula squares the quantity $(z_u^* - z_u)$, but the absolute value, the square root of the absolute value, or other positive functions of $(z_u^* - z_u)$ may alternatively be used.

To ensure an unbiased result, the sum of weight is set as one.

$$\Sigma_{i=1}{}^{n}\omega_i=1 \qquad (4)$$

Equations (3) and (4) not only solve the set of weights associated with input observations, but also provide the minimized 'molecular variance' at location 'u' which can be expressed as $$\sigma_u{}^2=C_{u,u}-(\Sigma_{i=1}{}^{n}\omega_i C_{i,u}+\mu) \qquad (5)$$

where '$C_{u,u}$' is the SCV within location 'u', $\omega_i$ is the weight for data point 'i', '$C_{i,u}$' are SCV between data points 'i' and 'u'. '$\mu$' is the Lagrange Parameter that is used to convert the constrained minimization problem in equation (3) into an unconstrained one.

The resulting minimized variance (or standard deviation of prediction) provides a weighted SCV score that represents the confidence for using the SCV relationships both within the input data points and in relation to the unknown locations. The confidence level is related to the distance range in the molecular variogram. The shorter distance between unknown point to the input data points, the higher confidence for using the SCV relationships for prediction.

The minimization of variance (equation 3) with the constraint that the sum of the weights is one (equation 4) can now be written in matrix form as:

$$C \quad \cdot \quad W \quad = \quad D \qquad (5)$$

$$\begin{bmatrix} C_{1,1} & \cdots & C_{1,n} & 1 \\ \vdots & \ddots & \vdots & \vdots \\ C_{n,1} & \cdots & C_{n,n} & 1 \\ 1 & \cdots & 1 & 0 \end{bmatrix} \cdot \begin{bmatrix} \omega_1 \\ \vdots \\ \omega_n \\ \mu \end{bmatrix} = \begin{bmatrix} C_{1,u} \\ \vdots \\ C_{n,u} \\ 1 \end{bmatrix}$$

where 'C' is the covariance matrix of the known data points. 'W' is the set of weights assigned to the known data points for prediction. '$\mu$' is the Lagrange multiplier to convert a constrained minimization problem into an unconstrained one. 'D' is the covariance matrix between known data points to the unknown data points. Since 'W' is the value we want to solve to generate the phenotype landscape*, this equation can be also written as $$W = \underbrace{C^{-1}}_{Clustering} \cdot \underbrace{D}_{Distance} \qquad (6)$$

where '$C^{-1}$' is the inverse form of the 'C' matrix.

An intuitive explanation of the matrix notation is that it contains two of the important aspects for predicting unknown values of each variant relationship to function—the clustering (i.e. grouped sequence with similar function properties) and distance constraints. '$C^{-1}$' represents the clustering information of the known data points while 'D' represents a statistical distance between known data points to the unknown data point.

With the solved weights 'W', an estimation for all unknown values to generate a complete phenotype landscape by the equation $$z_u{}^*=\Sigma_{i=1}{}^{n}\omega_i z_i{}^* \qquad (7)$$

where $z_u{}^*$ is the prediction value for the unknown data point 'u', '$\omega_i$' is the weight for the known data point and '$z_i$' is the measured phenotypic value for data point 'i'.

Multiple validation methods can be used to assess the performance of the above estimation methods, for example a leave-one-out cross-validation and validation by an external data set. In the leave-one-out cross validation, all data are initially used to build the molecular variogram and models. Then, each data point is removed one at a time and the rest of the data points are used to predict the missing value. The prediction is repeated for all data points and the prediction results are compared to the measured value to generate the Pearson's r-value and its associated p-value (ANOVA test). For external data set validation, results from separate studies that were not used for training can be utilized. Estimated output z values are generated by feeding the model with x- and y-values, and compared to the observed values by Pearson's correlation analysis and p-value calculation (ANOVA test).

To be useful to physicians, researchers, drug developers, and the like, it is advantageous to generate visualizations of the input and output of the above methods. These visualizations can be important to using the data to make treatment decisions and design clinical trials for example. Some of the useful visualizations are shown and described with respect to the examples provided below. These visualizations are significant for data analysis because the estimate z-value is dependent on two input parameters x, and y. More than 2 dimensions should therefore be visualized. Three general options are illustrated herein. A first may be described as planar visualizations, where the third dimension is indicated by regional properties of portions of a rectangular plane, where different regions may be delineated by different color, shading (e.g. gray scale or fill pattern), or contour line delineation. A second may be described as perspective visualizations, where the third dimension is indicated by generating a perspective view of a 2-dimensional surface in a 3-dimensional environment. A third would be combined planar and perspective visualizations. For example, a plurality of planar surfaces may be illustrated in a perspective view. Alternatively, a perspective surface could have colored regions or regions defined by contour lines on the surface. More than three dimensions can be visualized with these types of plots by combining two or more of the contours, colors, planar, and perspective views.

As one example, useful visualizations include one or both of contour and heatmap plots of the output. At least two pieces of information are available from the methods set forth above. One is the estimated z-values at different (x,y) coordinates, and the other is a confidence level in the accuracy of the estimate (e.g. standard deviation of the prediction). In some implementations, this confidence level of the z-estimate at given point (x,y) may be numerically expressed as the percentage over all the estimated locations. With this measure, a lower percentage means a higher confidence in the accuracy of the predicted z-value at that point. Other confidence level measures may also be utilized such as the conventional confidence interval.

Figure 3A:
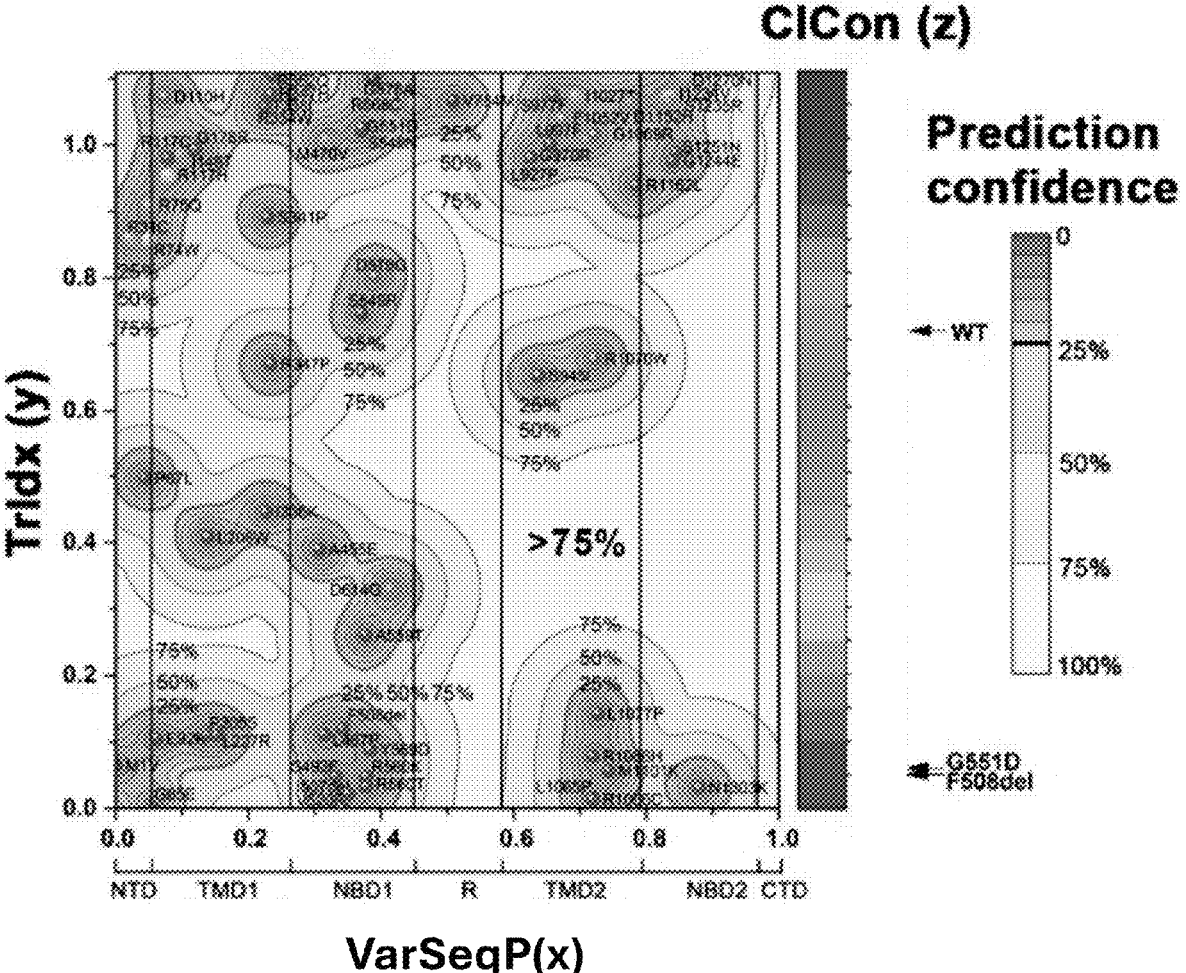
FIG. 3A shows mapping CFTR phenotype landscape (variation in the population defined by human genome sequencing assigned the x-axis) to any phenotypic relationship assigned to the y- and z-axis coordinates or higher dimensional (4D) landscapes that may include a time coordinate. The confidence in SCV relationships for estimation for unknown locations in the context of input known locations are plotted as a gray gradient delineated numerically by contour lines. Sequence modules falling within top 25% quartile confidence interval are indicated by the bold line.
Figure 3B:
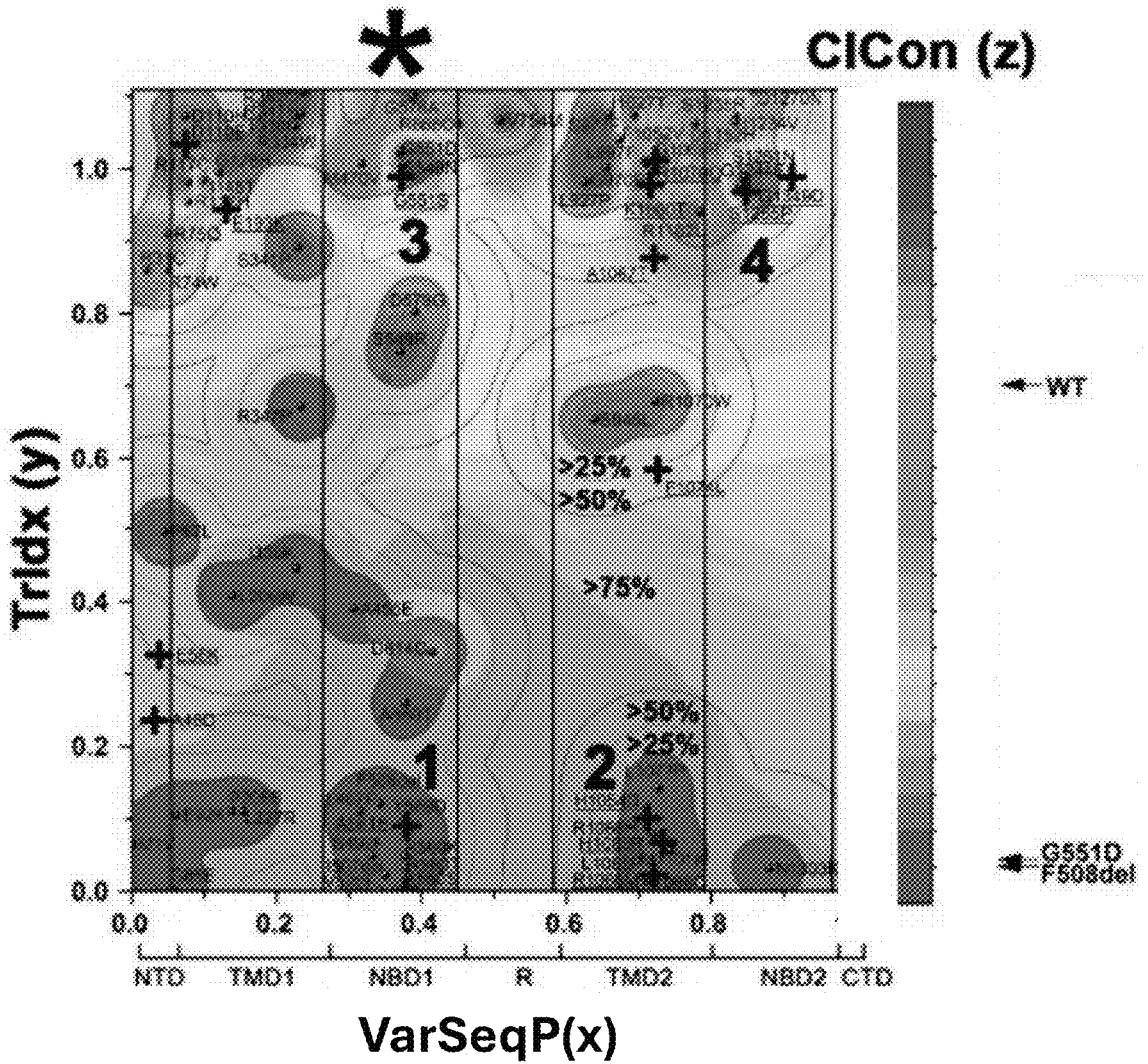
FIG. 3B shows the MK predicted output values of ClCon across the entire VarSeqP is shown as a heatmap overlaid with the contour intervals shown in FIG. 3A. Contour intervals extending beyond the top 25% quartile confidence interval are shown in 50% transparency. Variants from a separate study used for validation are indicated by the plus symbols and underlined labels.
Figure 3C:
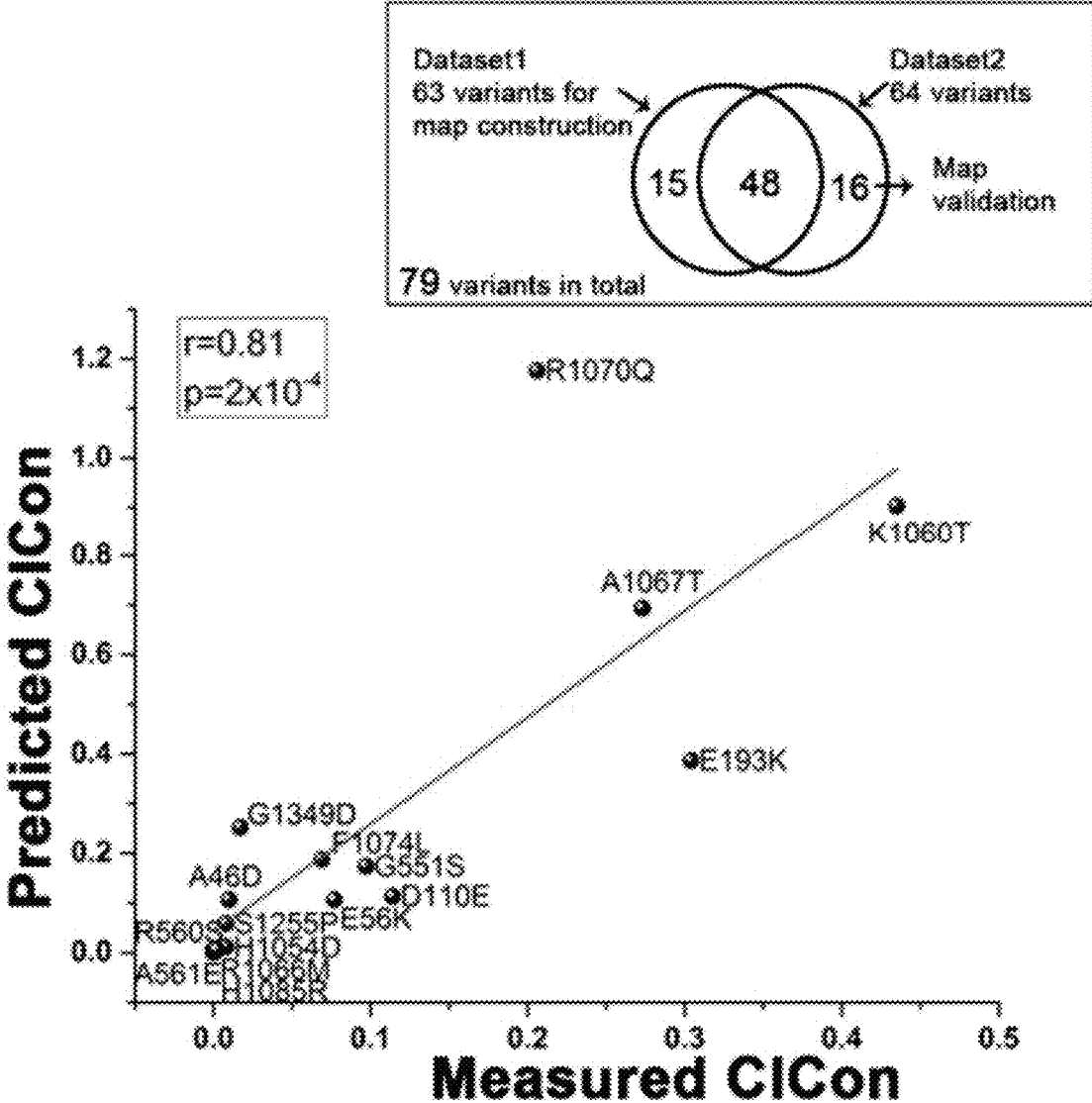
FIG. 3C is a plot of measured and predicted values, with Pearson's correlation coefficient (r-value) between measured and predicted values, and the p-value (ANOVA test) with null hypothesis with the coefficient equal to zero are indicated. (Inset) Overlap of variants from two separate studies shown as a Venn diagram used for training and validation.
Figure 3D:
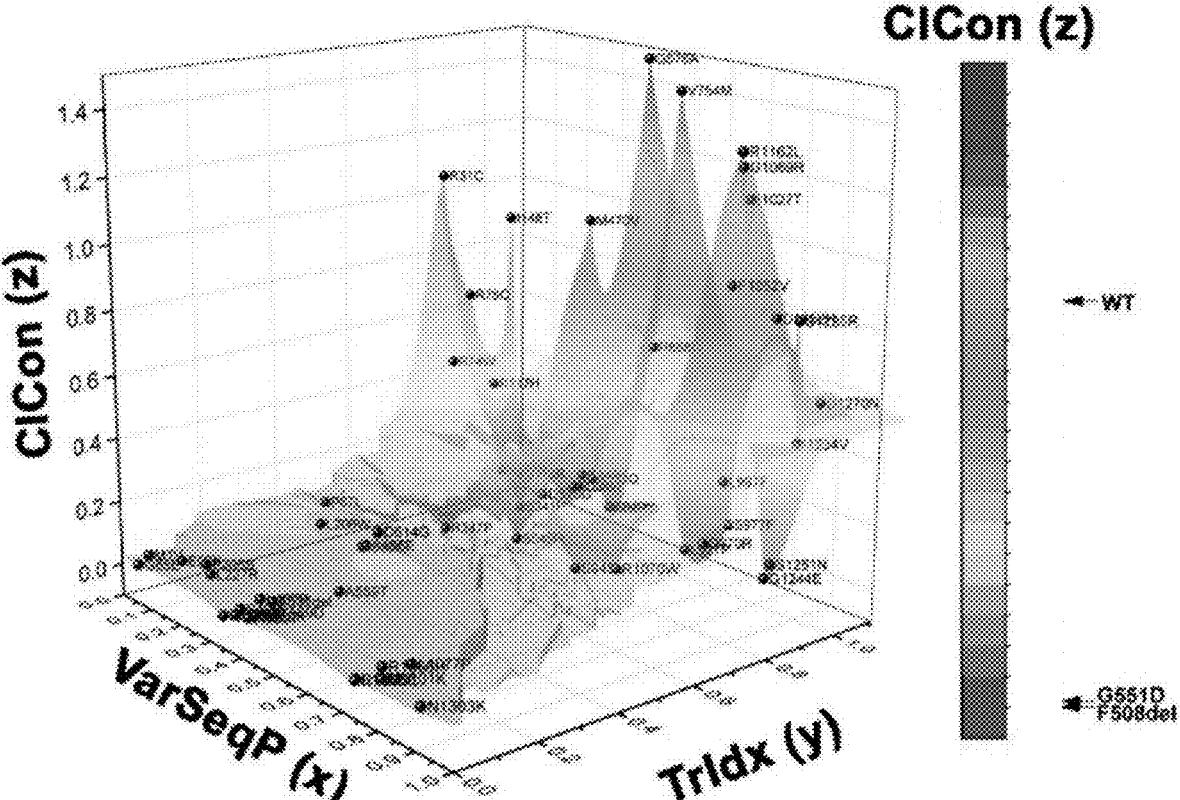
FIG. 3D is a three-dimensional projection of the data of FIG. 3B.

Either the estimates or the confidence levels can be visualized with a contour or heatmap representation or a combination of the two. For example, in FIG. 3A, the confidence levels are indicated both as contours and shades of gray, defining confidence regions on the plot of 0-25%, 25-50%, 50-75%, and >75%. In FIG. 3B, the confidence intervals of FIG. 3A are provided by contour lines, and different z-value ranges are indicated with different colors on the plot, which may be referred to as a "heat map." In FIG. 3D, a perspective landscape view is shown, where the estimated z-values are presented as a perspective view of a 2D surface. As shown in FIG. 3D, heat map colors can be placed on the surface, supplementing the z-value indication that is provided by height of the surface in the z direction. Confidence intervals could also be illustrated either additionally or alternatively with colors, shades of gray, or contour lines on the 2-dimensional surface that is presented in perspective view.

Figure 4A:
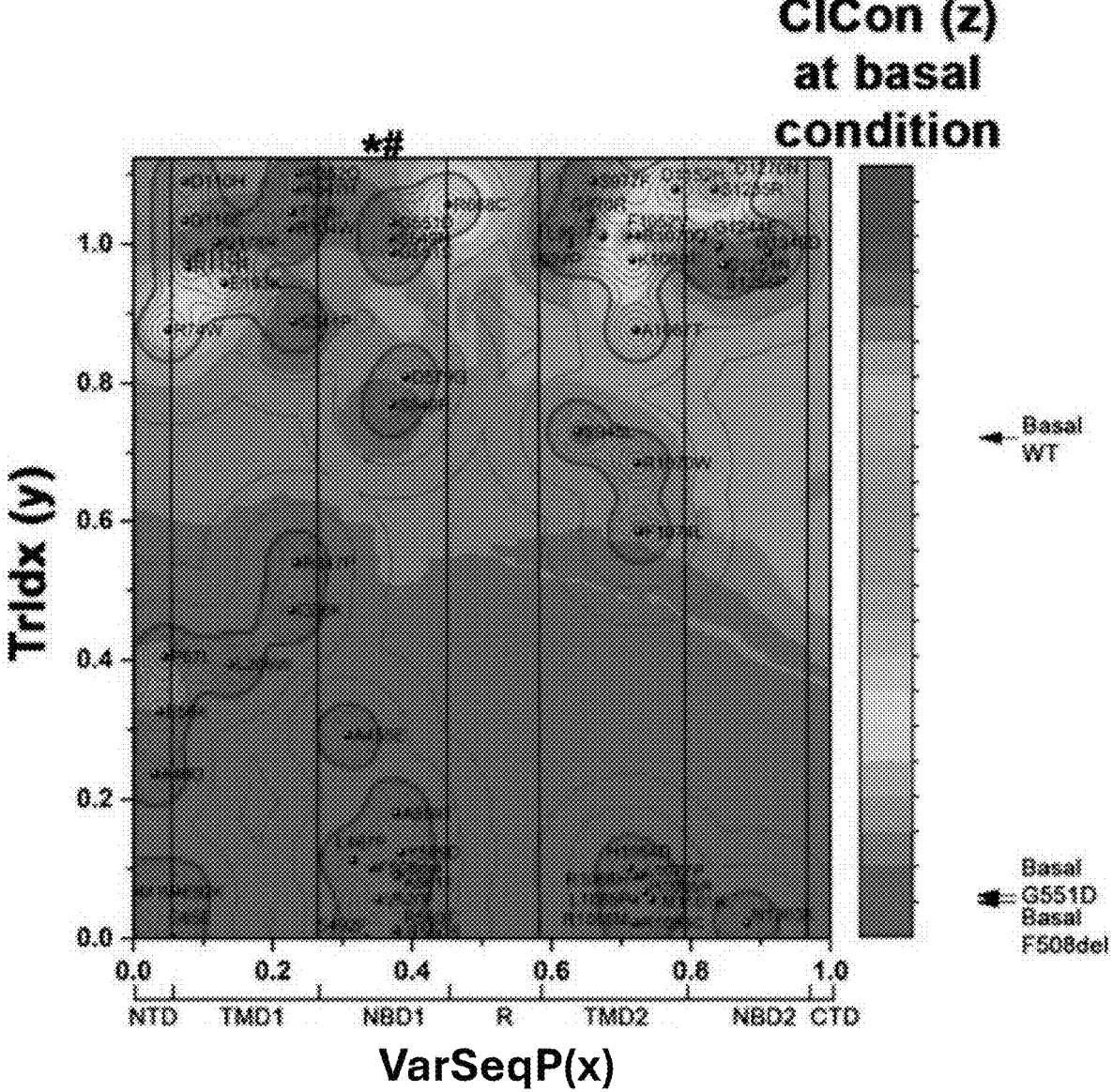
FIGS. 4A and 4B show Ivacaftor responsive phenotype landscapes.
Figure 4B:
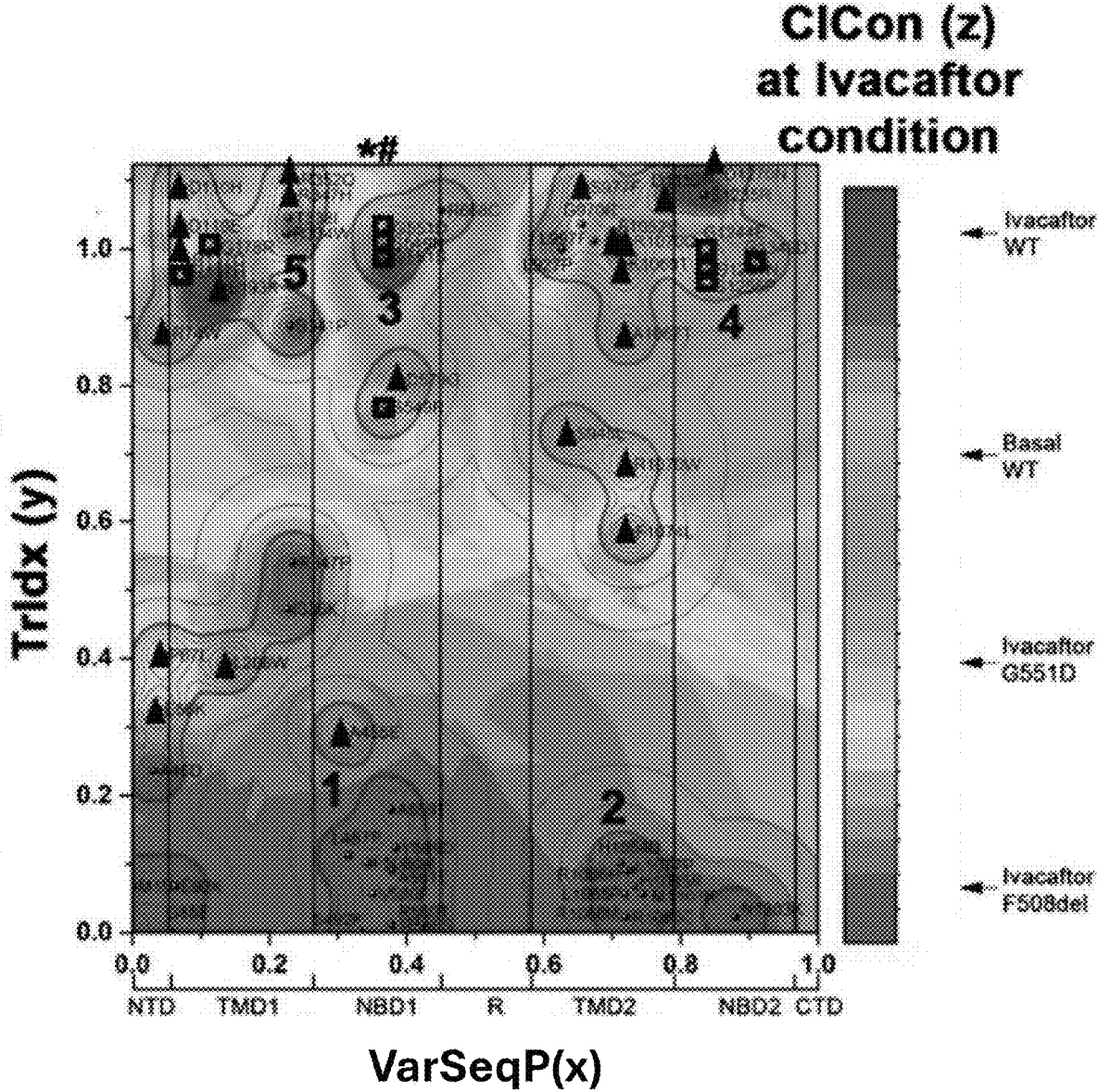

All the estimated y- and z-function values for each amino acid residue can be plotted as 'slice' view as FIG. 4B. This visualization shows the full range of function for the variations on each residue. Since y-axis may be a measure of any selected biological, chemical, or clinical property derived from individual patient, the corresponding estimation of z-function reflects the physiological condition of the patient. For example, the patients with the same genotype F508del have been shown to respond differently to therapeutic treatment, FIG. 4B can estimate the drug response (z-function) depending on the y-function specific to individual patient, thus providing a useful tool for precision medicine.

To generate a more intuitive view of the phenotype landscape from 3D structure perspective, the estimated function can be mapped to a 3D structure snapshot if it is available. For example, in FIG. 3G and FIG. 4C, the estimated function with highest confidence is mapped onto the structure to illustrate the structural mechanisms for function or therapeutic response.

Figure 5A:
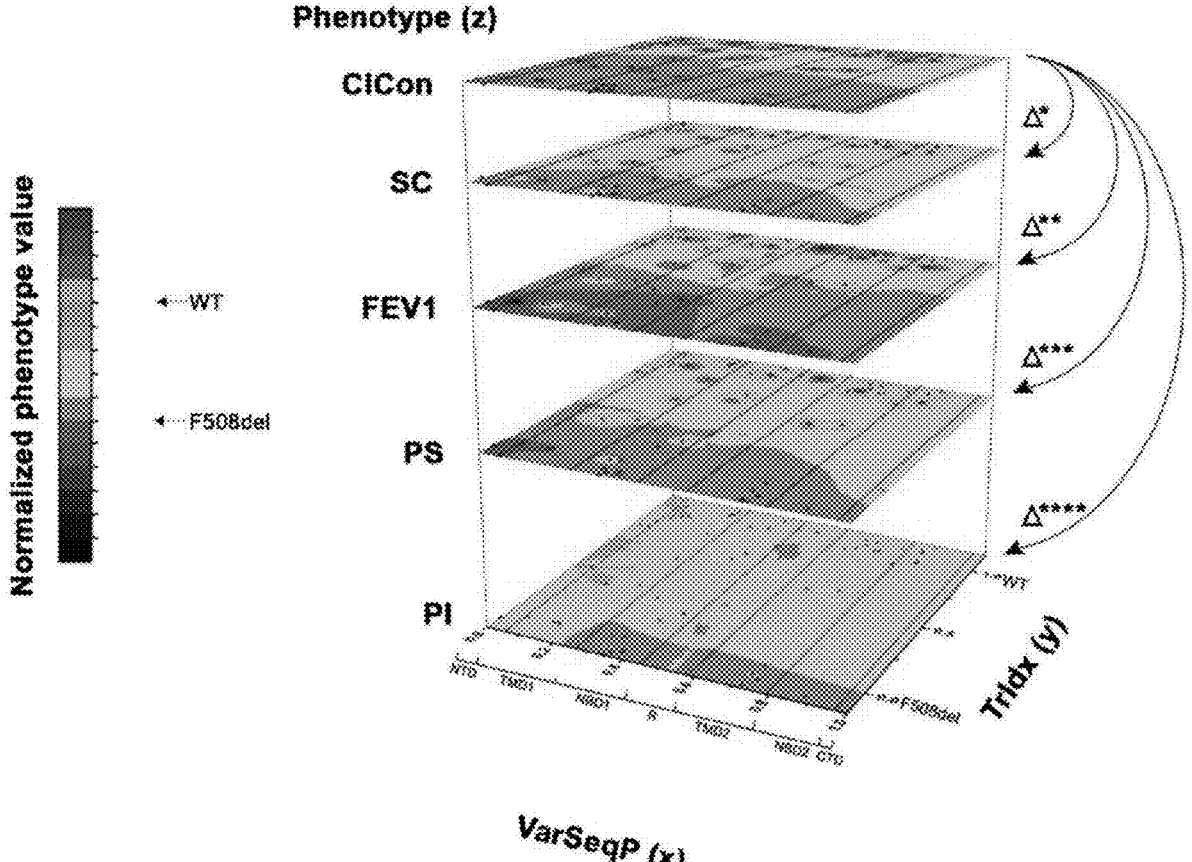
FIG. 5A shows the application of VSP to clinical phenotypes. (a) (Upper panel) Phenotype landscapes relating sequence position of variant (x-axis) and its cell-based TrIdx (y-axis) to the indicated features (z-axis): cell-based chloride conductance (ClCon); clinical sweat chloride (SC); clinical forced expiratory volume 1 (FEV1); clinical *Pseudomonas* (PS); clinical pancreatic insufficiency (PI). Color scale (z-axis) is normalized to the WT assigned a value of 1 and F508del assigned a value of 0.
Figure 5B:
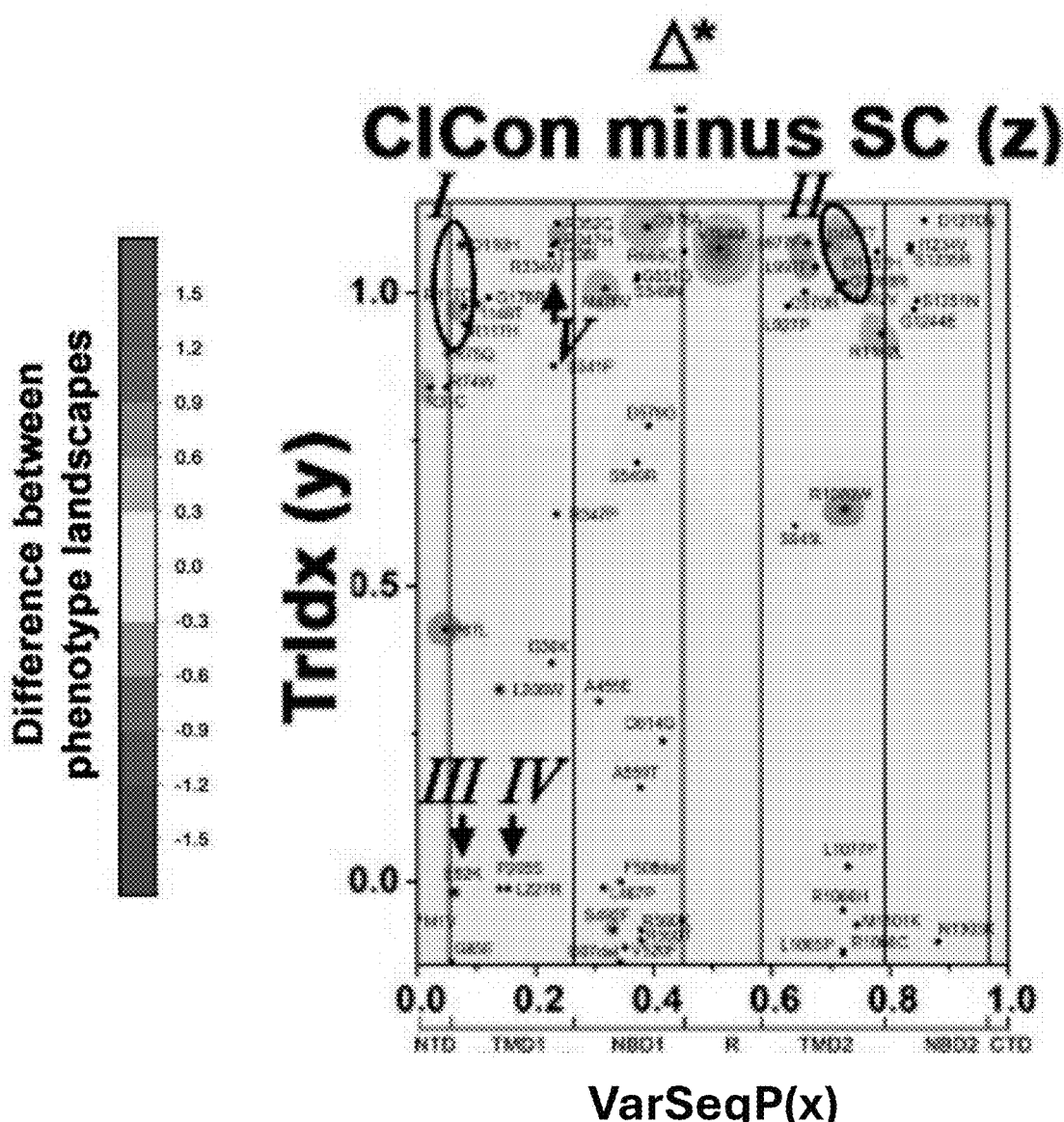
FIG. 5B is a Δ landscape comparing the cell-based TrIdx (y)-ClCon (z) phenotype landscape to the SC clinical feature phenotype landscape. Normalized values that are higher in the cell-based model than found in the clinical feature are shown in red; normalized values that are lower in the cell-based model than found in the clinical feature are shown in blue. Circles I and II show SCV clusters whose cell-based values consistently differ from all clinical measures. Arrow regions III-V show SCV clusters that are variable among different clinical phenotypes.
Figure 5C:
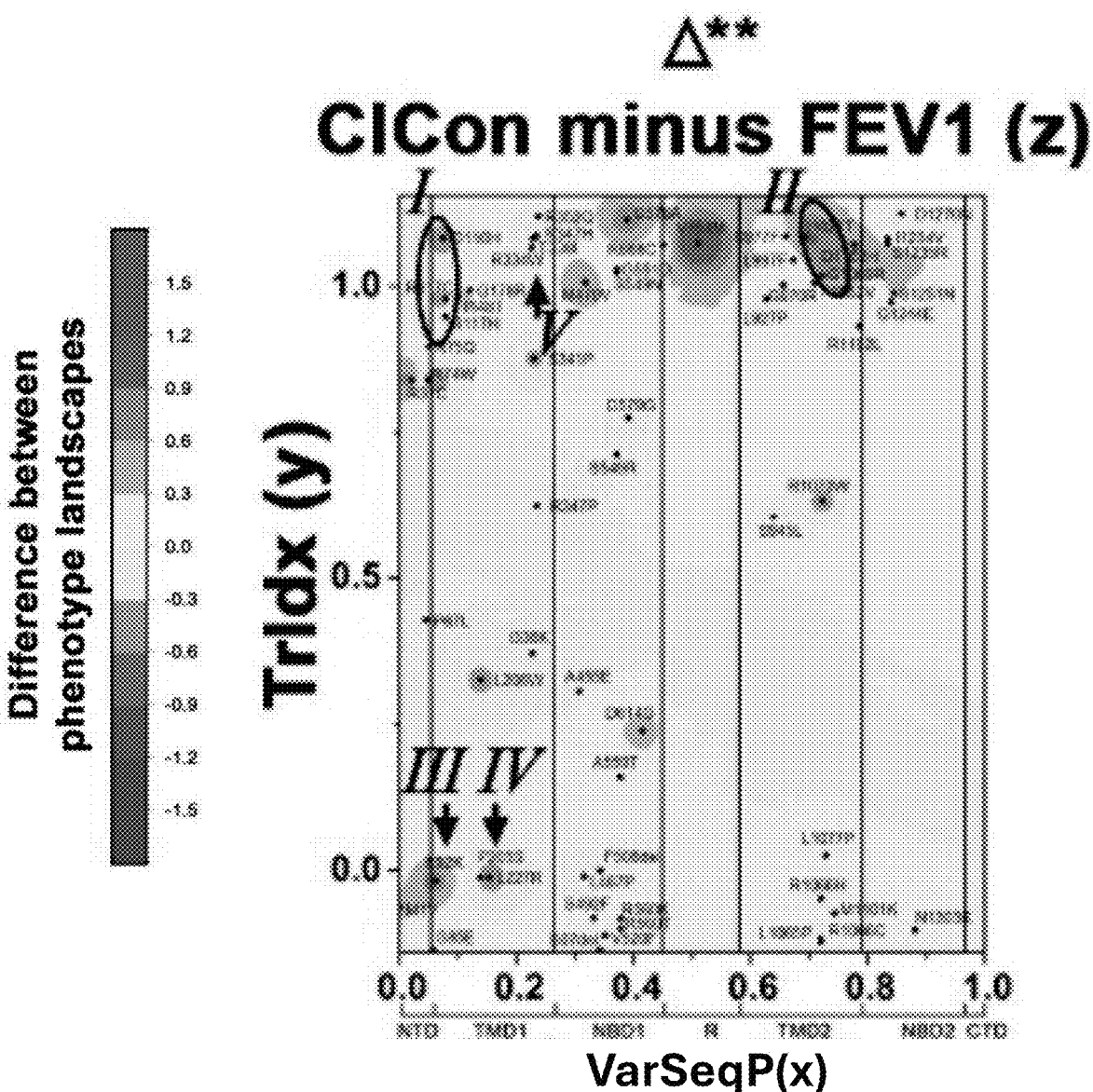
FIG. 5C is a Δ landscape comparing the cell-based TrIdx (y)-ClCon (z) phenotype landscape to the FEV1 clinical feature phenotype landscape. Normalized values that are higher in the cell-based model than found in the clinical feature are shown in red; normalized values that are lower in the cell-based mode than found in the clinical feature are shown in blue. Circles=1\*ROMANI and =2\*ROMANIII show SCV clusters whose cell-based values consistently differ from all clinical measures. Arrow regions=3\*ROMANIII–=5\* ROMANV show SCV clusters that are variable among different clinical phenotypes.
Figure 5D:
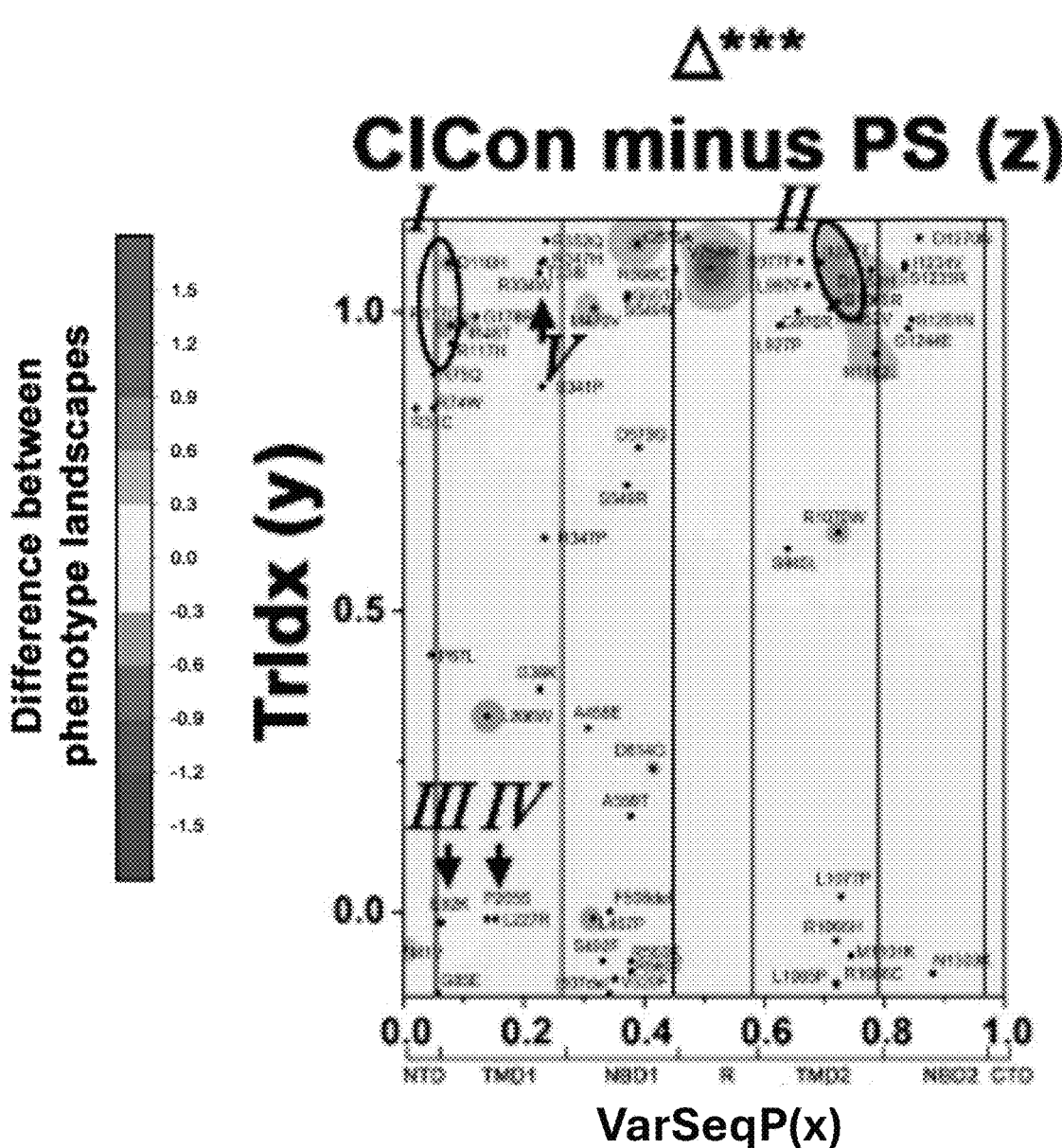
FIG. 5D is a Δ landscape comparing the cell-based TrIdx (y)-ClCon (z) phenotype landscape to the PS clinical feature phenotype landscape. Normalized values that are higher in the cell-based model than found in the clinical feature are shown in red; normalized values that are lower in the cell-based mode than found in the clinical feature are shown in blue. Circles=1\*ROMANI and =2\*ROMANIII show SCV clusters whose cell-based values consistently differ from all clinical measures. Arrow regions=3\* ROMANIII–=5\* ROMANV show SCV clusters that are variable among different clinical phenotypes.
Figure 5E:
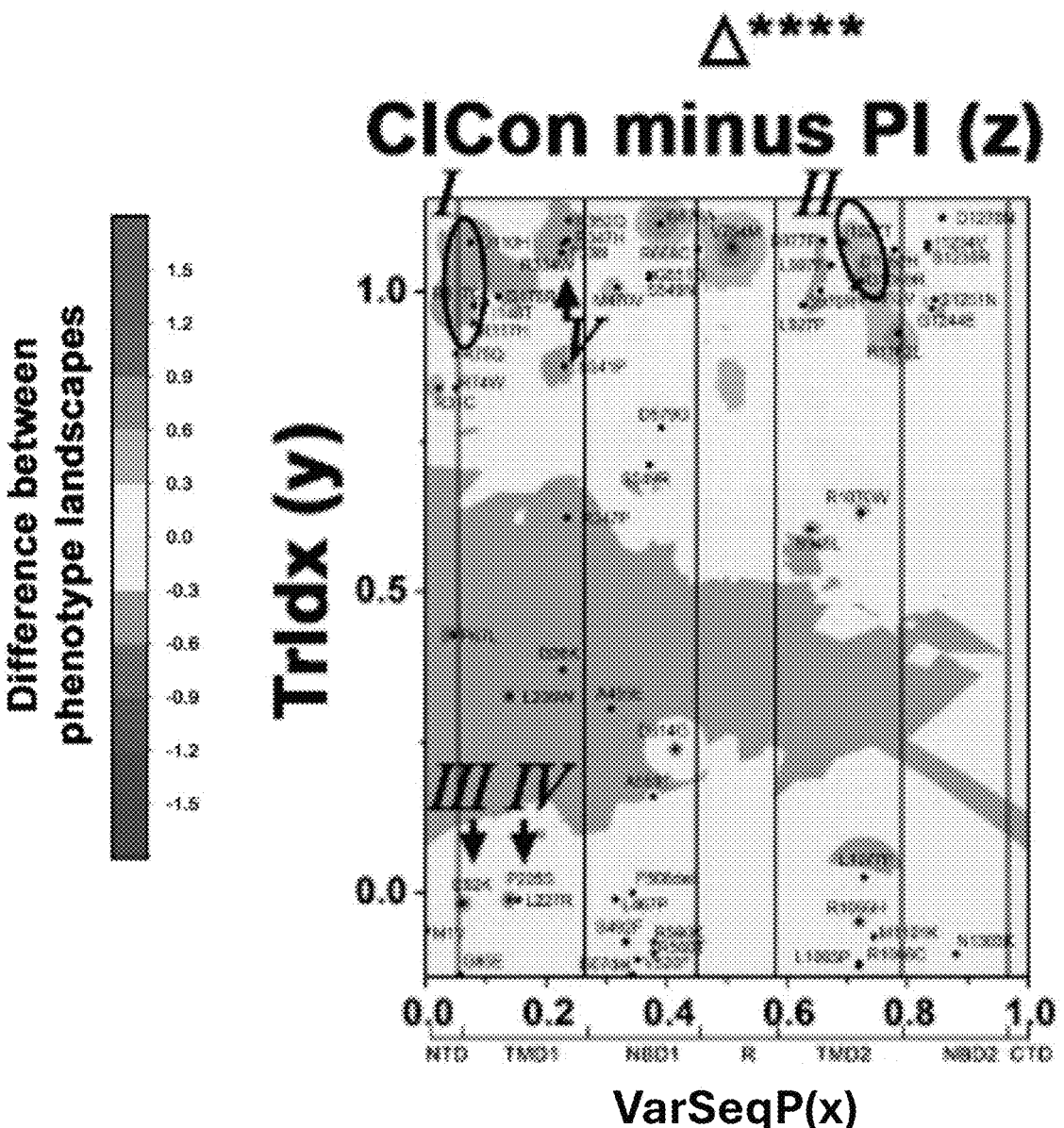
FIG. 5E is a Δ landscape comparing the cell-based TrIdx (y)-ClCon (z) phenotype landscape to the PI clinical feature phenotype landscape. Normalized values that are higher in the cell-based model than found in the clinical feature are shown in red; normalized values that are lower in the cell-based mode than found in the clinical feature are shown in blue. Circles=1\*ROMANI and =2\*ROMANIII show SCV clusters whose cell-based values consistently differ from all clinical measures. Arrow regions=3\* ROMANIII–=5\* ROMANV show SCV clusters that are variable among different clinical phenotypes.
Figure 5F:
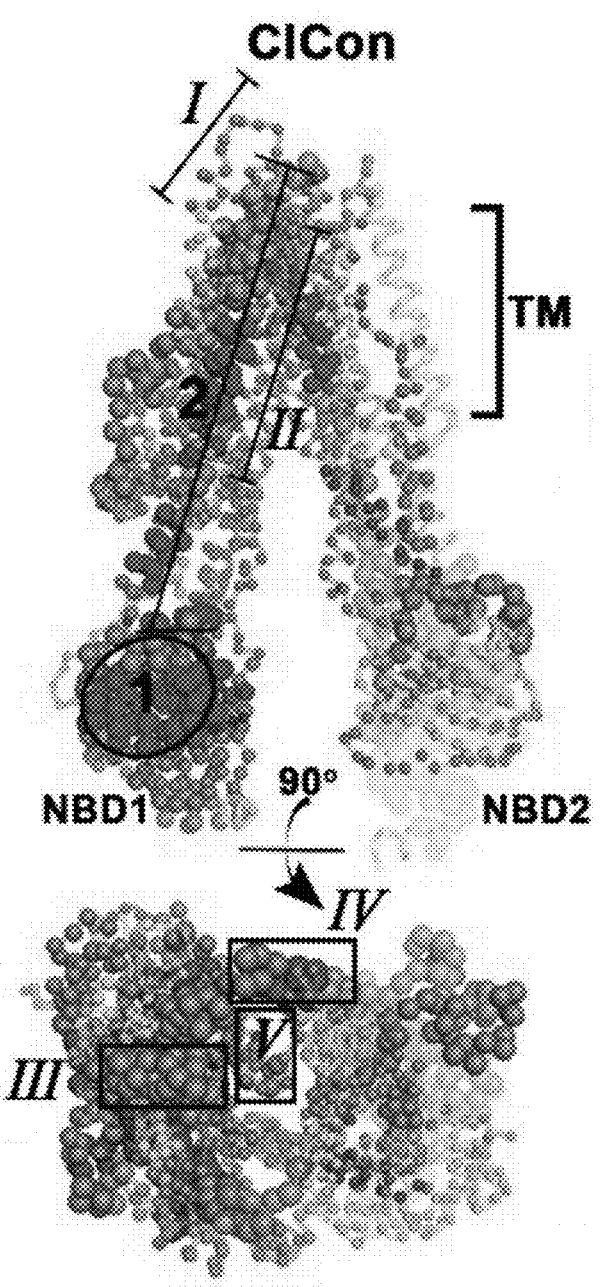
FIG. 5F illustrates a clinical functional structure generated using the ClCon phenotype landscapes of FIG. 5A. The highest confidence prediction of the phenotype generated by MK is assigned to each residue. The alpha carbon of each residue is shown as a ball with size representing TrIdx, color representing the predicted phenotype, and transparency representing prediction confidence. The locations of tissue invariant SCV predictions in NBD1 (circle 1, large red balls) and TMD2 (bar 2, large red balls) are shown. Clusters I and II in the Δ phenotype landscapes of FIGS. 5B, 5C, 5D, and 5E are indicated by bars. Clusters III-V shown in the Δ phenotype landscapes of FIGS. 5B, 5C, 5D, and 5E are indicated by boxes.
Figure 5G:
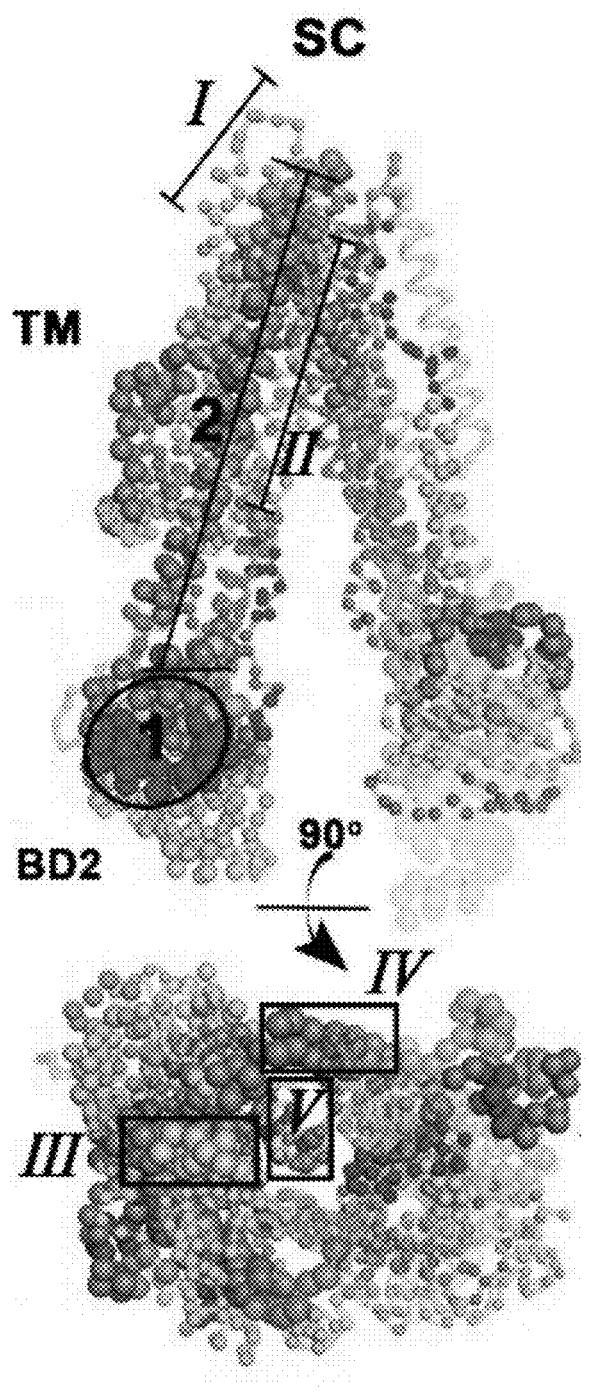
FIG. 5G illustrates a clinical functional structure generated using the SC phenotype landscape of FIG. 5A. The highest confidence prediction of the phenotype generated by MK is assigned to each residue. The alpha carbon of each residue is shown as a ball with siz representing TrIdx, color representing the predicted phenotype, and transparency representing prediction confidence. The locations of tissue invariant SCV predictions in NBD1 (circle 1, large red balls) and TMD2 (bar 2, large red balls) are shown. Clusters=1\*ROMANI and =\*ROMANII in the Δ phenotype landscapes of FIGS. 5B, 5C, 5D, and 5E are indicated by bars. Clusters=\*ROMANIII–=5\* ROMANV shown in the Δ phenotype landscapes of FIGS. 5B, 5C, 5D, and 5E are indicated by boxes.
Figure 5H:
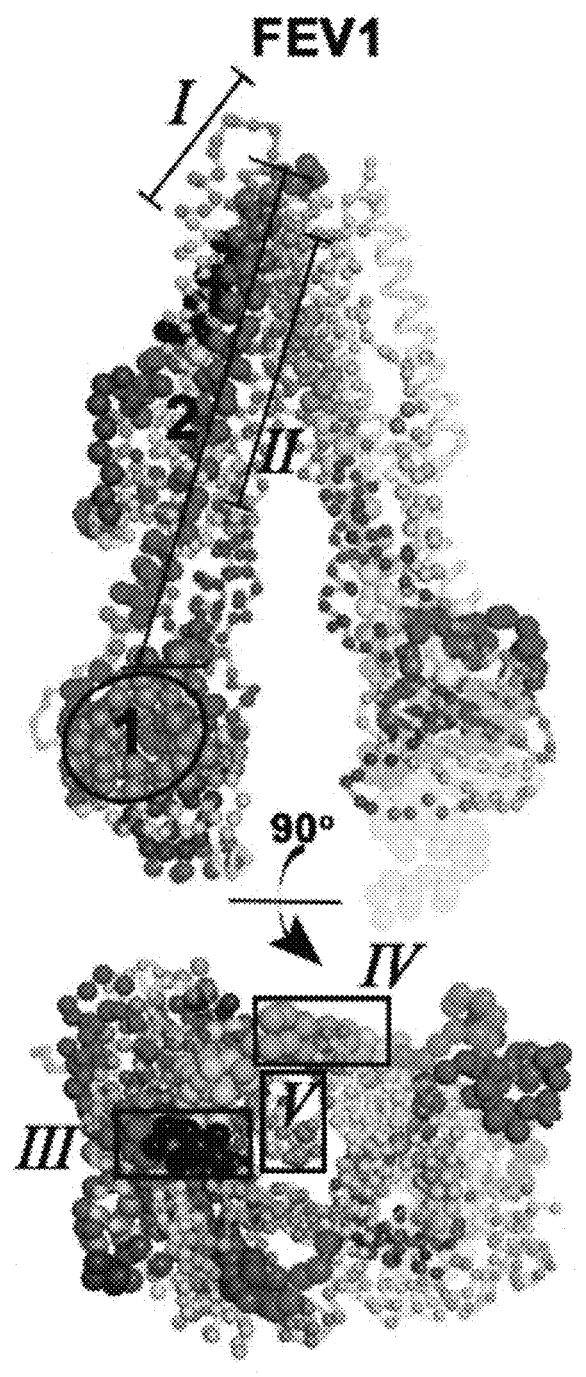
FIG. 5H illustrates a clinical functional structure generated using the FEV1 phenotype landscape of FIG. 5A. The highest confidence prediction of the phenotype generated by MK is assigned to each residue. The alpha carbon of each residue is shown as a ball with siz representing TrIdx, color representing the predicted phenotype, and transparency representing prediction confidence. The locations of tissue invariant SCV predictions in NBD1 (circle 1, large red balls) and TMD2 (bar 2, large red balls) are shown. Clusters=1\*ROMANI and =\*ROMANII in the Δ phenotype landscapes of FIGS. 5B, 5C, 5D, and 5E are indicated by bars. Clusters=\*ROMANIII–=5\* ROMANV shown in the Δ phenotype landscapes of FIGS. 5B, 5C, 5D, and 5E are indicated by boxes.
Figure 5I:
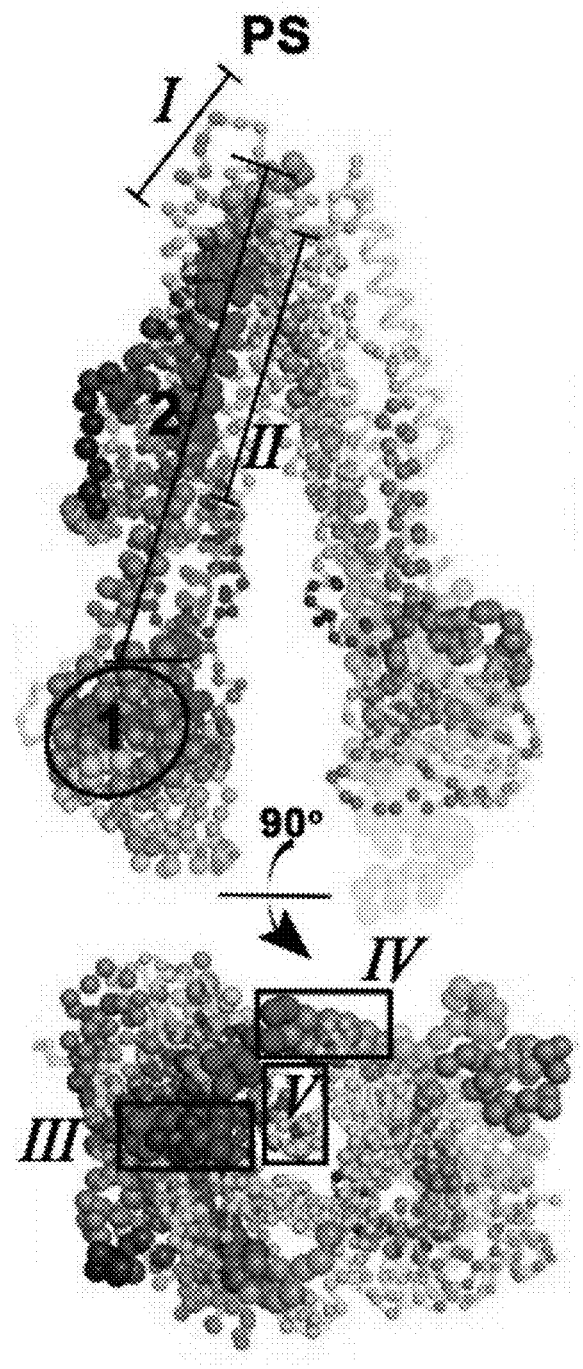
FIG. 5I illustrates a clinical functional structure generated using the PS phenotype landscape of FIG. 5A. The highest confidence prediction of the phenotype generated by MK is assigned to each residue. The alpha carbon of each residue is shown as a ball with siz representing TrIdx, color representing the predicted phenotype, and transparency representing prediction confidence. The locations of tissue invariant SCV predictions in NBD1 (circle 1, large red balls) and TMD2 (bar 2, large red balls) are shown. Clusters=1\*ROMANI and =\*ROMANII in the Δ phenotype landscapes of FIGS. 5B, 5C, 5D, and 5E are indicated by bars. Clusters=\*ROMANIII–=5\* ROMANV shown in the Δ phenotype landscapes of FIGS. 5B, 5C, 5D, and 5E are indicated by boxes.
Figure 5J:
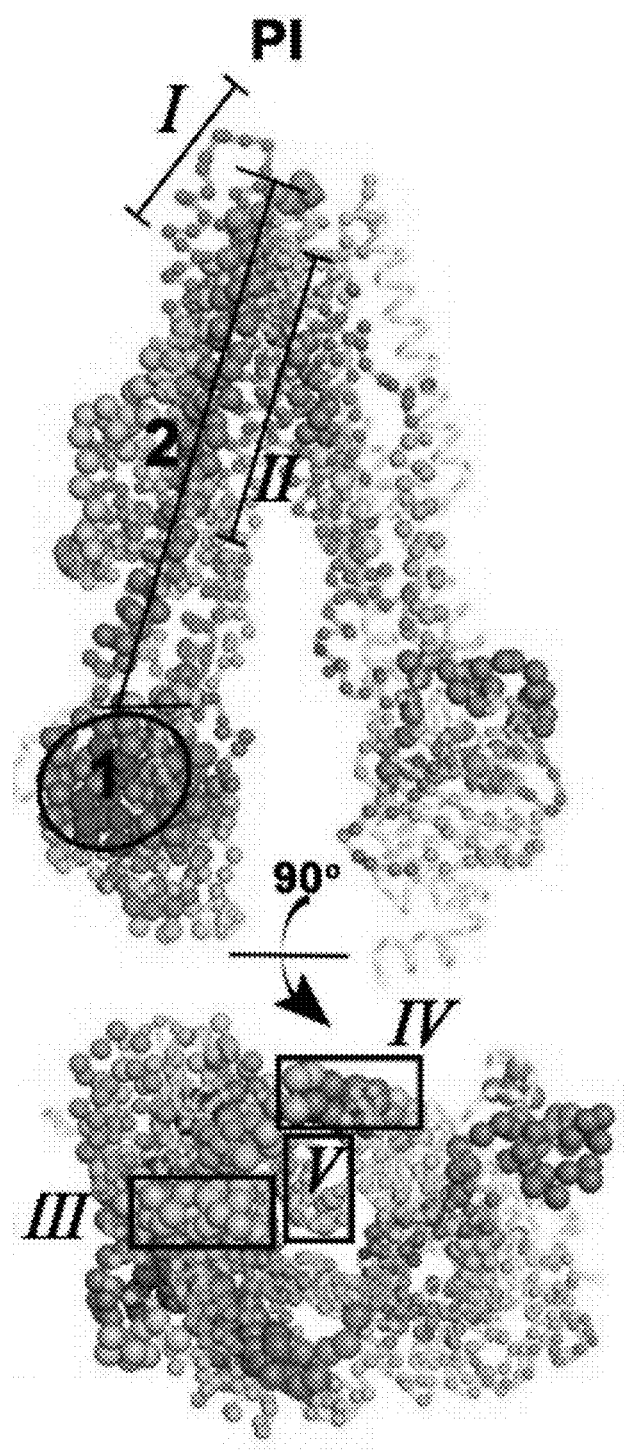
FIG. 5J illustrates a clinical functional structure generated using the SC phenotype landscape of FIG. 5A. The highest confidence prediction of the phenotype generated by MK is assigned to each residue. The alpha carbon of each residue is shown as a ball with siz representing TrIdx, color representing the predicted phenotype, and transparency representing prediction confidence. The locations of tissue invariant SCV predictions in NBD1 (circle 1, large red balls) and TMD2 (bar 2, large red balls) are shown. Clusters=1\*ROMANI and =\*ROMANII in the Δ phenotype landscapes of FIGS. 5B, 5C, 5D, and 5E are indicated by bars. Clusters=\*ROMANIII–=5\* ROMANV shown in the Δ phenotype landscapes of FIGS. 5B, 5C, 5D, and 5E are indicated by boxes.

Also, as shown in FIG. 5A, upper panel, a set of stacked flat plate heat maps may also be utilized, where each heat map may be illustrating different parameters along the z-axis. As shown in FIGS. 5B, 5C, 5D, and 5E, various combinations of heat map pairs can convey significant information in a useful way. The combination may be a difference or an average of the predicted z-values at corresponding points of two heat maps that can be mapped onto a structure as shown in FIG. 5F.

Cystic Fibrosis Example

Here, we present one example of application of VSP to the human disease, cystic fibrosis (a generalizable and proprietary principle for predicting genotypes (variation in the population defined by human genome sequencing assigned the x-axis) to any phenotypic relationship assigned to the y- and z-axis coordinates or higher dimensional (4D) landscapes that may include a time coordinate).

Figure 2A:
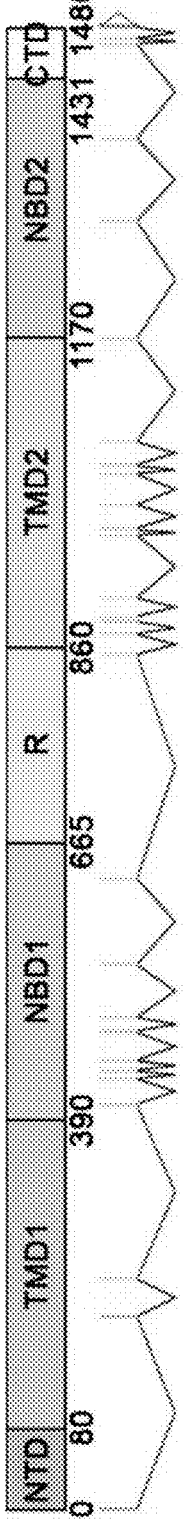
FIG. 2A illustrates a schematic representation of the variation and domain structure of cystic fibrosis transmembrane conductance regulator (CFTR): N-terminal domain 1 (NTD1); transmembrane-spanning domain 1 (TMD1); nucleotide-binding domain 1 (NBD1); regulatory insert (R); transmembrane-spanning domain 2 (TMD2), nucleotide-binding domain 2 (NBD2); C-terminal domain (CTD). The domain boundary residues numbers used in the current study are indicated.
Figure 2B:
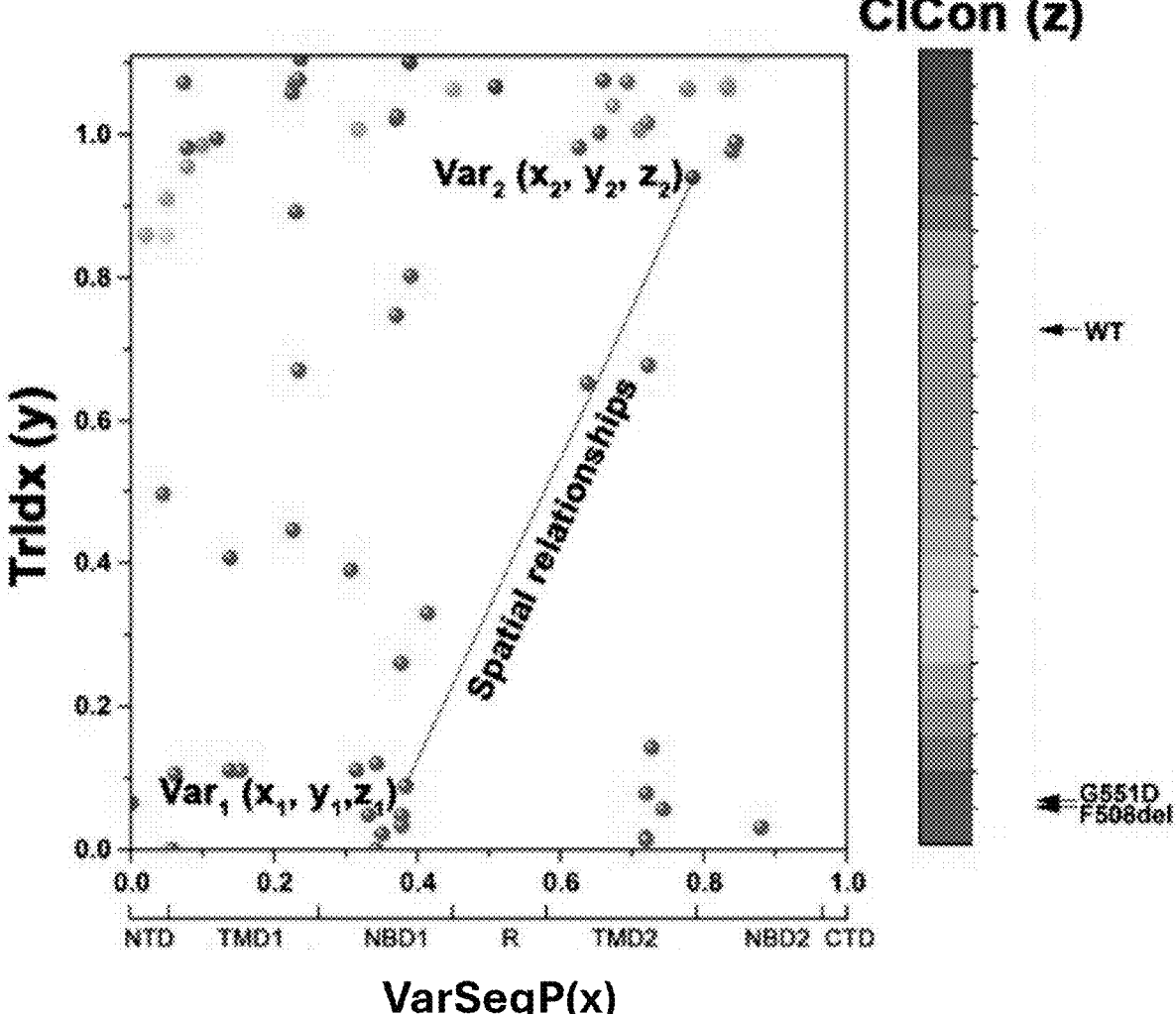
FIG. 2B illustrates CFTR variants positioned in a 2D plot by their VarSeqP (x-axis) normalized to the full-length sequence and TrIdx (y-axis) normalized to WT that is set at a value of 1. The projected z-axis (color gradient) is defined by the measured ClCon of each variant normalized to that of WT (set to a value of 1).

CFTR is multi-membrane spanning protein (FIG. 2A) that is co-translationally inserted into the ER where it acquires N-linked glycans. Upon exit from the ER, CFTR is delivered to the Golgi for transfer to the cell surface where it functions as an ion channel. To assess the genotype to phenotype transformation responsible for CF, we applied VSP to 63 well-characterized CFTR missense variants that are found above the 0.01% allele frequency in the CF patient population. Each variant's normalized linear position in the CFTR polypeptide sequence was plotted as a training input value along the x-axis genotype coordinate (FIG. 2B, VarSeqP). To capture the SCV relationships of variants genotype contributing to both cellular location and function, the input y-axis coordinate was assigned the value of each variant's trafficking index (TrIdx) (FIG. 2B, y-axis, TrIdx), which is the normalized ratio of the fraction of variant exported from the ER relative to the total variant level in the cell, where the value of the WT CFTR TrIdx is assigned a value of 1.0. The training input z-coordinate was assigned the measured chloride conductance (ClCon) value for each variant that is normalized to WT ClCon, which is set to 1.0 (FIG. 2B, z-axis, colored gradient).

Figure 2C:
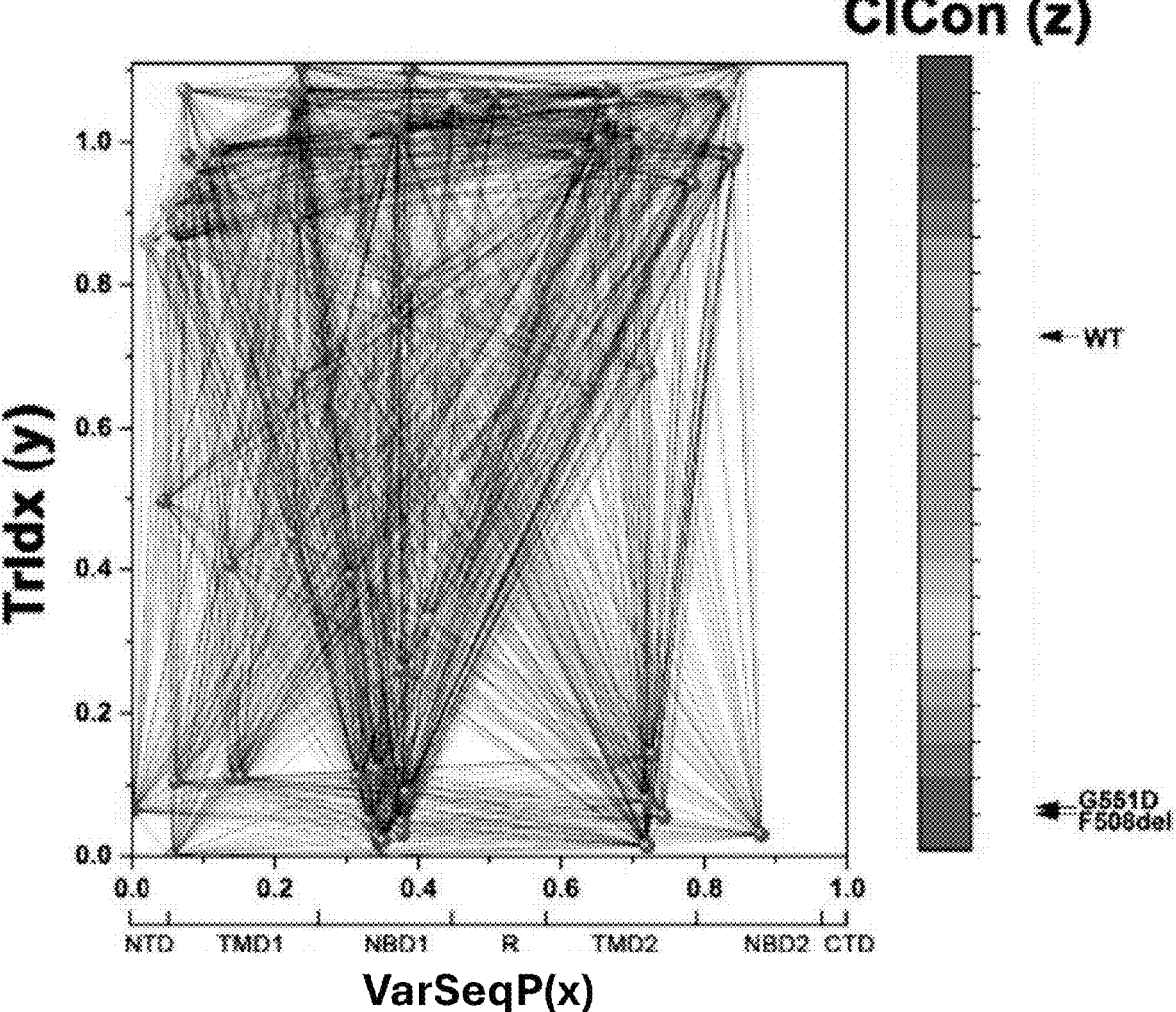
FIG. 2C illustrates spatial relationships of all possible 1953 variant pairwise combinations (black lines) representing the correlation between the spatial variance of ClCon (z-axis) and the distance values defined by VarSeqP (x-axis) and TrIdx (y-axis).
Figure 2D:
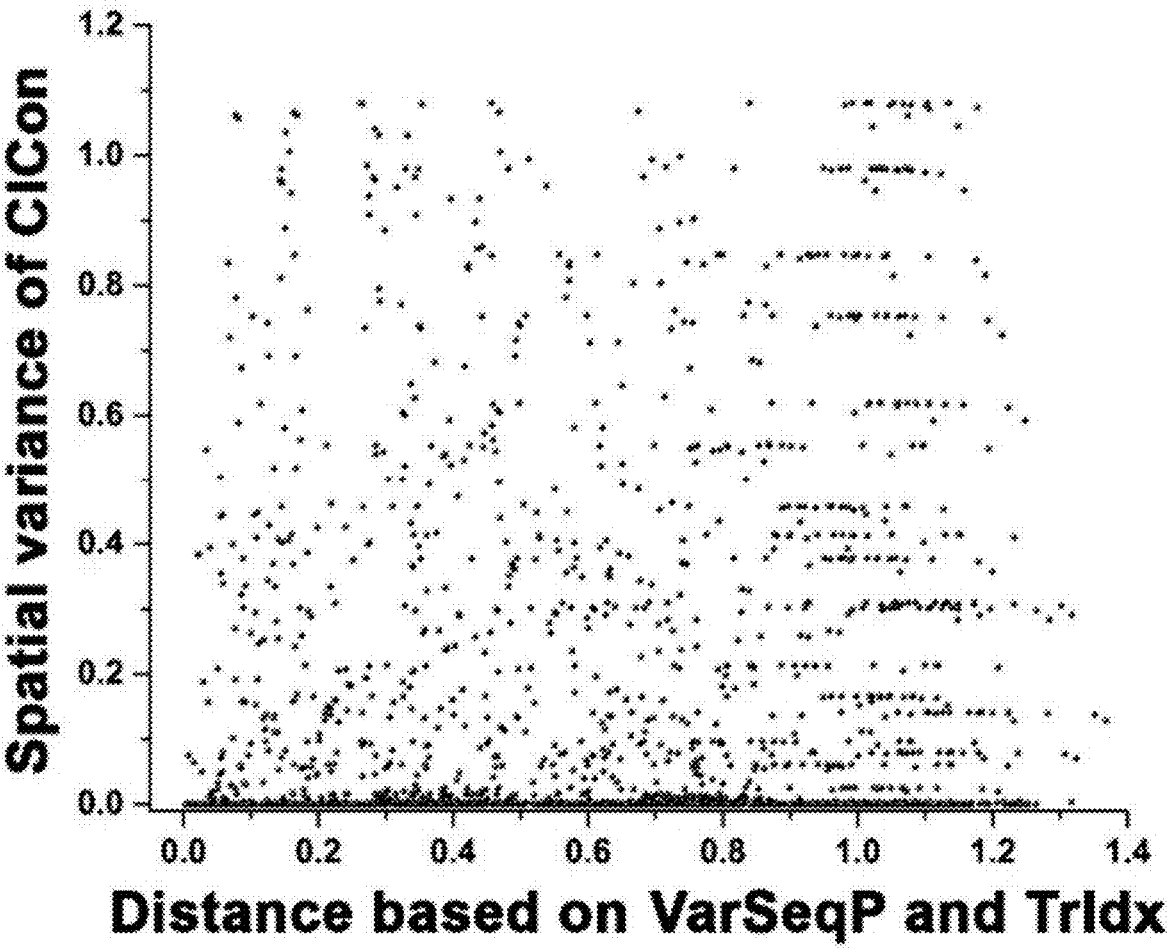
FIG. 2D is a plot of distance values and spatial variance for each comparison of FIG. 2C.

To analyze the spatial relationships for all the input VarSeqP (x-axis) in the context of TrIdx (y-axis) and ClCon (z-axis) (FIG. 2B), we calculated the distance values based on VarSeqP and TrIdx, as well as spatial variance of ClCon for all possible 1953 variant pairwise combinations (FIG. 2C, 2D). These distance values provide the first layer of 2D spatial information regarding how CFTR trafficking is changed by each variant's sequence position. The second layer of information is provided by the spatial variance that measures the variability of ClCon (the z-axis) in the context of cellular location (TrIdx) of CFTR and a variant sequence position (FIG. 2C, 2D). These 3D relationships, assessed by the molecular variogram, shows that the spatial variance of ClCon (FIG. 2E, y-axis) increases according to the changes of TrIdx and VarSeqP (FIG. 2E, x-axis) until it reaches a plateau at distance of ~0.14 (FIG. 2E , lower panel), a value referred to as the range. A range of ~0.14 (FIG. 2E , lower panel) reveals that the TrIdx and ClCon functions of variants are generally dependent on each other only over a short sequence range of ~200 amino acids. In contrast, variants with distance relationships extending beyond the range are generally not correlated. The molecular variogram now enables the calculation of SCV relationships between the known measured locations of variants to all unknown positions spanning the polypeptide sequence.

Figure 2E:
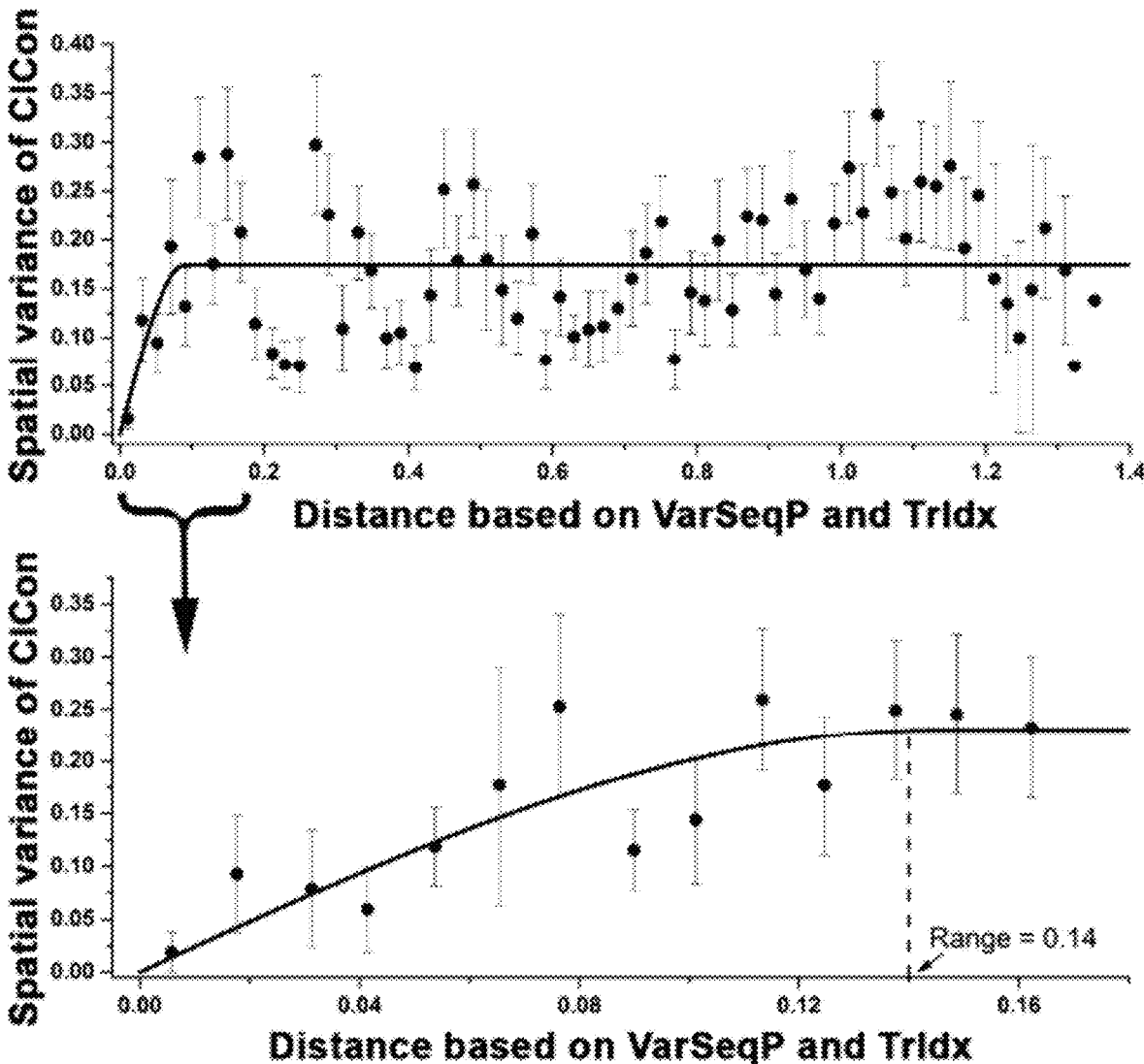
FIG. 2E is a plot with the spatial variance binned by a distance interval of 0.2 spanning the entire sequence (upper plot), or 0.012 (lower plot, higher resolution of the range sequence region) to determine the averaged value with the SEM shown for each bin. The range where the spatial variance reaches plateau is indicated in the lower plot.

The confidence to use SCV relationships to predict unknown locations can be plotted as a gray gradient delineated by contour lines in a 2D map (FIG. 3A). SCV relationships within the top 25% confidence quartile relative to all SCV relationships (set at 100%) (FIG. 3A, dark gray contours) have input variant values within the top 1/3 of the range in the molecular variogram (FIG. 2E, lower panel). Thus, their relationships are of high confidence and spatially dependent on one another for both trafficking and conductance as indicated by the close proximity of the data points (the clusters) within the contour intervals. Locations outside the 25% quartile progressively approach the plateau in the molecular variogram, reflected in the 75% quartile (FIG. 3A). They are of increasingly lower confidence in assessing SCV relationships. VSP reveals that the short sequence range defining the high confidence (25% quartile) intervals generates a 'molecular fingerprint' in the phenotype landscape* that is frequently separated by the lower confidence regions (>25% quartile) (FIG. 3A), indicating that the continuous CFTR polypeptide chain is surprisingly encoded by a very modular design principle.

We can now apply MK to generate an output phenotype landscape for CFTR to predict unmeasured ClCon in the context of TrIdx across the entire polypeptide sequence (FIG. 3B, ~2,100,000 predictions). To validate the output and properties of this TrIdx (y-axis) coupled predicted ClCon (z-axis) landscape (referred to as the ClCon-phenotype landscape*), we used a data set describing the TrIdx and ClCon properties of variants from a separate study not included in the training dataset (FIG. 3B, plus symbols). Strikingly, validation shows a very strong correlation (FIG. 3C, Pearson correlation coefficient (r)=0.81, p-value=$2 \times 10^{-4}$) between all the input measured values and the MK predicted values used to generate the output phenotype landscape. The predictive value of MK demonstrates that we can use fiduciary variants comprising <5% of the total CFTR sequence found in a subset of the CF patient population to generate phenotype landscapes that describe the genotype to phenotype transformation for all patients a result that can be generalized for all polypeptides analyzed by VSP. For example, the ClCon-phenotype landscape illustrates that for all residues that have a TrIdx value ~<0.4-0.5 (FIG. 3B, y-axis), MK predicts for output values a nearly complete loss of ClCon in response to variant residues that are distributed along the entire length of the polypeptide chain reflecting the importance of achieving the proper cellular location for function (FIG. 3B, red regions). In contrast, for CFTR variants that have a TrIdx value ~>0.4-0.5 (FIG. 3B, y-axis), MK predicts as output values substantial sequence-based variability in ClCon, from none to greater than WT. These results likely reflect sensitivity to downstream endo-membrane trafficking and channel regulation pathways unique to each cell type, as well as modifier effects reflecting variation in the human genome for each cell, tissue and patient environment. Strikingly, these results, highlighted in 3D projection of the ClCon-landscape (FIG. 3D), illustrate that the ER does not restrict export of most function-defective sequences (FIG. 3B).

Figure 3E:
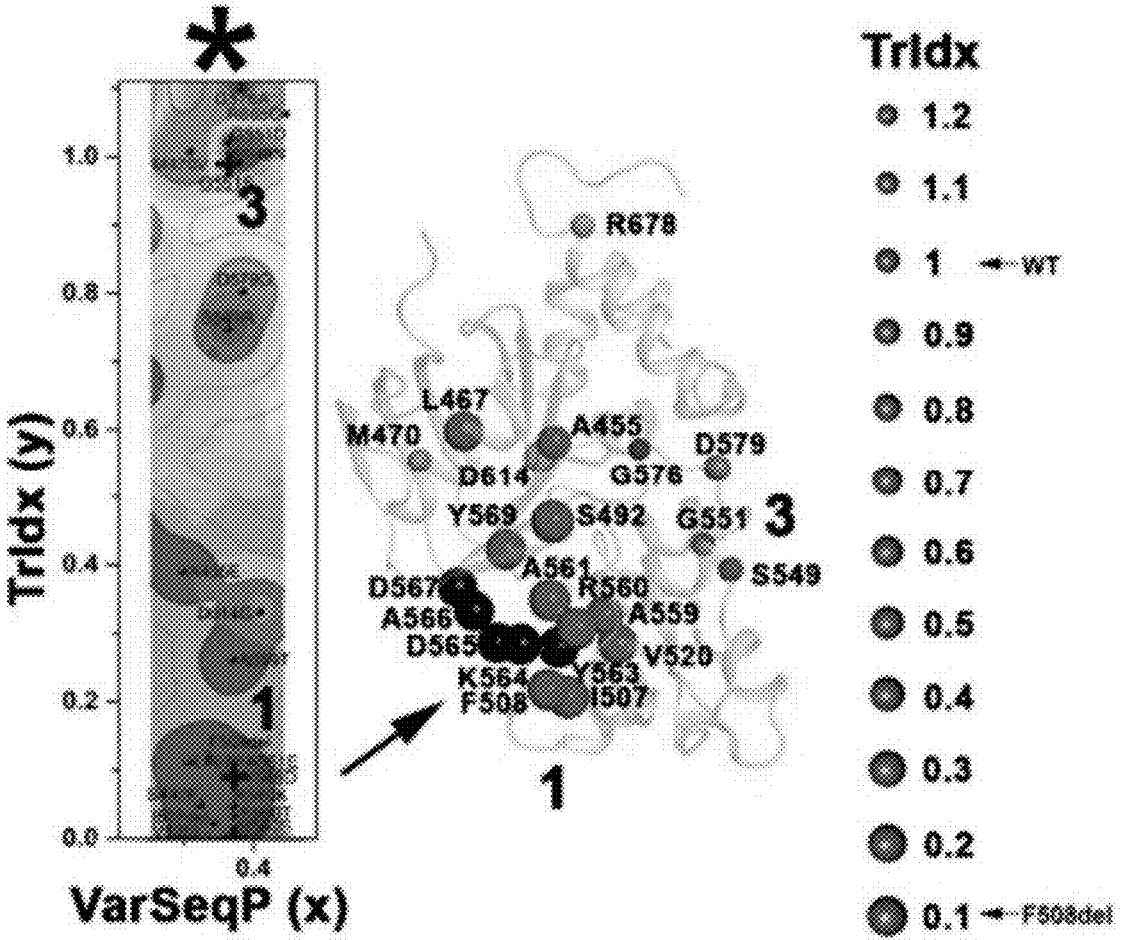
FIG. 3E shows the phenotype landscape for the NBD1 domain region (from FIG. 3B) is shown on the left. The alpha carbon trace of variant residues are highlighted as balls in the crystal structure of NBD1 (PDB: 2BBO) with ball size representing TrIdx and color representing ClCon. Black balls highlight the di-acidic exit code required for CFTR export.
Figure 3F:
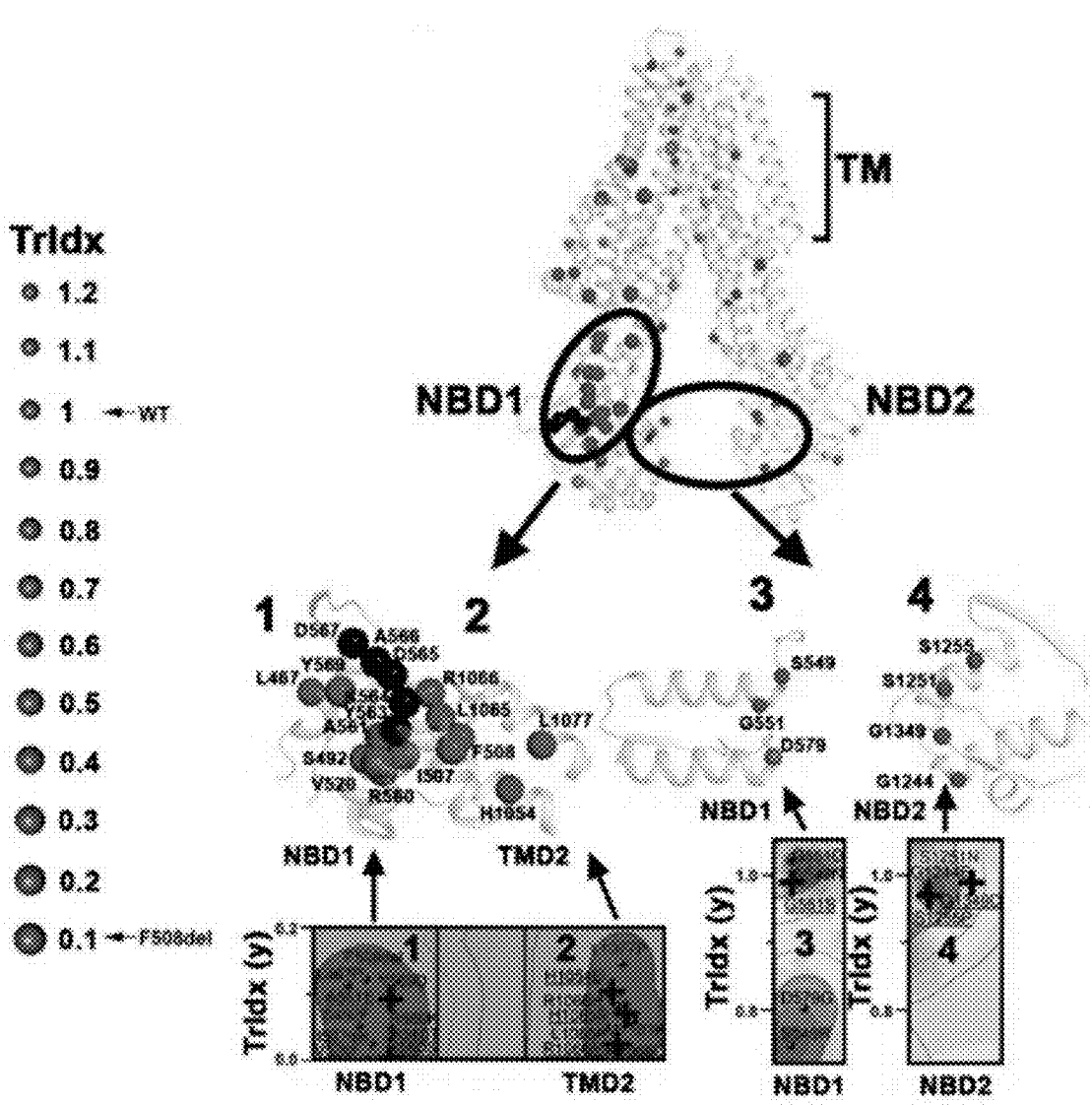
FIG. 3F illustrates variants highlighted as balls in cryo-EM structure of human CFTR. SCV clusters of residues at the NBD1-TMD2 interface and residues in NBD1-NBD2 interface are enlarged and linked to their corresponding MK landscapes (boxes). Ball size represents TrIdx and ball color represents ClCon. Black balls highlight the di-acidic exit code required for CFTR export.

To define the genotype to phenotype transformation revealed by VSP in the context of CFTR structure, we first focused on the NBD1 domain containing the prominent F508del variant (FIG. 3E). NBD1 links ATP hydrolysis through interaction with NBD2 to channel gating via inter-actions with TMD1 and TMD2. Variants in NBD1 with a TrIdx<0.2 (FIG. 3E, left panel heatmap) in the ClCon-phenotype landscape define a region in the NBD1 structure containing F508 and the critical S492 residue central to the dynamics of the NBD1 fold (FIG. 3E, left panel, SCV cluster 1, 25% quartile). SCV cluster 1 is adjacent to the di-acidic exit code required for ER export (FIG. 3E, right panel, black residues). These SCV relationships indicate that the variants forming this compact subdomain of NBD1 contribute to the ability of the di-acidic exit code to interact with COPII, a vesicular coat complex we have shown directs the formation of vesicles carrying CFTR from the ER to the Golgi. Thus, VSP defines NBD1 as the key domain in establishing spatial location to function relationships. Moreover, in the full-length structure of CFTR (FIG. 3F), NBD1 SCV cluster 1 is predicted to structurally link to a SCV cluster in TMD2, also with a very low TrIdx (FIG. 3F; SCV cluster 1 and 2). SCV clusters 1 and 2 are separated by a >75% quartile in the CF fingerprint (FIG. 3A, 3B), demonstrating that each sequence region contributes an independent module created from long-range linear sequence based spatial interactions that conformationally tune proteostasis-dependent ER export through NBD1. Functional relationships captured by VSP can also be seen in residues found at the NBD1-NBD2 interface (FIG. 3F, right side). These variants lack measur-able ClCon, but have trafficking indices >0.7 (FIG. 3B , SCV clusters 3 and 4). They have been shown to interact with each other in an alternative ATP-bound CFTR structure. Thus, SCV relationships recapitulate the inter-domain inter-actions that may be critical for regulating ClCon activity at the cell surface and consistent with the fact that NBD1 variant SCV cluster 3 defines a subdomain in the NBD1 structure that is distinct from SCV cluster 1 required for ER export (FIG. 3E , right panel). Through VSP, MK not only reveals inter-domain features of the CFTR fold found in distinct SCV modules distributed along the polypeptide chain that manage function, but the roles of residues within subdomains that tune CFTR for biology.

Figure 3G:
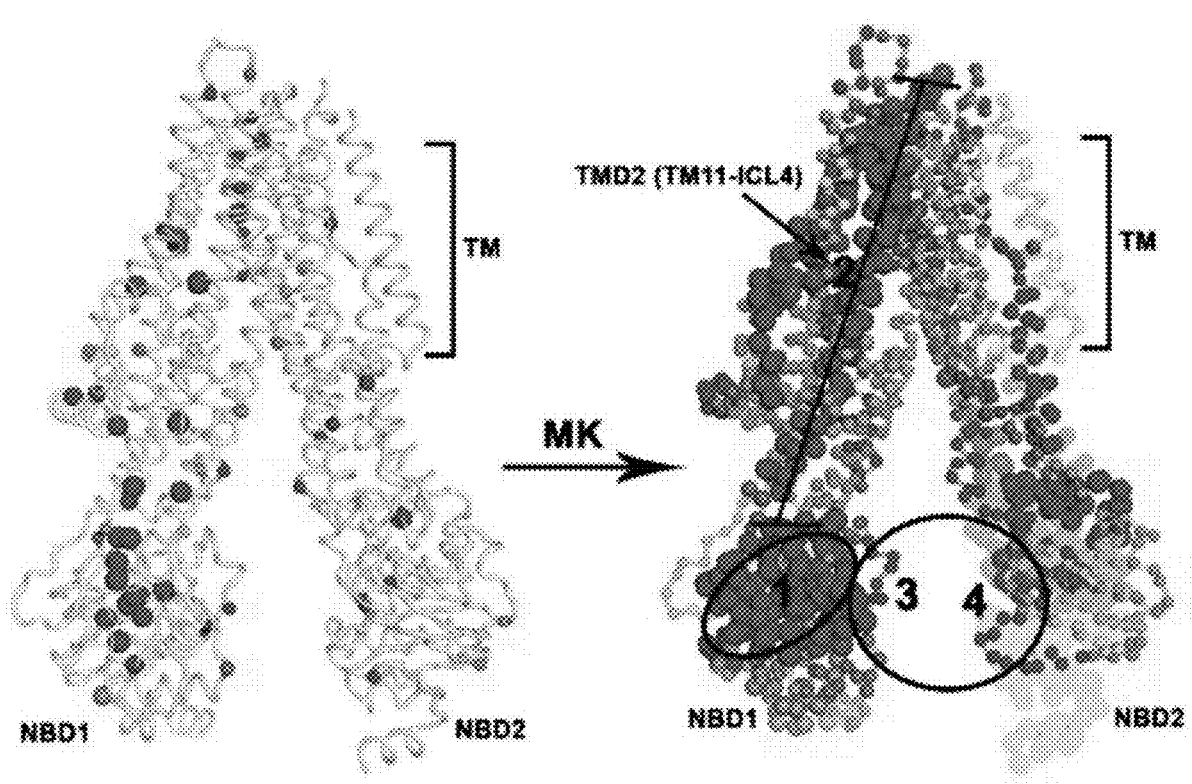
FIG. 3G illustrates the collective of sparse variant information to predict the function across the entire polypeptide sequence (the functional structure). Each residue is assigned a TrIdx and ClCon value that has highest prediction confidence. The alpha carbon of residue is shown with ball size representing TrIdx value, ball color representing ClCon, and ball transparency representing prediction confidence. Clusters 1-4 in are highlighted in the structure.
Figure 4C:
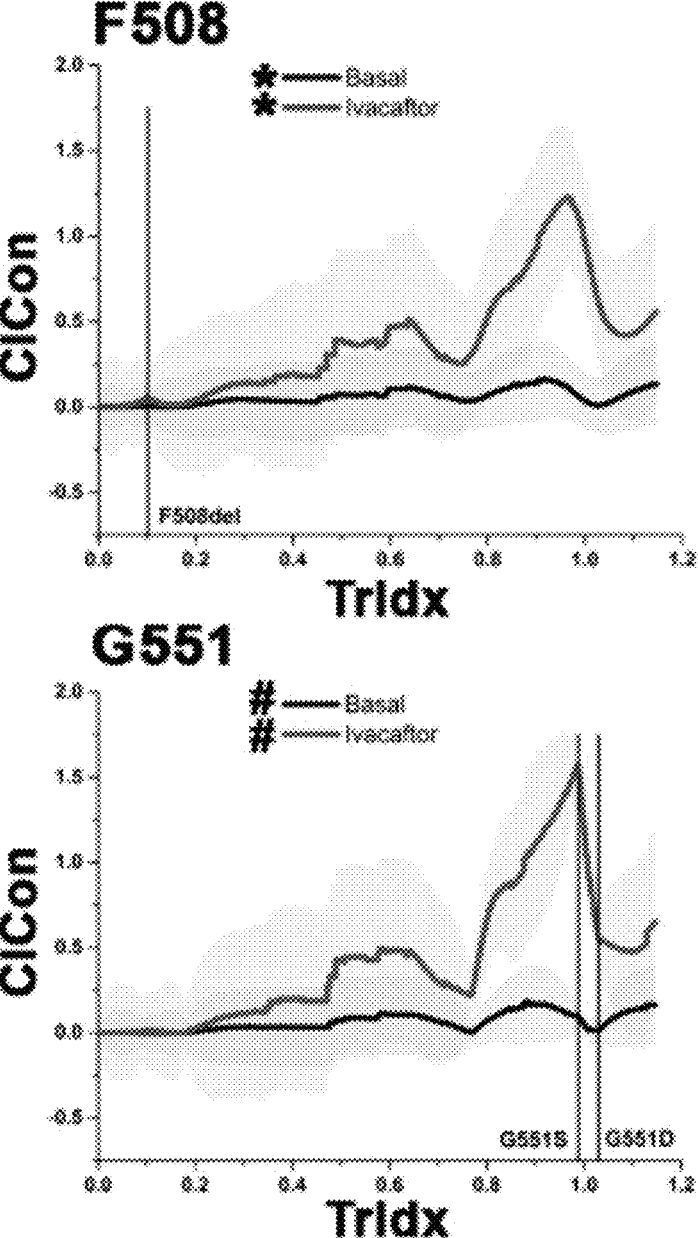
FIG. 4C shows all the TrIdx and ClCon predictions and the corresponding prediction standard deviation at residue positions 508 (upper panel) and 551 (lower panel) in the absence (black) and presence (red) of Ivacaftor extracted from landscapes in FIGS. 4A and 4B are plotted. The locations for F508del (upper panel) or G551S/G551D (lower panel) are indicated.

Strikingly, VSP provides for the first time a SCV platform to map all phenotype landscape predictions at atomic reso-lution in the CFTR structure (FIG. 3G). This composite function-based structure state of CFTR (FIG. 3G, right panel) generated from the sparse collection of variants (FIG. 3G, left panel) reveals the value of each residue in terms of TrIdx (FIG. 3g right panel, small to large balls), ClCon (FIG. 3G, right panel, color) and confidence in prediction (FIG. 3G, right panel, transparency). For example, modules in NBD1 (FIG. 3G, right panel, cluster 1) and the transmem-brane helix 11 (TM11) and intracellular loop 4 (ICL4) region in TMD2 (FIG. 3G, right panel, bar 2) display both low trafficking and conductance activity (FIG. 3G, right panel, large red balls). In contrast, those residues that have little impact on ER export (FIG. 3G, right panel, smaller balls), yet have diverse conductance values at the cell surface (FIG. 3G, right panel, red to blue), indicate that the ER does not restrict export of many, if not most, of function-defective sequences (e.g., FIG. 3G, right panel, cluster 3,4). By capturing variation across the human population, the func-tional structure of CFTR illustrates the different features of predicted modular spatial state design of CFTR (FIG. 3g) defined by its molecular range (FIG. 2E). For example, it reveals how NBD1 (FIG. 3G, right panel, cluster 1) can serve as a tunable hub in collaboration with the TMD2 module (FIG. 3G, right panel, cluster 2) to dictate the operation of the minimum export threshold, a proteostasis set-point we have defined reflecting the kinetic and thermo-dynamic forces of chaperone managed folding intermediates shown to be required for ER egress.

To demonstrate that VSP can inform us on the role of the local chemical environment in the genotype to phenotype transformation, we examined the shape of the phenotype landscape (FIGS. 4A and 4B) in response to the FDA-approved therapeutic Ivacaftor, a channel gating potentiator. While Ivacaftor has no effect on export or function of F508del required for ER export, it has a substantial biologi-cal impact in the clinic by improving the function of G551D, a variant found in SCV cluster 3 at the NBD1-NBD2 interface that traffics normally to the cell surface, but lacks conductance (FIG. 3). Spatial analysis revealed that Ivacaftor has only a minor impact on the molecular range, but increases the spatial variance of the plateau value from 0.05 in the absence of Ivacaftor to 0.29 in its presence (data not shown). This unexpected change now reveals that Ivacaftor mechanistically increases the overall spatial vari-ance (the flexibility) of the fold to restore function. This is captured in phenotype landscapes (FIGA. 4A and 4B, FIG. 4A minus Ivacaftor, 4B plus Ivacaftor). VSP demonstrates that a minimum TrIdx value of ~0.3-0.4 (FIGS. 4A and 4B) will be necessary for effective disease-related management ClCon by the drug.

The phenotype landscapes also reveal that there are diverse Ivacaftor responses even for the patients with same genotype in CFTR. For example, a vertical slice through the 3D phenotype landscape at positions F508del and G551D (FIG. 4C, indicated by asterisk (*) and crosshatch (#), respectively) can be used to generate a 2D report on poten-tial variation found in different cell-based and patient spe-cific modifier environments that would affect the prediction and hence provide a metric to assess the variable response to Ivacaftor found in the clinic. In F508del patients, though average patients do not respond to Ivacaftor, if a patient has an unknown genetic modifier or has encountered a more favorable 'stress' environment that supports trafficking, then this individual may respond to Ivacaftor treatment. In con-trast, for patients with G551D, if in an individual G551D patient who has deficient trafficking of G551D CFTR due to patient-specific genetic or environmental modifier, the patient may not respond to Ivacaftor as reported by VSP.

Figure 4D:
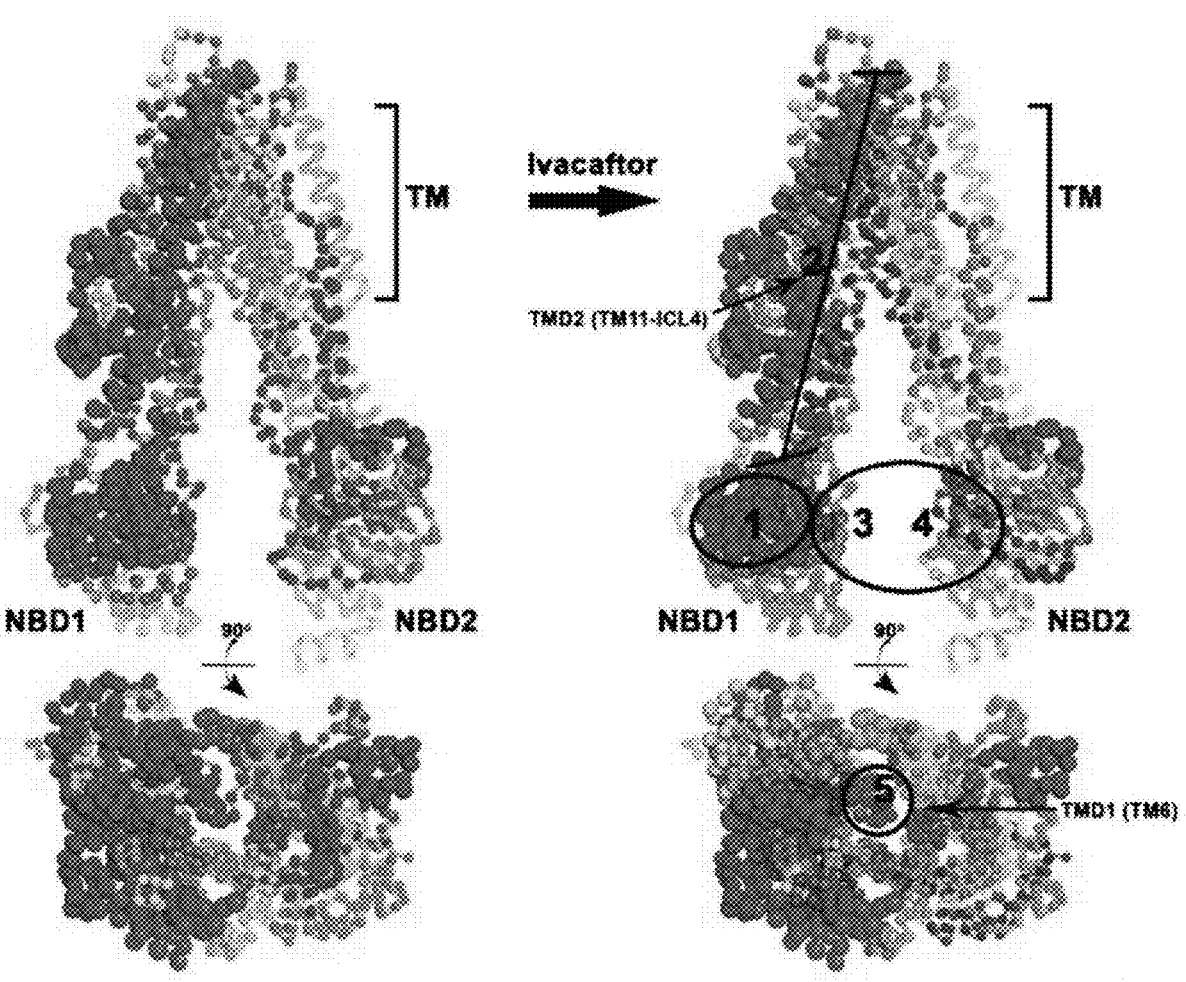
FIG. 4D shows a mapping of the function prediction of FIGS. 4A and 4B on the human CFTR structure before (left panel) or after (right panel) Ivacaftor treatment. The highest confidence prediction of the ClCon value and the corresponding TrIdx value is assigned for each residue with ball size representing TrIdx, color representing ClCon and transparency representing prediction confidence. The front and top views of the structure are shown. The SCV clusters 1-5 in FIG. 4B are highlighted in the structure.
Figure 4E:
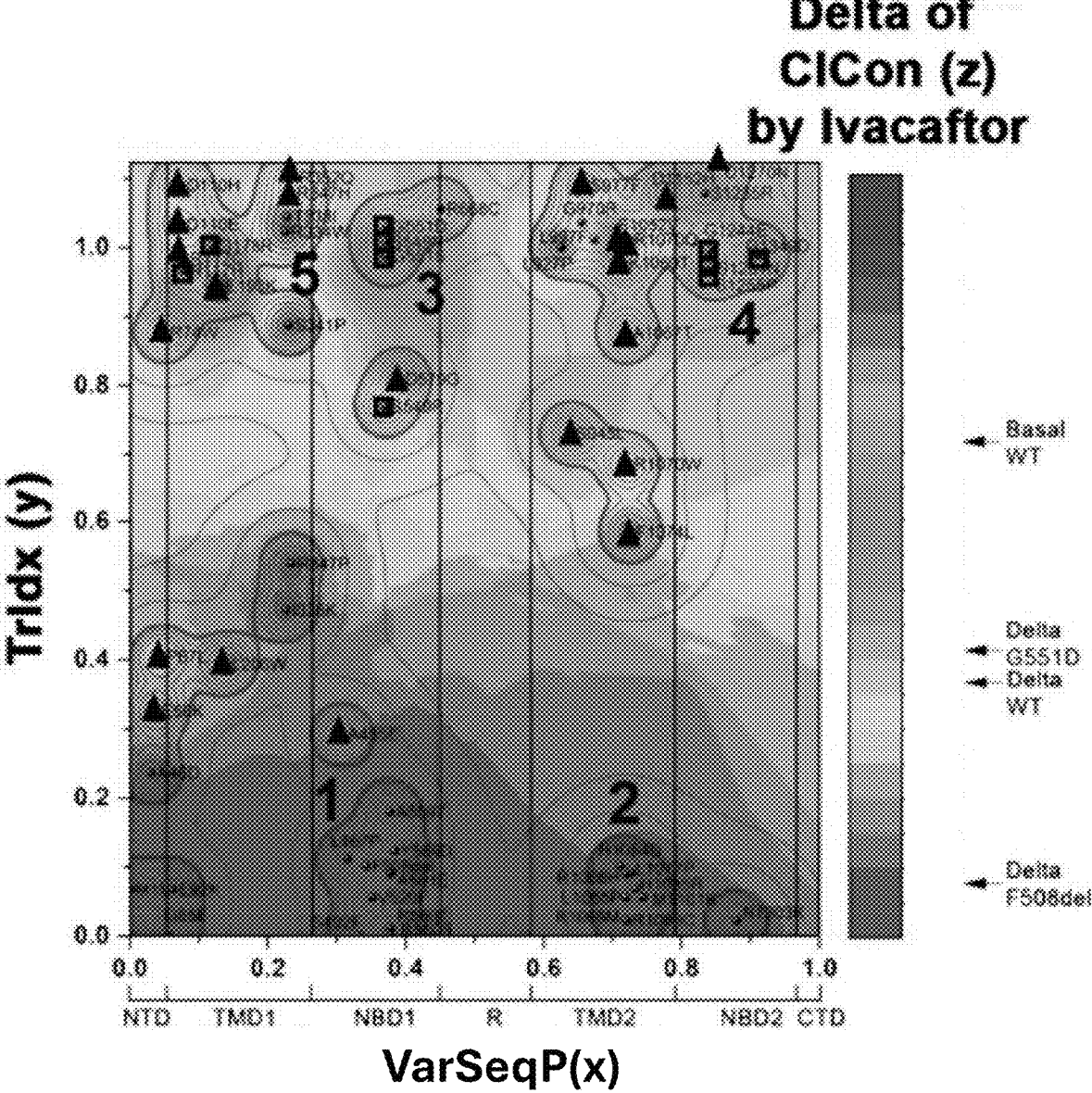
FIG. 4E is a phenotype landscape showing the predicted changes (delta (A)) of ClCon in response to Ivacaftor. The color scale represents the A value with red as no correction and green as the A value approaching the level of WT ClCon. The measured a values of WT, G551D and F508del in the absence or presence of Ivacaftor are indicated.
Figure 4F:
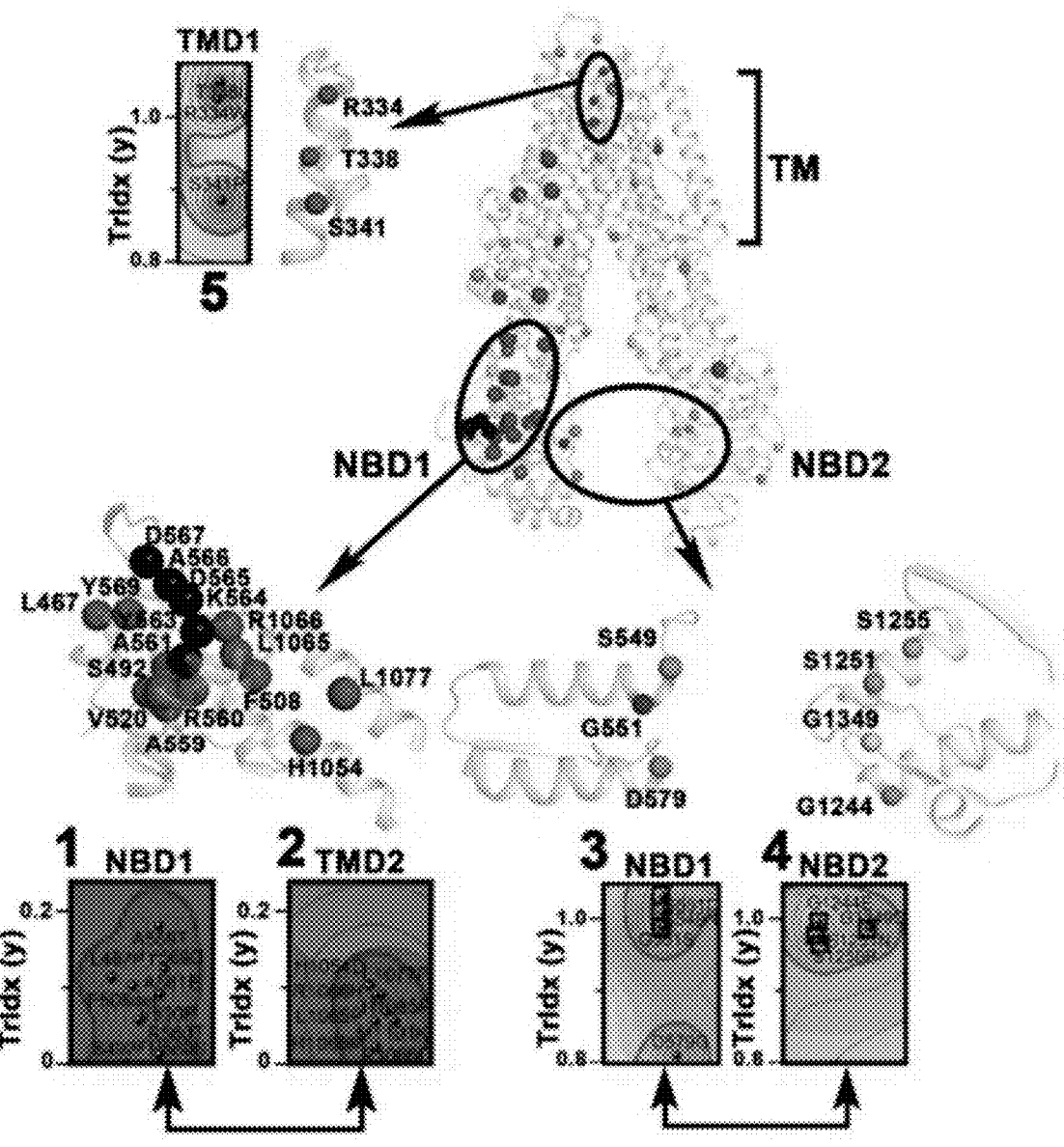
FIG. 4F shows the variant residues identified in SCV clusters 1-5 of FIG. 4E in the structure of human CFTR with the ball size representing TrIdx and color representing the ClCon response to Ivacaftor. Black balls highlight the di-acidic exit code required for CFTR export. The position of each variant in the structure is shown in the corresponding landscapes (boxes).
Figure 4G:
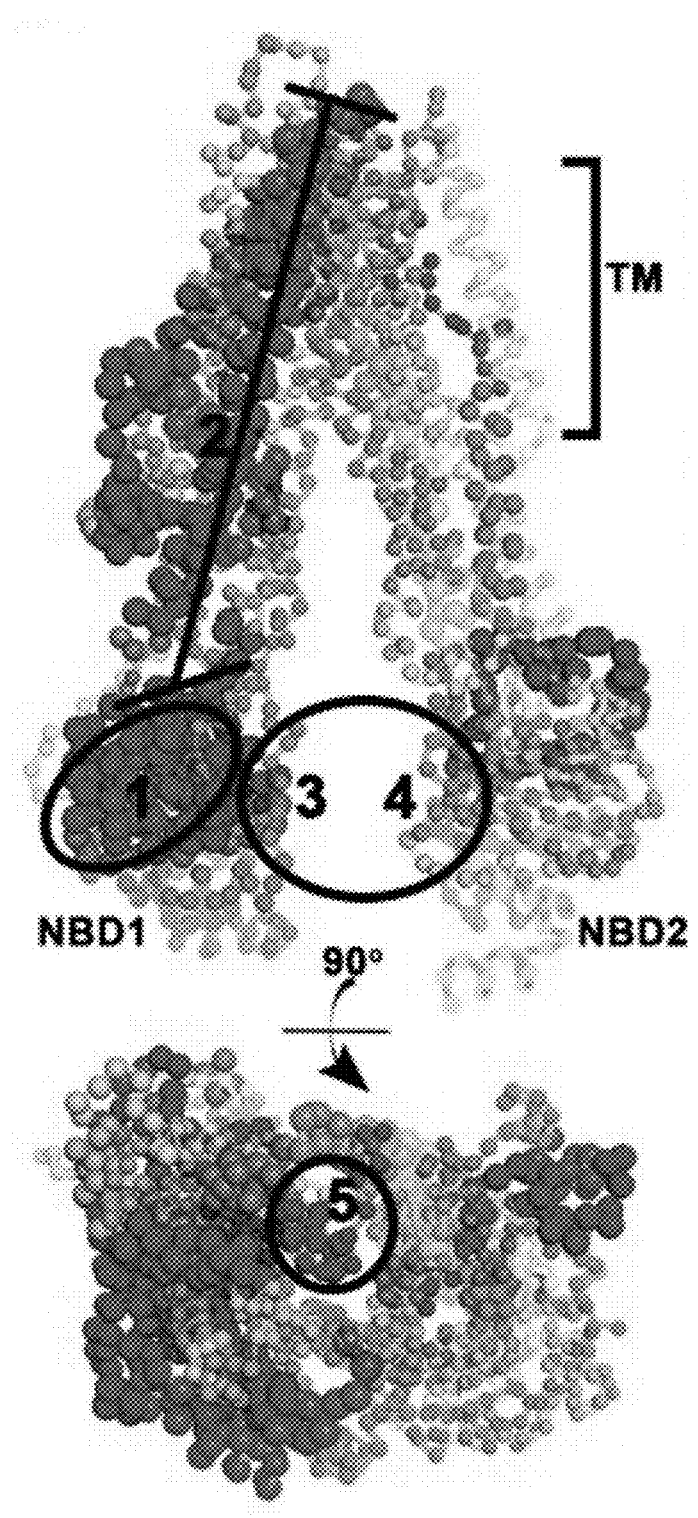
FIG. 4G shows the predicted response of Ivacaftor for each residue is mapped onto the adaptive-structure of CFTR with ball size representing TrIdx, color representing predicted ClCon response to Ivacaftor and transparency representing the prediction confidence. The SCV clusters 1-5 in FIG. 4E are highlighted in the structure.
Figure 4H:
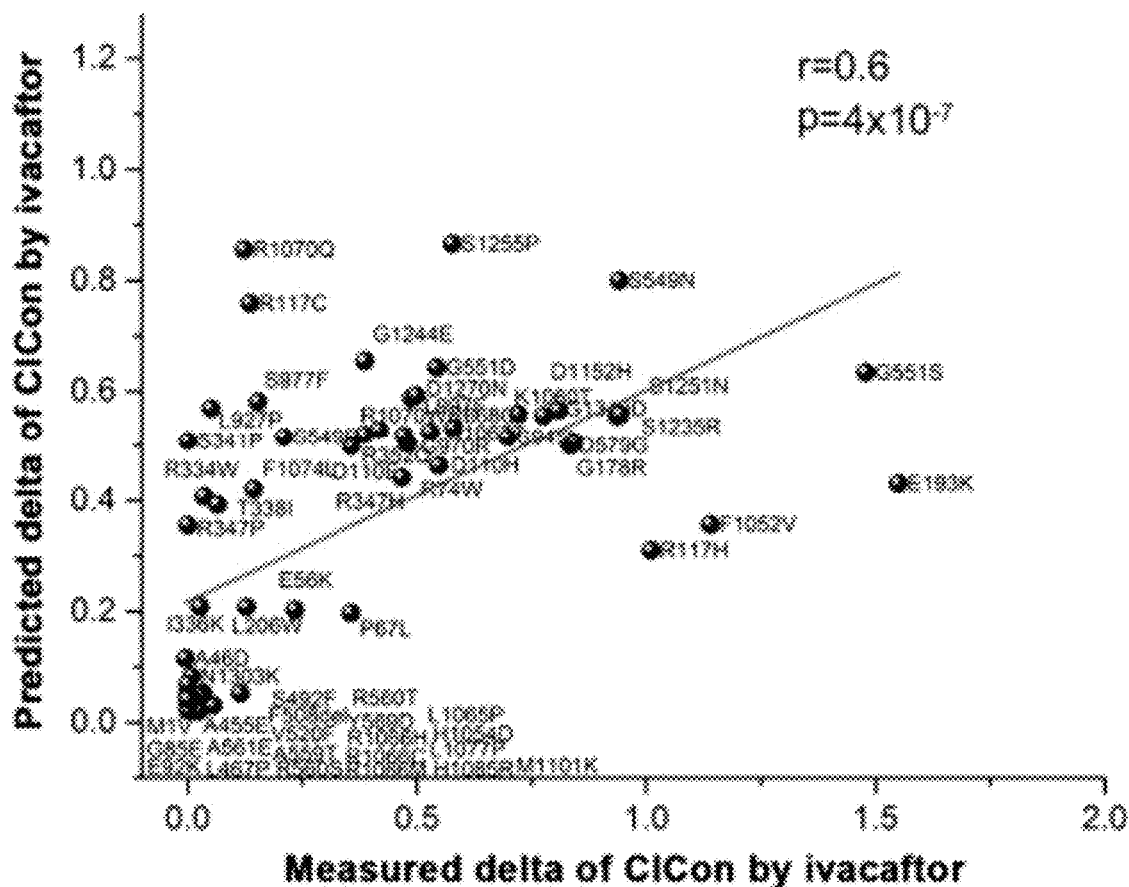
FIG. 4H illustrates validation of Ivacaftor prediction. A leave-one-out cross-validation of the Ivacaftor sensitive A phenotype landscape of FIG. 4E reveals a strong quantitative correlation with measured values (Pearson's r=0.6, p-value=$4 \times 10^{-7}$ (ANOVA test)).

The numerous changes of spatial relationships in response to Ivacafor can be also observed when mapping the pheno-type landscape onto the structure (FIG. 4D). These differ-ences, captured in a delta (Δ) phenotype landscape and structure (FIG. 4E-G), show strong cross-validation between all measured and predicted values (FIG. 4H, Pearson's $r=0.6$, p-value$=4\times10^{-7}$). For example, the SCV clusters 1 and 2 restricted to the ER and SCV cluster 5 efficiently exported from ER, failed to show a response to Ivacaftor (FIG. 4E). In contrast, variant SCV clusters 3 and 4, which participate in the interaction of NBD1 with NBD2 found at the cell surface, are highly responsive to Ivacaftor (FIG. 4E). These clusters are only part of an extensive set of spatial state changes in the function structure (FIG. 4D, right panel, smaller balls orange to blue; FIG. 4G). These results, revealed by VSP, suggests that Ivacaftor unexpectedly serves as an 'SCV agonist' by generating a ripple effect spanning most of polypeptide chain to improve the flexibility of the channel to generate a spatially configured chloride conducting open state leading to correction of phenotypic responses in cell-based models and in the clinic.

Thus, VSP generates a common platform to discriminate responders from non-responders providing a predictive platform to evaluate variants for therapeutic intervention (FIGS. 4A and 4B, right panel, squares and triangles). Variants recently approved (http://www.cff.org/News/News-Archive/2017/FDA-Approves-Ivacaftor-for-23-Additional-CFTR-Mutations/), but originally rejected by FDA for treatment with Ivacaftor, are highlighted by black triangles illustrating the predictive power of VSP. These results indicate that 63% of CFTR residues within 25% confidence quartile (813 residues) are predicted to have above 20% of WT ClCon function increase in response to Ivacaftor (FIG. 9). By providing a spatial framework to assess the impact of a therapeutic on the known (the expected) in the context of the unknown (the unexpected) residue, we posit that the collective natural variation found in the population can help us understand at atomic resolution the responsiveness any polypeptide fold to chemical challenge, an approach likely to have an enabling impact on pharmacological approaches to drug discovery using cell-based and animal models.

To demonstrate that the VSP strategy can capture the spatial state of genotype to phenotype transformations reflecting the onset and progression of the tissue specific physiologies driving clinical disease, we analyzed SCV relationships using TrIdx as the input y-axis value with known clinical measures of CF disease as input z-axis values (FIG. 5A). Clinical measures include sweat chloride (SC), forced expiratory volume in I breath (FEV1), *Pseudomonas* (PS) burden, and pancreatic insufficiency (PI). To make all z-axis input measures comparable, we normalized their values by setting the F508del value to '0' and that of WT to '1'. Here, VSP phenotype landscapes (FIG. 5A, upper panel) and their atomic resolution function structures (FIG. 5B) demonstrates that a poor TrIdx not only predicts as output poor ClCon (FIG. 5A; ClCon layer, y-axis <0.4 (red to orange)), but poor FEV1, SC and PS clinical outcomes (FIG. 5A; SC, FEV1, PS layers, y-axis <0.4 (red to orange)), undoubtedly reflecting SCV optimized presentation of the NBD1-TMD2 module-based exit code (FIGS. 3G; 4D and G; circle 1 and bar 2) operating in all clinical settings (FIGS. 5F-J, circle 1 and bar 2).

Delta (Δ) phenotype landscapes (FIGS. 5B-E, lower panels) that report on the similarity or difference of a clinical feature from the cell-based ClCon measurement reveal that some variants either under- (FIGS. 5B-E, circle I), or over- (FIGS. 5B-E, circle II) estimate the potential impact of a variant on a clinical phenotype. Moreover, □ clusters III-V (FIGS. 5B-E, arrows) illustrate the unique roles a given variant can have in a specific tissue environment. When mapped as functional structures (FIGS. 5F-J), clusters I-V are all found in the channel region (FIGS. 5B-E, bars I, II and boxes III-V), suggesting that channel residues are particularly flexible in design and likely subject to tissue specific SCV regulation. These phenotype specific SCV relationships are best captured by the distinct FEV1 and PI phenotype landscapes (FIG. 5A, compare FEV1 to PI layers) and their function structures (FIGS. 5C and 5E, compare FEV1 to PI). For example, cluster III presents as a severe phenotype for FEV1 but mild for PI (FIGS. 5C and 5E, cluster III). In contrast, cluster IV is mild for FEV1 but severe for PI (and other clinical responses) and cluster V is severe for all clinical indications as well as resistant to Ivacaftor correction but has only a mild impact on PI (FIG. 5E). Given that CFTR function in the pancreas, unlike the lung, plays an important role in bicarbonate secretion, differences quantitated in the Δ phenotype landscapes (FIGS. 5B-E; FIGS. 5F-J) reveal the potential of VSP-based phenotype landscapes to define features of the biologically relevant function structure operating in the complex environment of the individual that cannot be addressed using snapshots generated by structural methods.

Figure 6A:
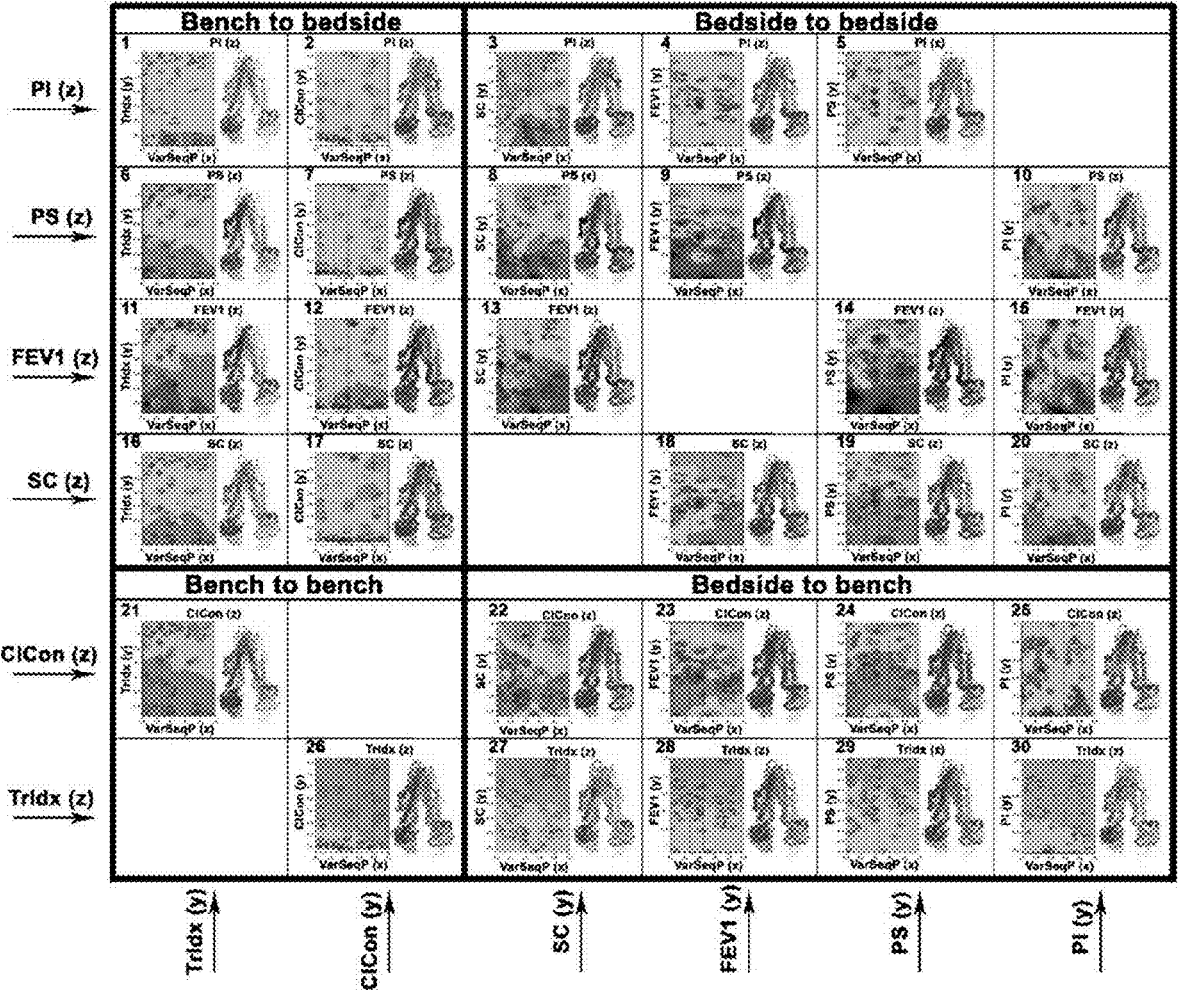
FIG. 6A shows the bench and bedside relationships commutated by VSP. (a) Predicted phenotype landscapes and functional structures that use any two combinations of the indicated cell-based or clinical features as y-axis and z-axis values are organized according to 'bench to bench' (bottom left quadrant), 'bench to bedside' (top left quadrant), 'bedside to bedside' (top right quadrant) and 'bedside to bench' (bottom right quadrant).
Figure 6B:
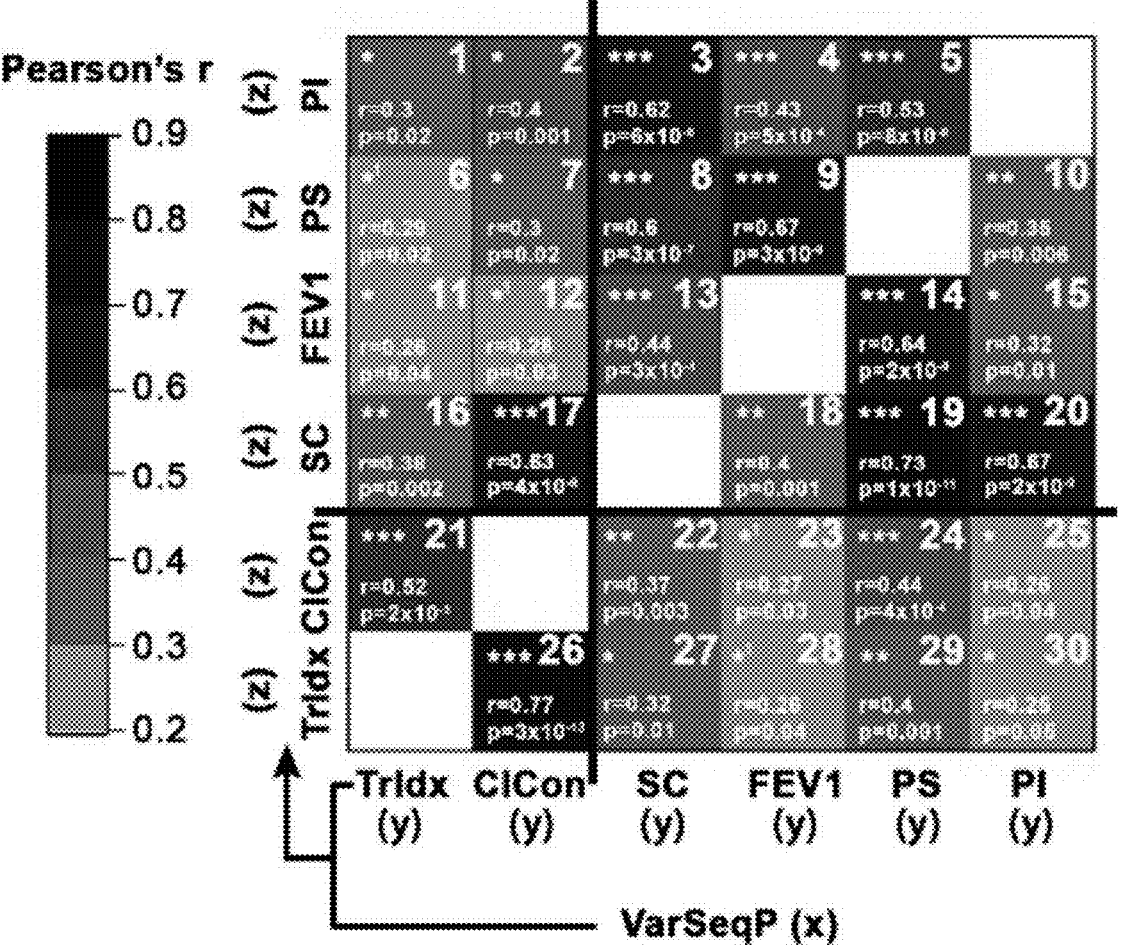
FIG. 6B shows leave-one-out cross-validation of phenotype landscapes shown in FIG. 6A. Pearson's r-value is indicated by the color scale; p-value is indicated by asterisks ((*) $0.01 < p < 0.05$; () $0.001 < p < 0.01$; (*) $p < 0.001$; (***) $p < 0.001$; (*1) $0.01 < p < 0.05$ where V754M is set as an outlier for validation given its variability in phenotype landscapes).

The diverse spatial states of CF variants in different tissue environments suggests that we can use VSP to directly analyze and compare the functional contribution of y- and z-axis features obtained from cell-based models (bench) with those found in clinical disease (bedside). For this purpose, we generated phenotype landscapes and the predicted atomic resolution function structures for all 30 pairwise combinations to cross-correlate basic and/or clinical features with one another (FIG. 6A). We arranged these relationships based on whether we use y- and z-coordinates as bench to bench (FIG. 6A-B; bottom left quadrant), bedside to bedside (FIG. 6A-B; top right quadrant), bench to bedside (FIG. 6a-b; top left quadrant), or bedside to bench (FIG. 6A-B; bottom right quadrant) phenotype features. Using a leave-one-out cross-validation analysis to evaluate the predictive value of each phenotype landscape (FIG. 6B), we found significant Pearson r-values of 0.52 (p-value=2× $10^{-5}$) and 0.77 (p-value=3×$10^{-13}$) using the bench-based model to predict either ClCon or TrIdx-phenotype landscapes as the output z-axis value, respectively (FIG. 6A-B; bottom left quadrants). Moreover, statistically significant SCV correlations were found using FEV1, SC, PS, or PI as an input y-axis value to predict a different clinical feature as the output z-axis value (FIG. 6A-B; top right quadrant). For example, we observed a significant quantitative correlation using input FEV1 as the y-axis to predict output PS burden as the z-axis (FIG. 6A-B; panel 9, Pearson's r-value=0.67, p-value=3×$10^{-9}$), or conversely, using input PS to predict output FEV1 (FIG. 6A-B; panel 14, Pearson's r-value=0.64, p-value=2×$10^{-8}$). These results are consistent with the fact that these features are physiologically linked in lung-associated CF disease. In contrast, when using PI as the y-axis coordinate to predict FEV1 as the z-axis value we found a substantially lower Pearson's r-value (FIG. 6A-B; panel 15, Pearson's r-value=0.32, p-value=0.01) consistent with their different physiologic role(s) in CF.

Figure 7A:
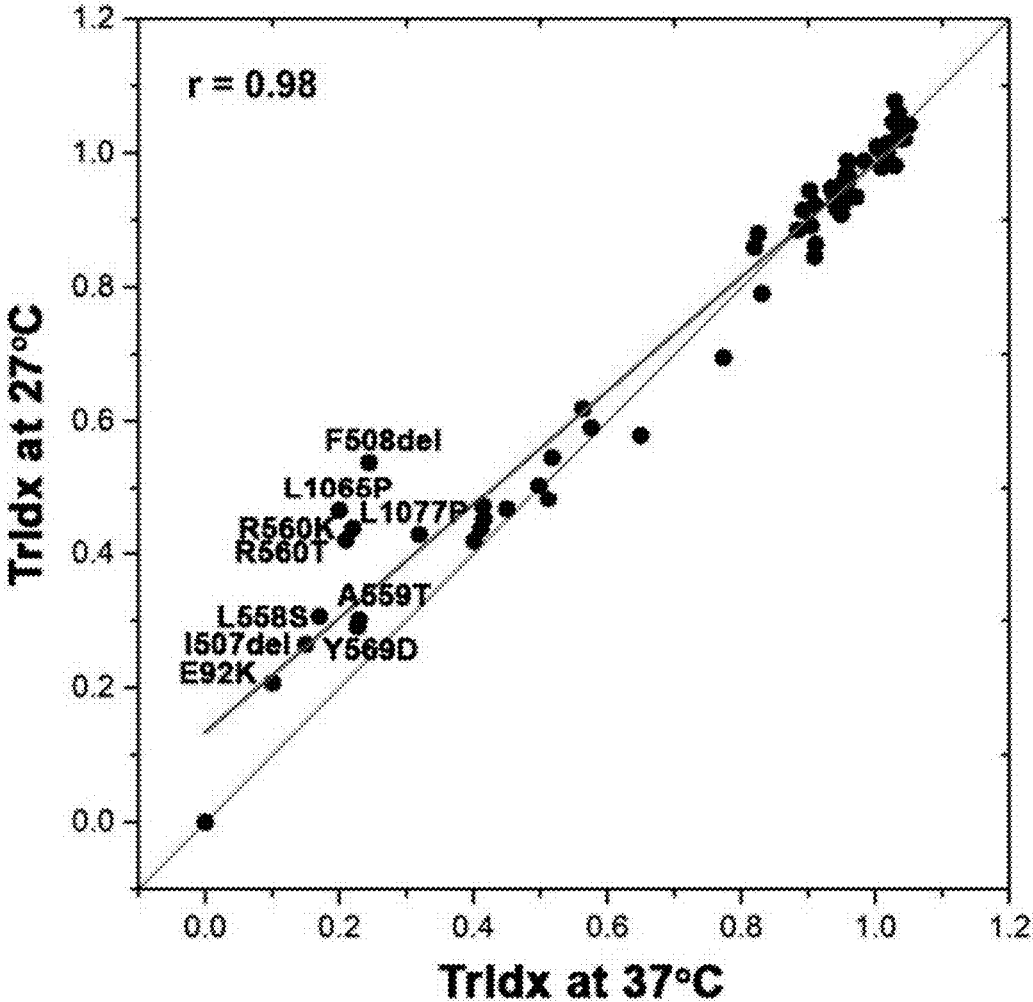
FIGS. 7A, 7B, and 7C show correlation between trafficking index (TrIdx), absolute Band C, and function respectively of CFTR variants at 37° C. and 27° C. The Pearson's r is indicated. The top 10 responsive residues are labeled. If F508del is not in the top 10 response list, it is labeled as *F508del.
Figure 7B:
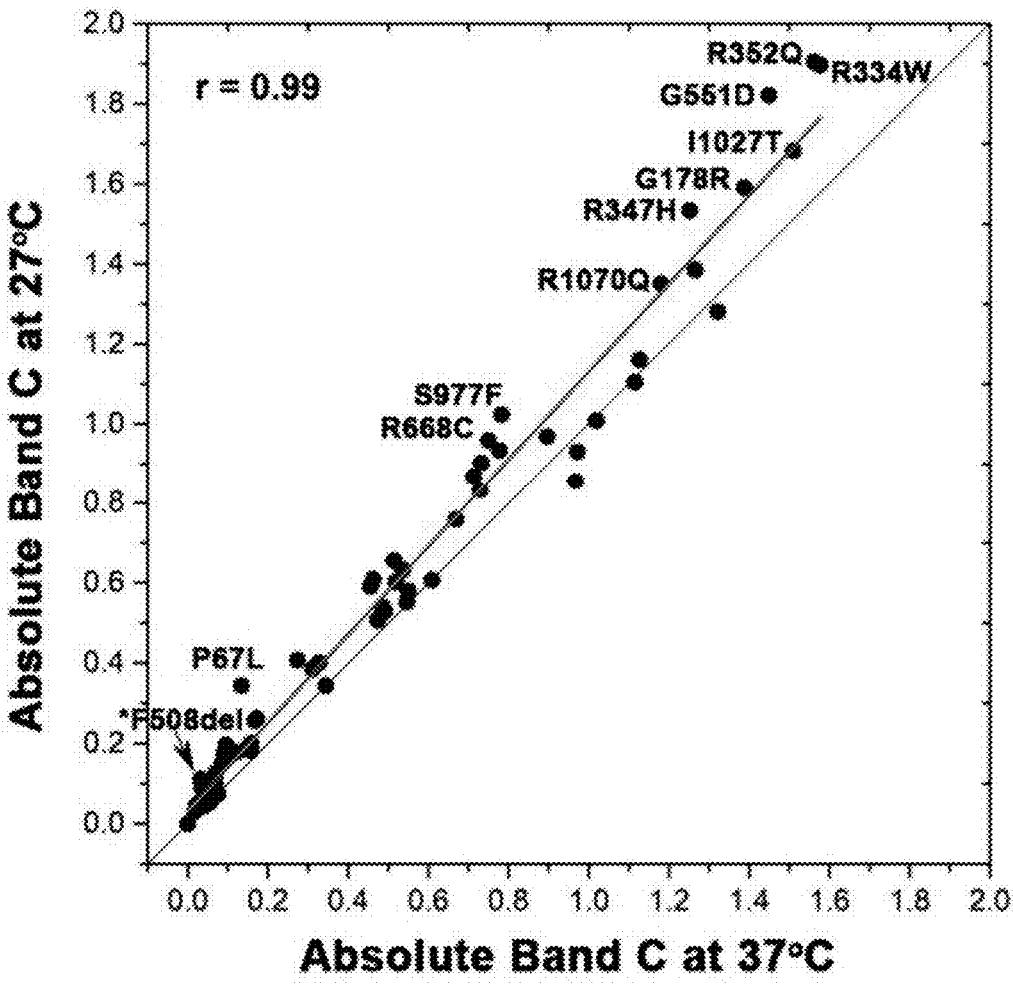
Figure 7C:
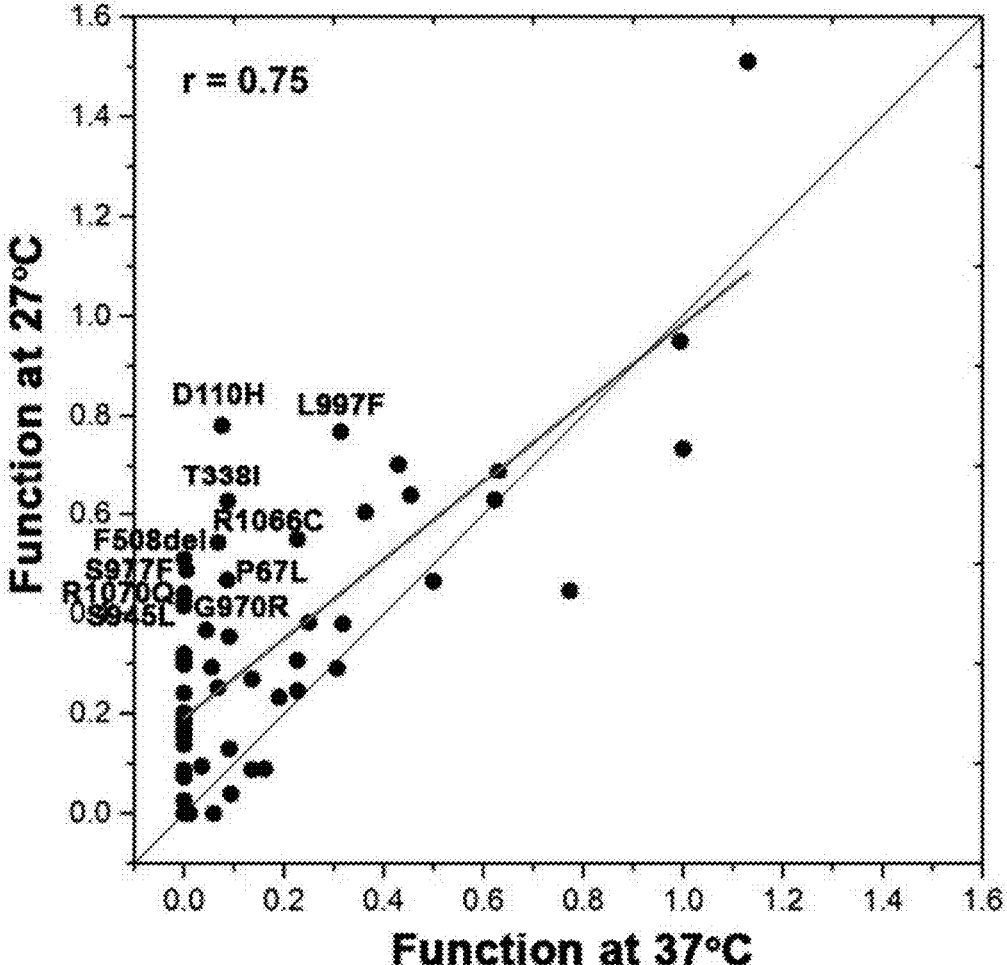

To assess the impact of the environment perturbation on CFTR function, we took advantage of the F508del variant temperature sensitivity whose trafficking from ER to cell surface function can be significantly enhanced by incubating cells at reduced temperature (27° C.) The impact of temperature on other variants has not been determined. To understand the impact of temperature on multiple domains in CFTR polypeptide, we tested trafficking index (TrIdx), mature glycoform level and the chloride channel function for a collection of 64 CF variants for at both physiological (37° C.) and low (27° C.) temperature (FIGS. 7A-C). The trafficking of CFTR can be measured by separation of the ER localized glycoform (referred as band B) and post-ER Golgi associated localized glycoform (referred as band C) through SDS-PAGE gel. Trafficking index (TrIdx) is calculated by the ratio of band C relative to total CFTR (band B plus band C) and then normalized to WT value at 37° C. The observed correlation of TrIdx of variants between physiological (37° C.) and low temperature (27° C.) (FIG. 7A) suggests for the first time that reduced temperature provides substantial correction of not only TrIdx for F508del but for other variants with low residual TrIdx at 37° C. This result indicates a central problem in the overall F508del CFTR patient biology that needs to be fixed is thermodynamic (FIG. 7A), a feature common to many destabilizing mutations in human disease. Intriguingly, the pattern of absolute band C correction (FIG. 7B) is different from TrIdx correction (FIG. 7A) showing that the variants with a higher level of absolute band C at 37° C. are generally more stabilized by 27° C. This result suggests that 27° C. can increase post-ER stability for some variants without an improvement of their TrIdx. Thus, we can uncouple ER export from downstream events in the exocytic pathway affecting the stability of the fold[1]. In contrast, the trend for channel function correction (FIG. 7C) shows higher correction for the variants with low residual function at 37° C., indicating the absolute band C level does not necessarily determine the channel function and that additional properties of the fold in post-ER compartments may impact thermal stability reflecting complexity in central dogma design of the cell.

To assess the SCV matrix linking sequence-to-function-to-structure relationships to drive temperature sensitivity, the 64 variants are positioned in sequence-function space by plotting their variant residue positions relative to full length CFTR on the x-axis, their TrIdx (FIG. 7D), absolute band C (FIG. 7E) or function (FIG. 7F) at 37° C. relative to WT on the y-axis, and their TrIdx (FIG. 7D), absolute band C (FIG. 7E) or function (FIG. 7B) at 27° C. relative to WT on the z-axis. By analyzing the SCV relationships of our collection of sparse variants connecting these functional values to sequence position, we can define their molecular variograms that describe the overall spatial variance features of the data. The molecular variograms reveal that the spatial variance of CFTR function in response to low temperature of 27° C. increases with distance of residual function of variants at 37° C. along the polypeptide sequence position, a result that is consistent with recent reports showing the residual function of CF variants predict the therapeutic responses.

Figure 7D:
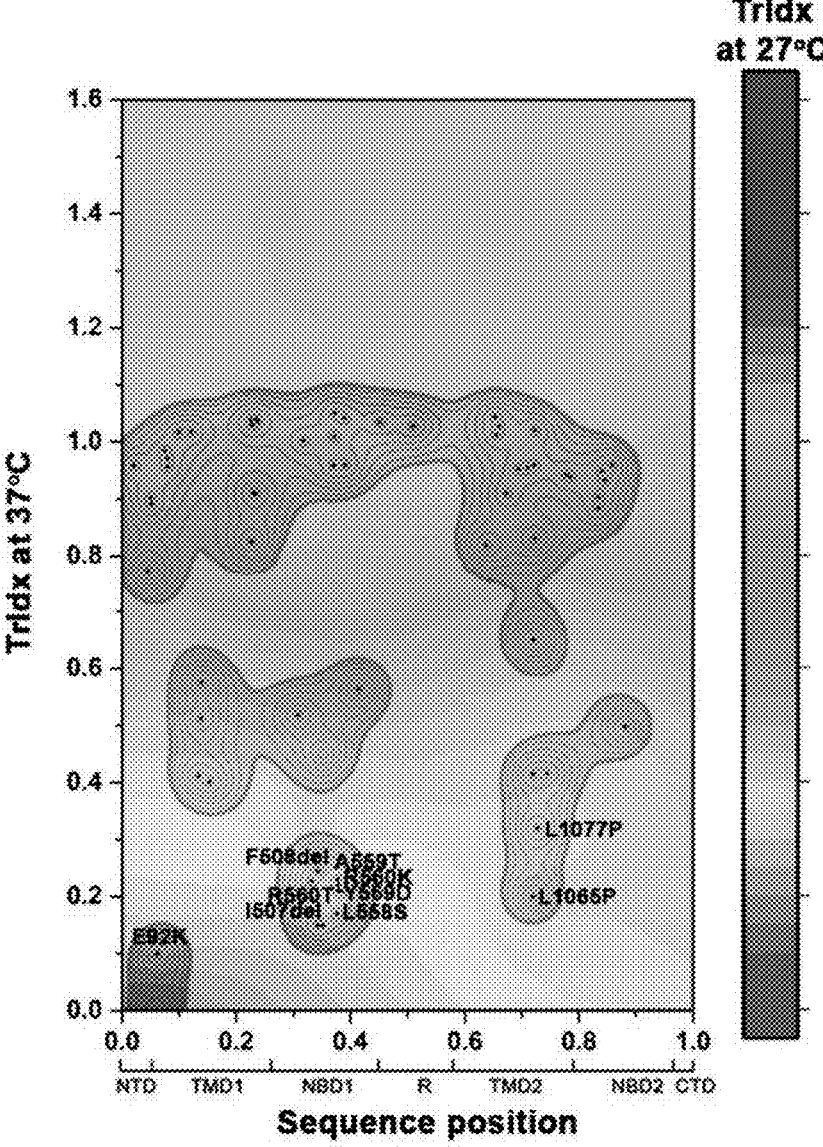
FIGS. 7D, 7E, 7F shown phenotype landscapes for TrIdx, absolute Band C, and function respectively linking the sequence position of variants (x-axis) to phenotype at 37° C. (y-axis) and 27° C. (color scale in z-axis). The prediction confidence for each prediction is shown as contour lines.
Figure 7E:
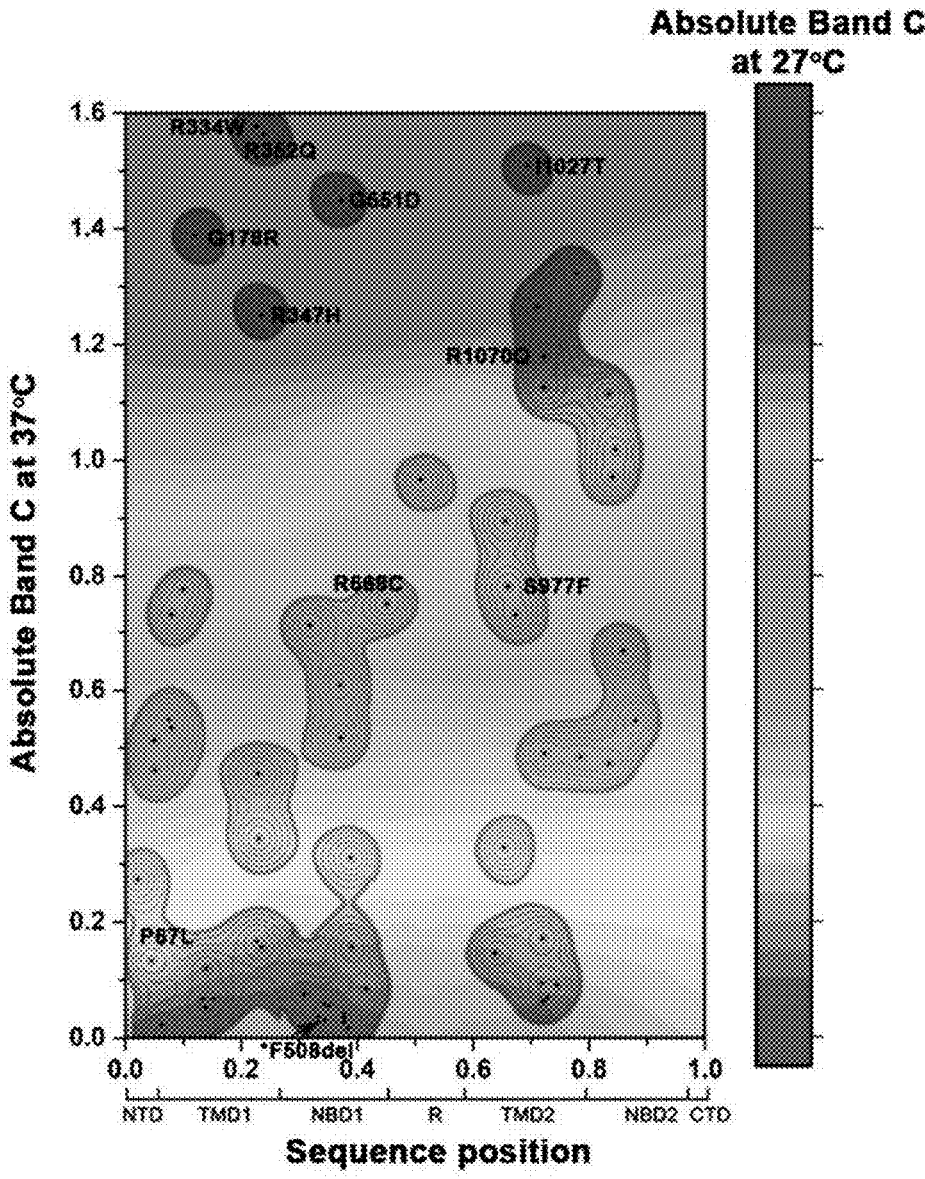
Figure 7F:
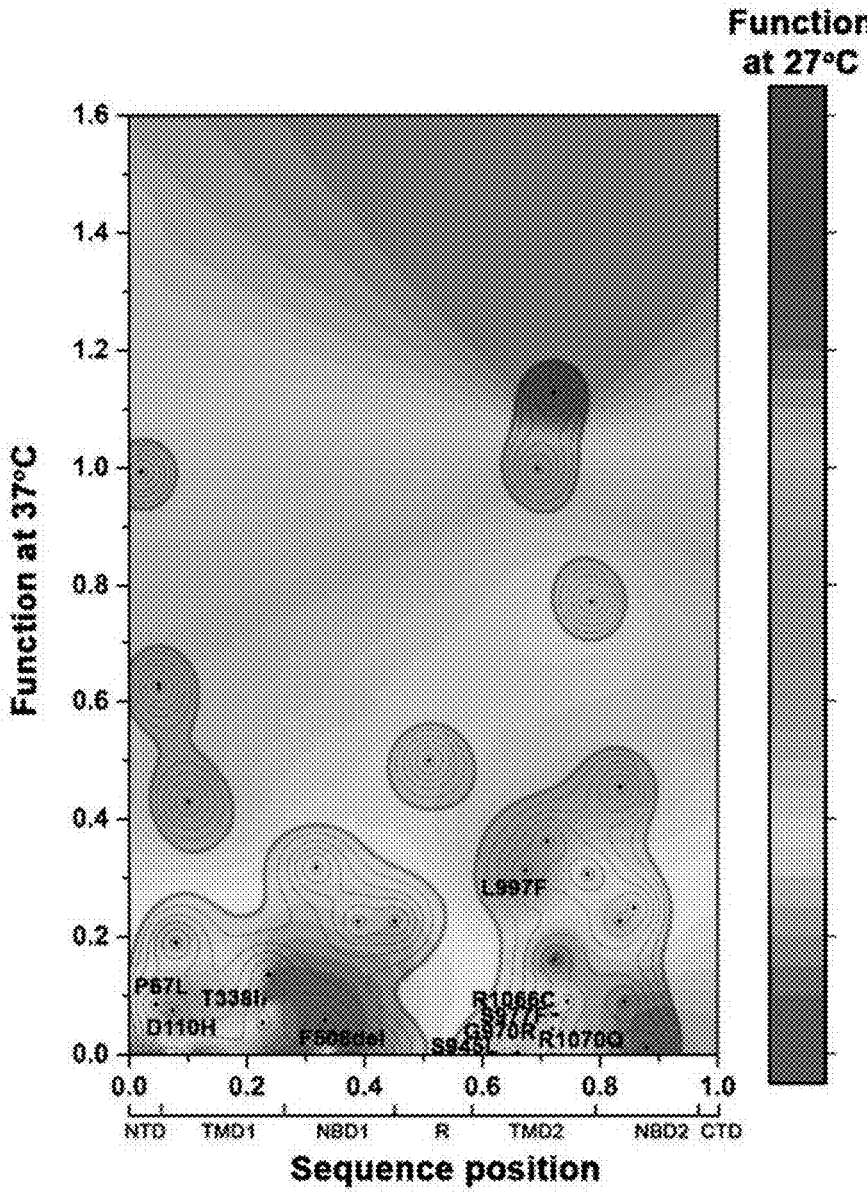

To define the high-definition sequence-function space in response to temperature, we used VSP to build the phenotype landscapes (FIGS. 7D-F) for the entire CFTR polypeptide by interpolating the missing values based on the molecular variograms. The landscapes achieve significant accuracy in predicting temperature response as validated by the leave-one-out cross-validation with Pearson's r=0.97 for TrIdx (FIG. 7D), Pearson's r=0.99 for absolute band C (FIG. 7E) and Pearson's r=0.54 for function (FIG. 7F) between the measured and predicted variant function illustrated as 2D colored projection of the z-axis values. VSP also generates a confidence value in the form of uncertainty for each prediction based on the spatial organization of the data that are plotted as contour lines in the phenotype landscapes (FIGS. 7D-F). The area inside the bold gray contour line indicates the top 25% confidence prediction, a value that recovers most the CFTR sequence (FIG. 7D). Phenotype landscapes for TrIdx, absolute band C and function reveal distinct patterns (FIGS. 7D-F). For example, the predicted high confidence regions (regions with low uncertainty) are more spread out across the TrIdx landscape (FIG. 7D) and the absolute band C landscape (FIG. 7E), while the high confidence regions in the function landscape are more clustered at the bottom (FIG. 7F). These SCV results suggest that variants with low function can have a large variety of TrIdx and absolute band C values. Furthermore, TrIdx landscape reveals the highly responsive variants mainly locate in NBD1 domain and TMD2 domain (FIG. 7D), while the highly responsive variants for absolute band C spread across different domains in the polypeptide on the top of the landscape with high residual function at 37° C. (FIG. 7E). In addition, the function phenotype landscape shows the main corrected regions locate in TMD1, NBD1 and TMD2 domains (FIG. 7F). These differential responses revealed by SCV generated phenotype landscapes predict potentially different molecular mechanisms responsible for temperature shift to impact different features of CFTR biology.

To capture both the local and long range inter-residue relationships on the phenotype landscapes to illustrate the different mechanisms for different features in response to low temperature, we developed a method referred to as Variation Capture (Var-C) (FIGS. 7G-I) based on the covariance of pairwise residues in response to environment changes derived from the SCV landscape (FIGS. 7D-F). The Var-C map is a covariance matrix that captures both the local and long-range association of any pairwise residues (e.g. residue A and B) along the primary sequence. The control residual value ($A_r$ or $B_r$) and low temperature or compound treated value ($A_t$ or $B_t$) for each residue are assigned as the value with lowest uncertainty from the phenotype landscape built through VSP. The covariance matrix of any paired of residues is calculated by:

$$\mathrm{Cov}(A,B)=(A_r-\overline{A})(B_r-\overline{B})+(A_t-\overline{A})(B_t-\overline{B}) \tag{8}$$

where $\overline{A}$ or $\overline{B}$ is the average between control residual value and low temperature/compound treated value for each residue. The covariance of any residue itself equals to the variance of each residue in response to temperature shift or compound treatment. The variance value of each residue was mapped on cryo-EM structures of CFTR by using Pymol to validate the both the local and long range covariance information in the Var-C map.

Figure 7G:
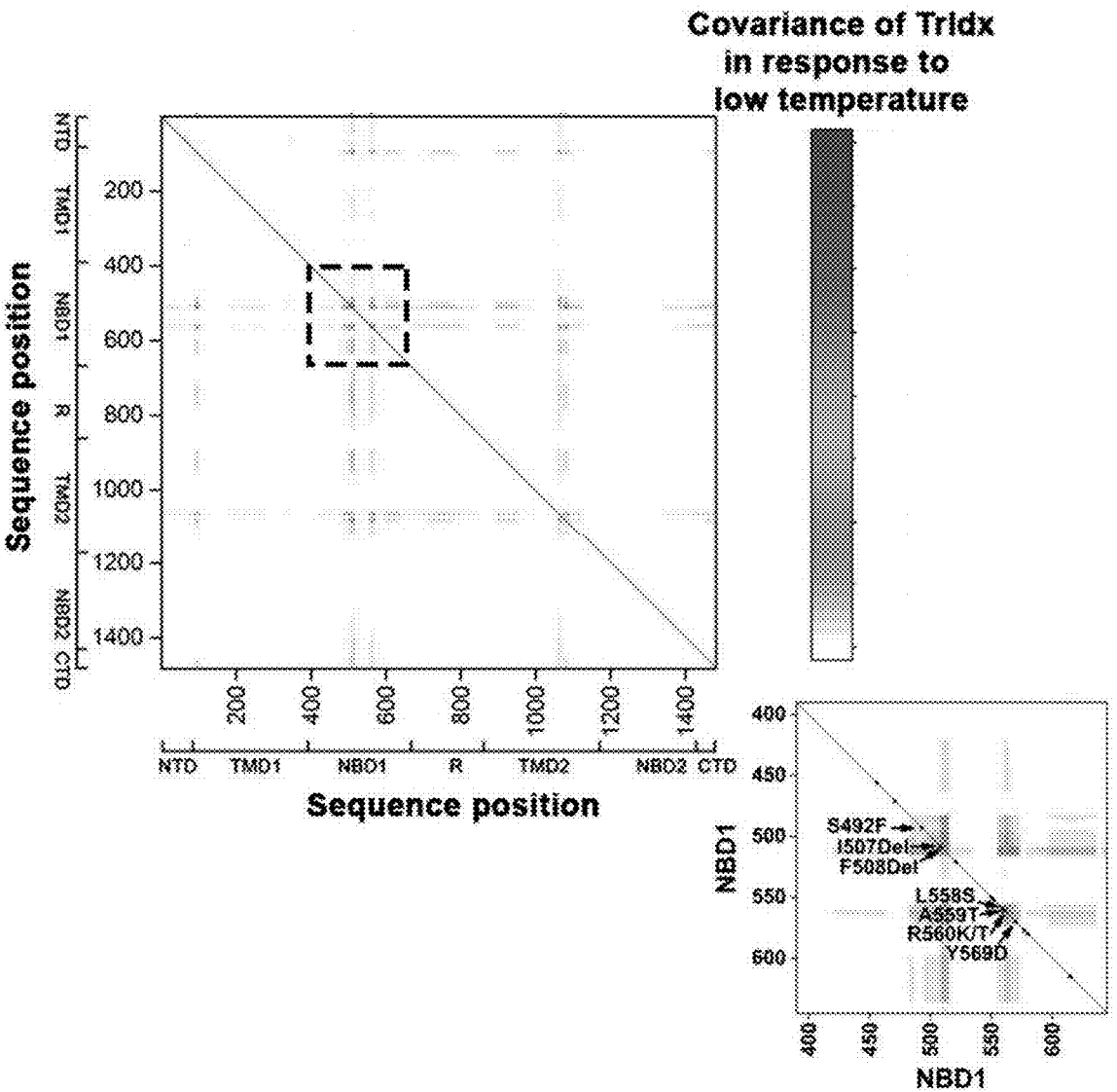
Figure 7H:
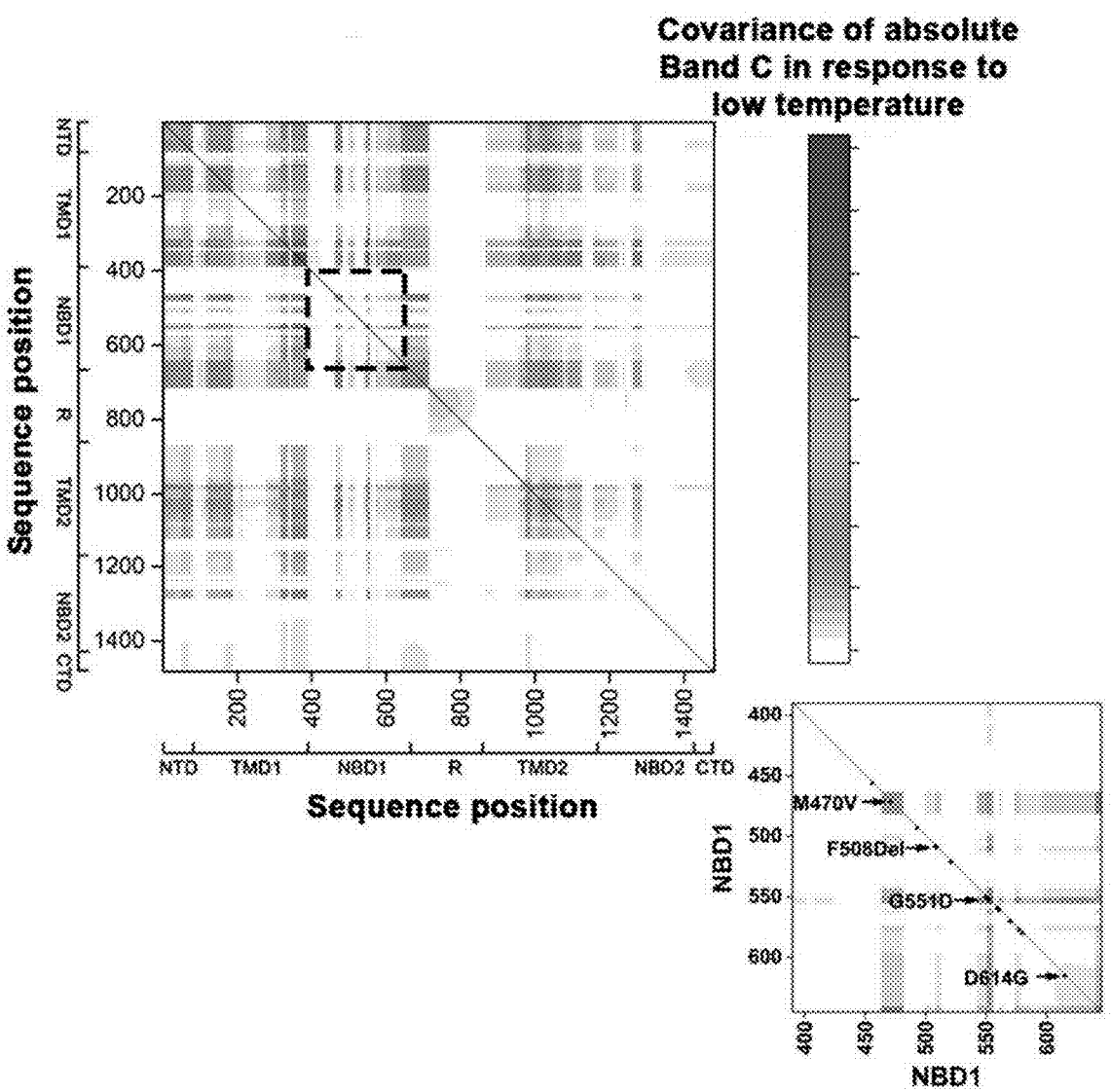
Figure 7I:
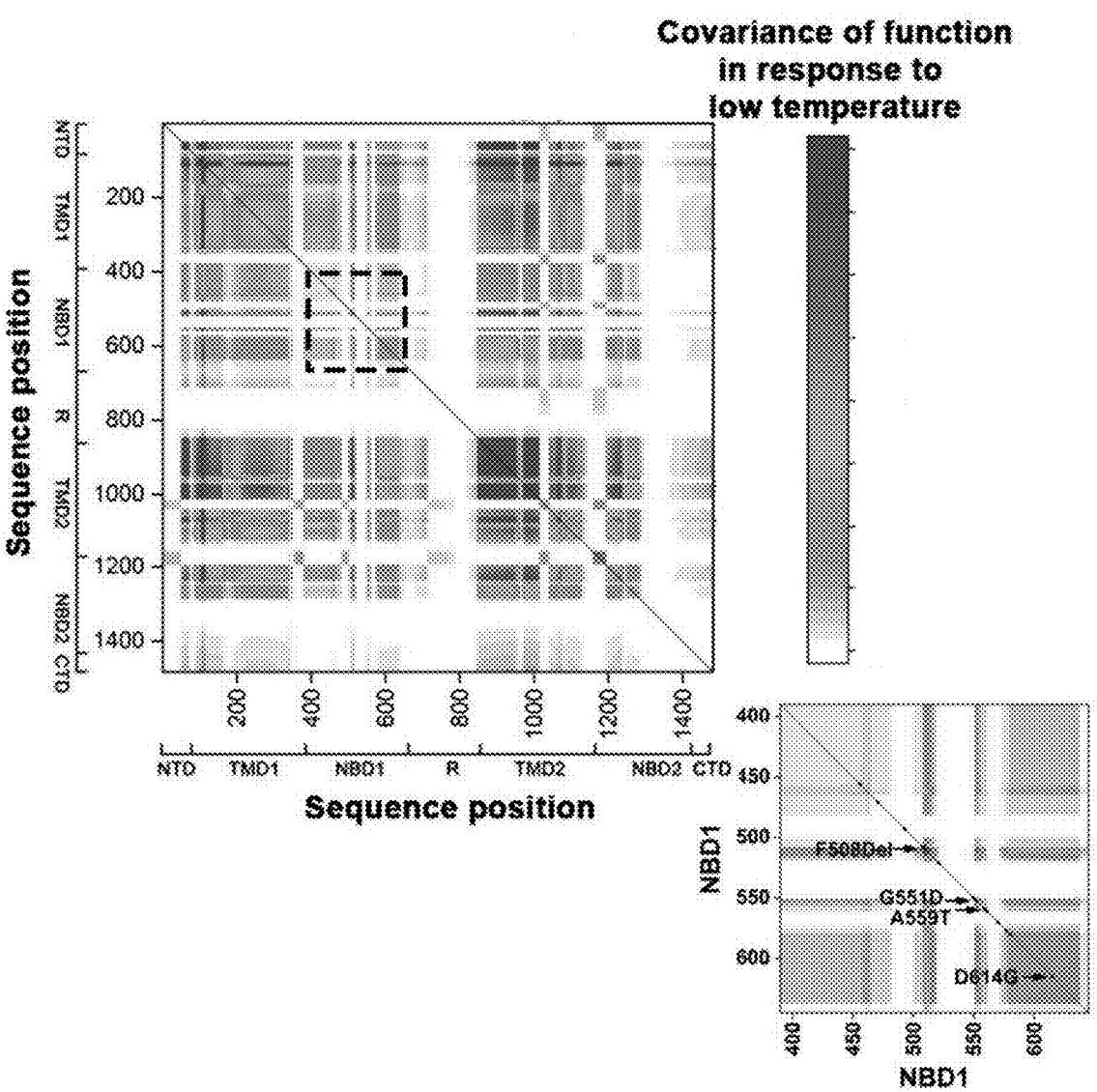
Figure 7J:
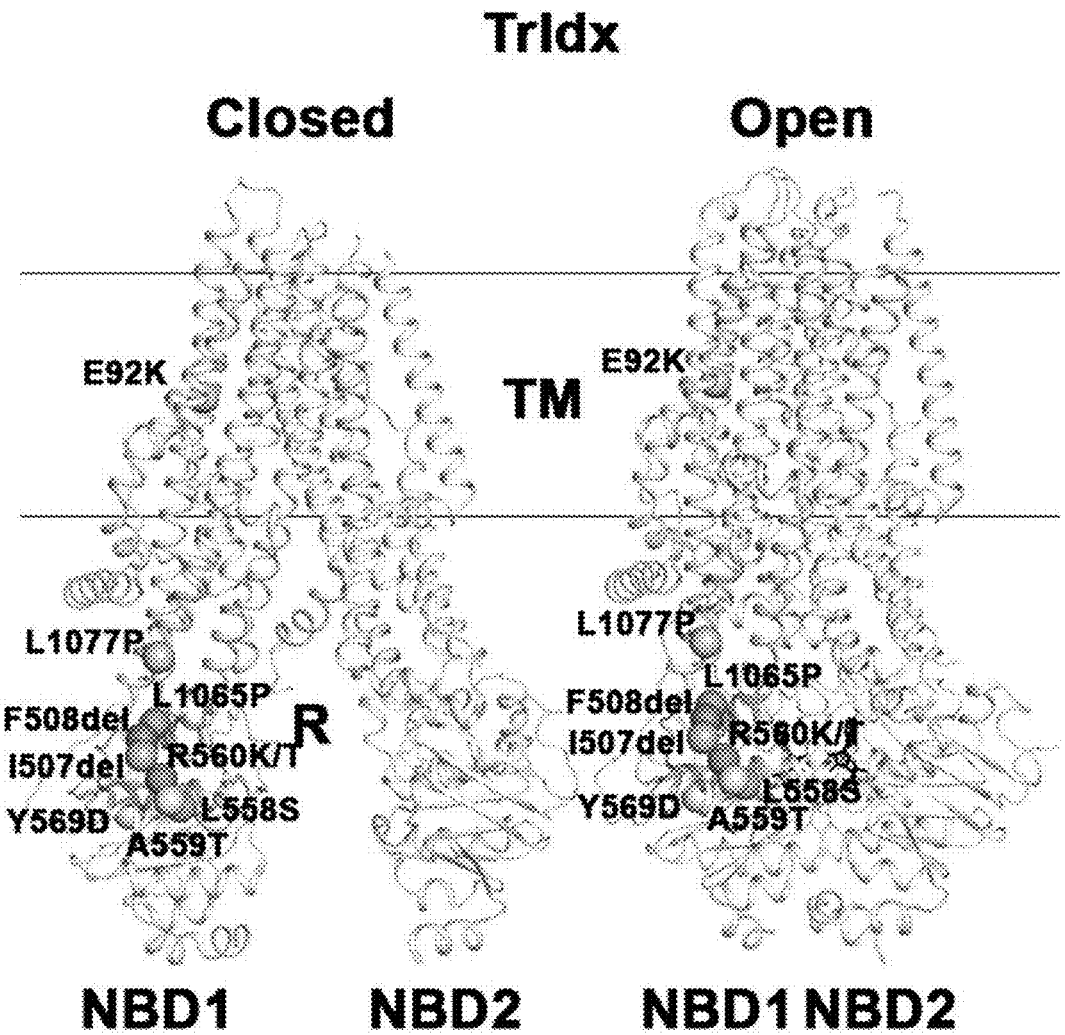
FIGS. 7J, 7K, 7L shows the value of the diagonal of the Var-C maps (i.e. the variance of each residue in response to low temperature) mapped on the CFTR structures at closed or open states to functionize the structure to understand the mechanism for the correction of TrIdx, absolute Band C, and function respectively in response to low temperature. The color scale is the same to that shown in FIGS. 7G, 7H, and 7I.
Figure 7K:
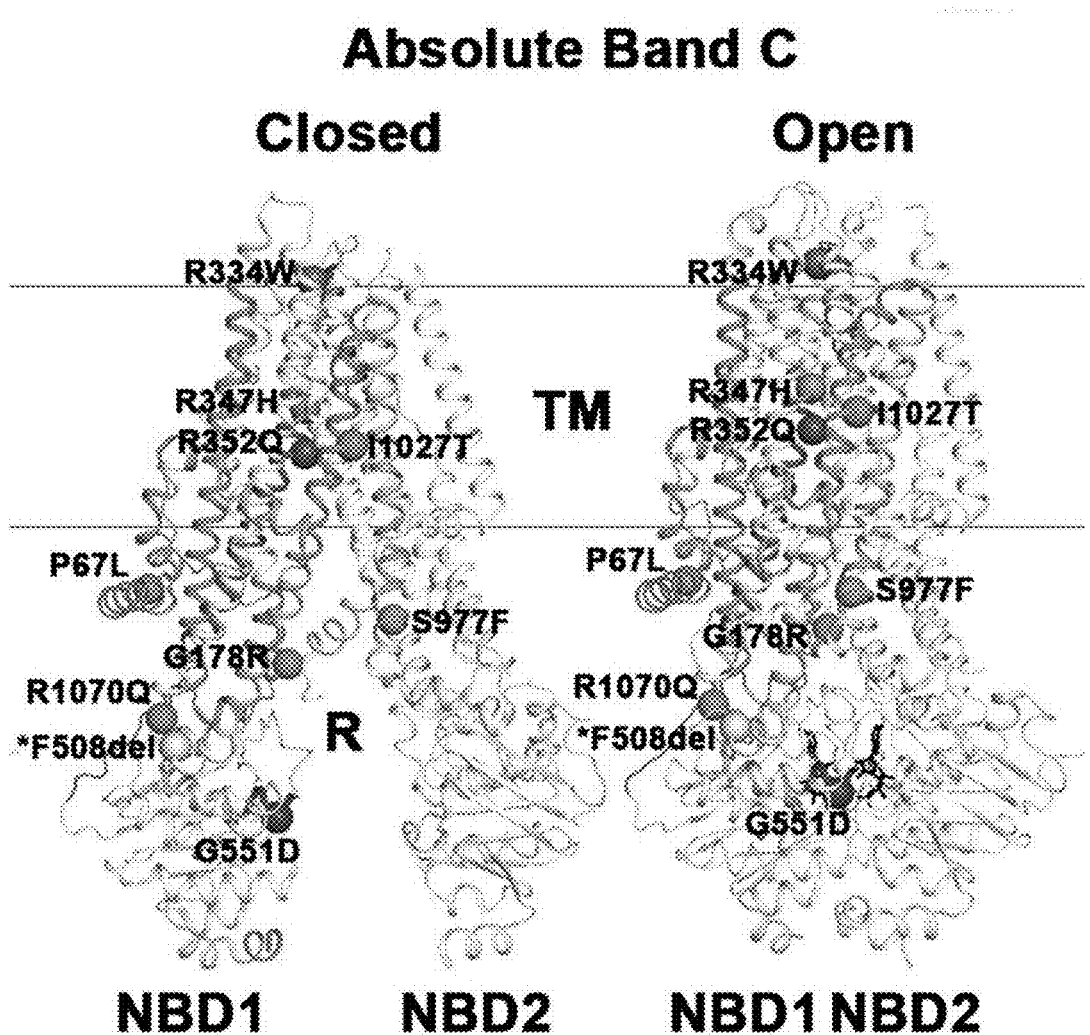
Figure 7L:
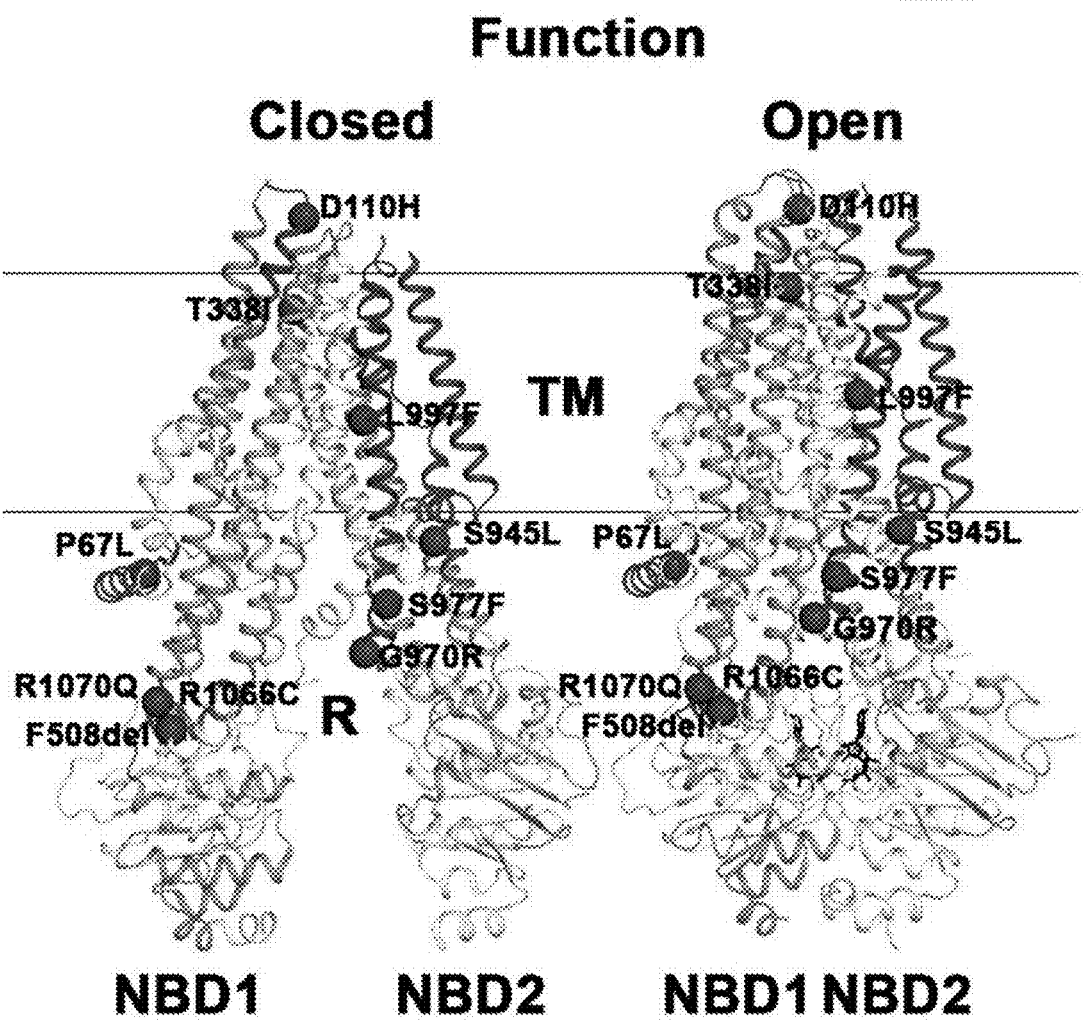

To generate the Var-C map describing of the role of each residue relative to other residues in the fold contributing to temperature correction, the highest confidence prediction from the phenotype landscape for each residue was used (FIGS. 7D-F). We hypothesized that if two residues respond to low temperature similarly, they might be close in the 3D structure and/or contribute to an allosteric conformational change trajectory that restores CFTR function. The value off the diagonal of Var-C map represents the covariance value of any pairwise combination of residues along the entire polypeptide chain in response to low temperature for TrIdx (FIG. 7G), absolute band C (FIG. 7H) and function (FIG. 7I). The value along the diagonal represents the covariance with the residue itself, in other words, the variance of each residue in response to the low temperature shift. The Var-C map of NBD1 domain harboring F508del is zoomed in to show the details of temperature correction. To validate local and long-range covariance interactions on the structure of CFTR, the diagonal values in the Var-C maps (i.e., the variance of each residue in response to low temperature) were mapped onto CFTR cryo-EM structures in both the dephosphorylated/ATP-free (closed) and phosphorylated/ATP-bound (open) conformations (FIGS. 7J-L) to 'functionalize' the structures to quantitatively define predicted structural responses underlying the inter-residue covariance in response to low temperature for TrIdx (FIG. 7J), absolute band C (FIG. 7K) and function (FIG. 7L).

The TrIdx Var-C map suggests that the TrIdx correction by low temperature is largely driven by the covariance of three fragments separated along the primary sequence. Two of them are located in NBD1 domain including one fragment mainly reported by F508del and one fragment encompassing the CFTR di-acidic ER-exit code (Y563-KDAD) reported by L558S, A559T, R560K/T and Y569D required for coupling to the COPII export machinery (FIG. 7G, insert). Another fragment is at the TMD2 domain in the intracellular loop 4 (ICL4) region in TMD2 reported by L1063P and L1077P (FIG. 7G). Functionalized structure mapping shows that these three fragments cluster together forming a core with F508 fragment linking ICL4 in TMD2 to the di-acidic code in NBD1 for COPII recognition to exit ER (FIG. 7J), validating both the local and long-range SCV relationships quantitated in the Var-C map (FIG. 7J). This result suggests that there is a temperature-sensitive 'SCV thermodynamic core' centered by F508del with thermodynamic problem, which impacts the majority of the CF patients and can be corrected by low temperature.

The improvement of TrIdx of F508del by low temperature (going from 3% to 11% of WT in response to temperature shift) (FIG. 7H and 7K, light green) is less than many other variants (FIG. 7H and 7K, green-cyan-blue) given the very low basal amount of F508del at 37° C. (FIG. 7B). However, channel function correction of F508del is very high (going from 0% to 51% of WT in response to temperature shift) (FIG. 7I and 7L, dark blue), indicating low temperature not only increases the absolute amount of F508del on the cell membrane, but also generates a fold that contributes significantly to F508del channel function at 27° C. Strikingly, besides the high function correction for the critical F508del 'SCV thermodynamic core', another region that is highly responsive for function is the transmembrane (TM) region at the NBD2 side (referred as TM (NBD2-side) hereafter) (FIG. 7L, blue region). This region has been shown recently as Ivacaftor binding site to regulate the channel gating properties. Our result shows that these structural dynamics critical for channel gating potentiated by Ivacaftor could also be managed by low temperature, indicating that thermodynamics is also important for CF activity at the cell membrane. Consistent with this, 27° C. correction is reversed by returning to 37° C. in response to its thermodynamic destabilization at the surface and downregulation by lysosomal degradation pathways reflecting a rapid reversal of temperature-stabilized SCV relationships. Thus, while low temperature stabilizes the critical F508del 'SCV thermodynamic core' for folding to export, the exported folded state remains thermodynamically unstable suggesting that SCV can capture the dynamic flux in thermodynamic properties of the fold reflecting its temporal intra- and inter-domain SCV relationships contributing to function.

To understand from therapeutic perspective what is needed to restore native CFTR function revealed by temperature sensitivity of the fold in the CF patient in the clinic, we utilized 59 variants distributed across the CFTR sequence that have been characterized for function responses to Ivacaftor (a potentiator of cell surface localized CFTR), Lumacaftor (a putative 'corrector' of ER export) and the combination of Ivacaftor and Lumacaftor (also named as Orkambi). Like temperature shift experiments, these are positioned in sequence-function SCV space by plotting their variant residue positions relative to full length CFTR on the x-axis, their residual channel function relative to WT on the y-axis, and their channel function when challenged by the clinically approved therapeutics Lumacaftor, Ivacaftor, and a combination of Ivacaftor/Lumacaftor (Orkambi) (referred to herein as Combo) on the z-axis. By analyzing the SCV relationships of the sparse variants connecting the functional values to sequence positions we can define their molecular variograms that describes the overall spatial variance features of the data. GPR-ML reveals that the spatial variance of CFTR function in the presence of compound(s) treatment increases with distance defined by the residual function with sequence position, a result that is consistent with a previous report showing a strong correlation between the residual function of a variant and their response to CFTR modulators.

Figure 8A:
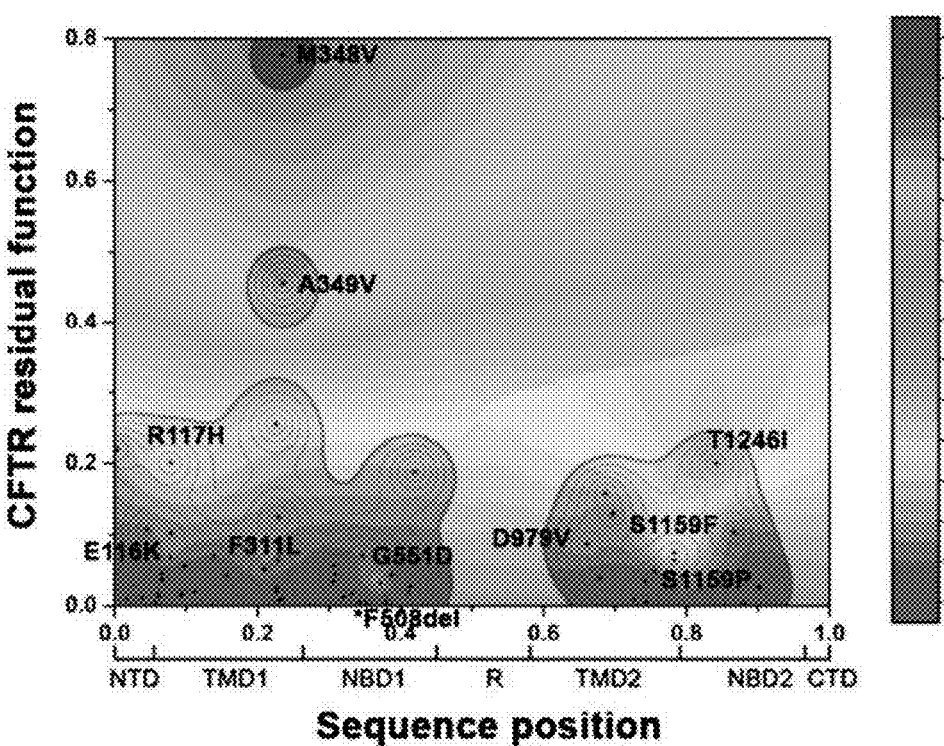
FIGS. 8A, 8B, and 8C show phenotype landscapes to link sequence position of CF variants to the residual function (y-axis) to the response value for Ivacaftor, Lumacaftor, and combination of Ivacaftor/Lumacaftor (Combo) respectively. Top 10 responsive variants are labeled according to their residue position. If F508del is not in the top 10 response list, it is labeled as *F508del.
Figure 8B:
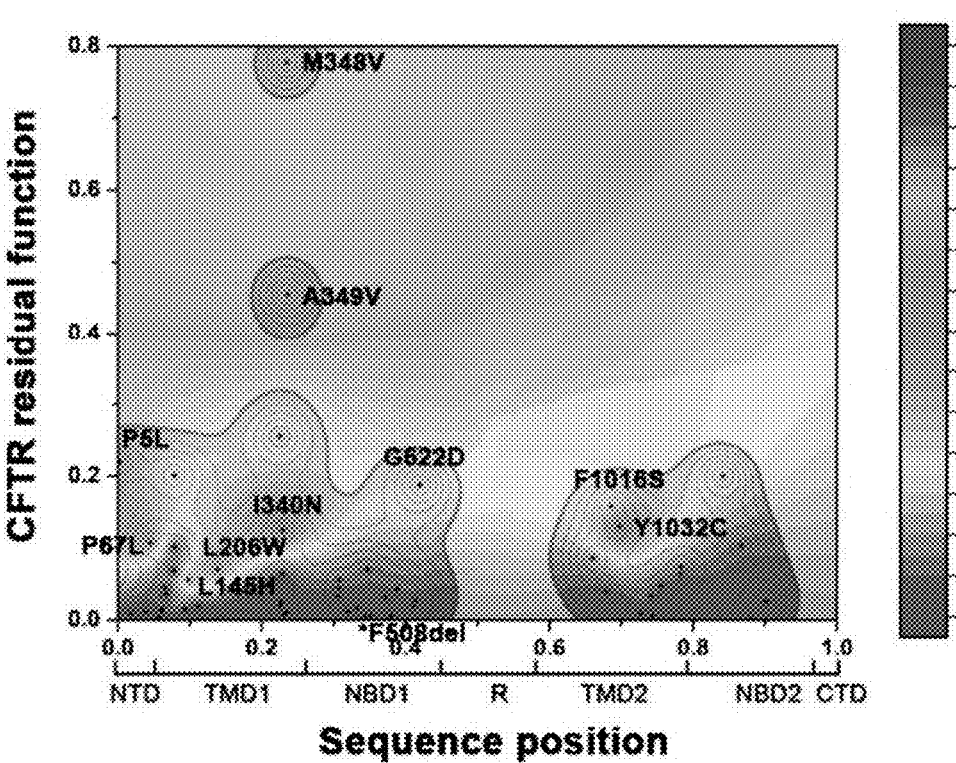

To define the high-definition of sequence-function space in the context of different compound treatments, we used VSP to build the phenotype landscapes (FIGS. 8A-C) for the entire CFTR polypeptide by interpolating the missing values based on the molecular variograms. The landscapes achieve high accuracy in predicting compound(s) response as validated by the leave-one-out cross-validation with Pearson's r=0.94 for Ivacaftor landscape (FIG. 8A), Pearson's r=0.74 for Lumacaftor landscape (FIG. 8B) and Pearson's r=0.78 for Combo landscape (FIG. 8C) between the measured and predicted variant function. The three phenotype landscapes show dramatically different responses to therapeutics. Lumacaftor and Combo landscapes show more correctability for variants with low residual function (below ~20% of WT) (FIGS. 8A-8C, y<~0.2, yellow-green in FIG. 8B and FIG. 8C vs red-orange in FIG. 8A). Variants with very low residual function are thought to have folding defects that limit ER exit and potentially contribute to ER degradation that can be targeted by Lumacaftor but not Ivacaftor. Furthermore, multiple localized areas of the fold are found to respond to the modulators differentially. For example, a highly corrected region by Ivacaftor occurs near the boundary between TMD2 and NBD2 that is mainly contributed by S1159F/P and T1246I, but is poorly corrected by Lumacaftor (FIG. 8A vs FIG. 8B). On the other hand, regions that are highly responsive to Lumacaftor, including regions located in NTD (mainly contributed by P5L and P67L) and TMD1 domain (mainly contributed by L145H, L206W and I340N), as well as TMD2 domain mainly contributed by F1016S and Y1032C are not sensitive to Ivacaftor alone (FIG. 8B vs FIG. 8C).

Figure 8C:
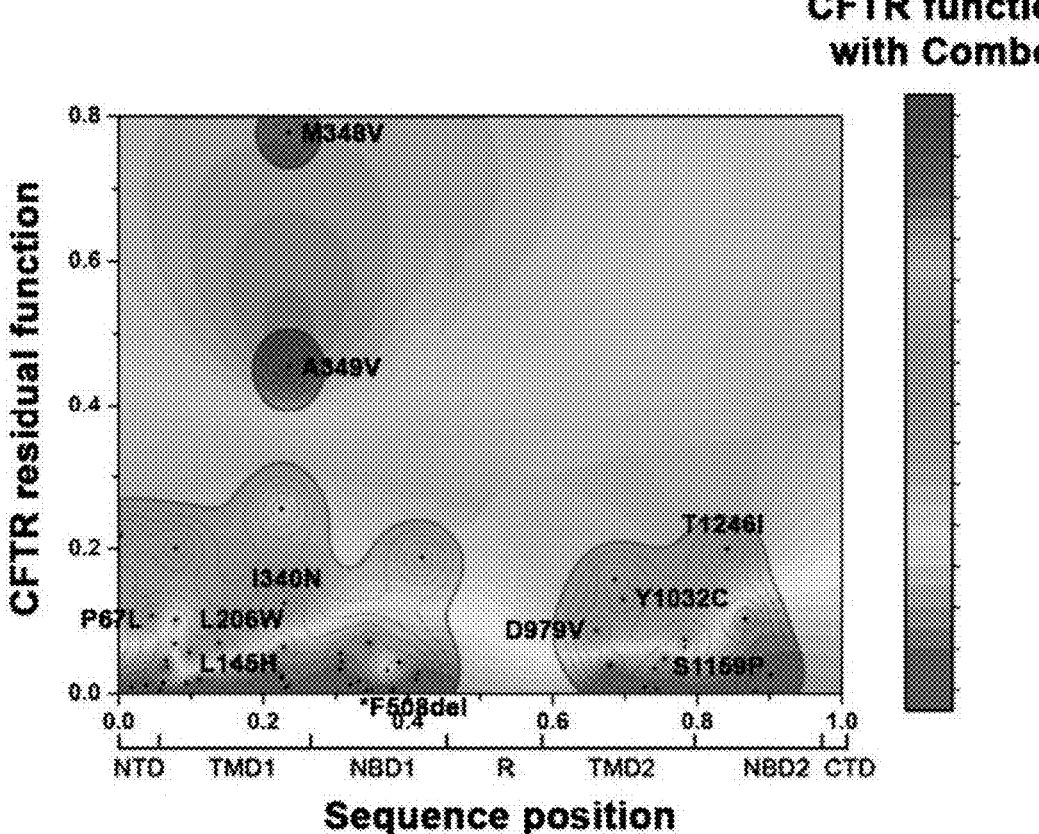
Figure 8D:
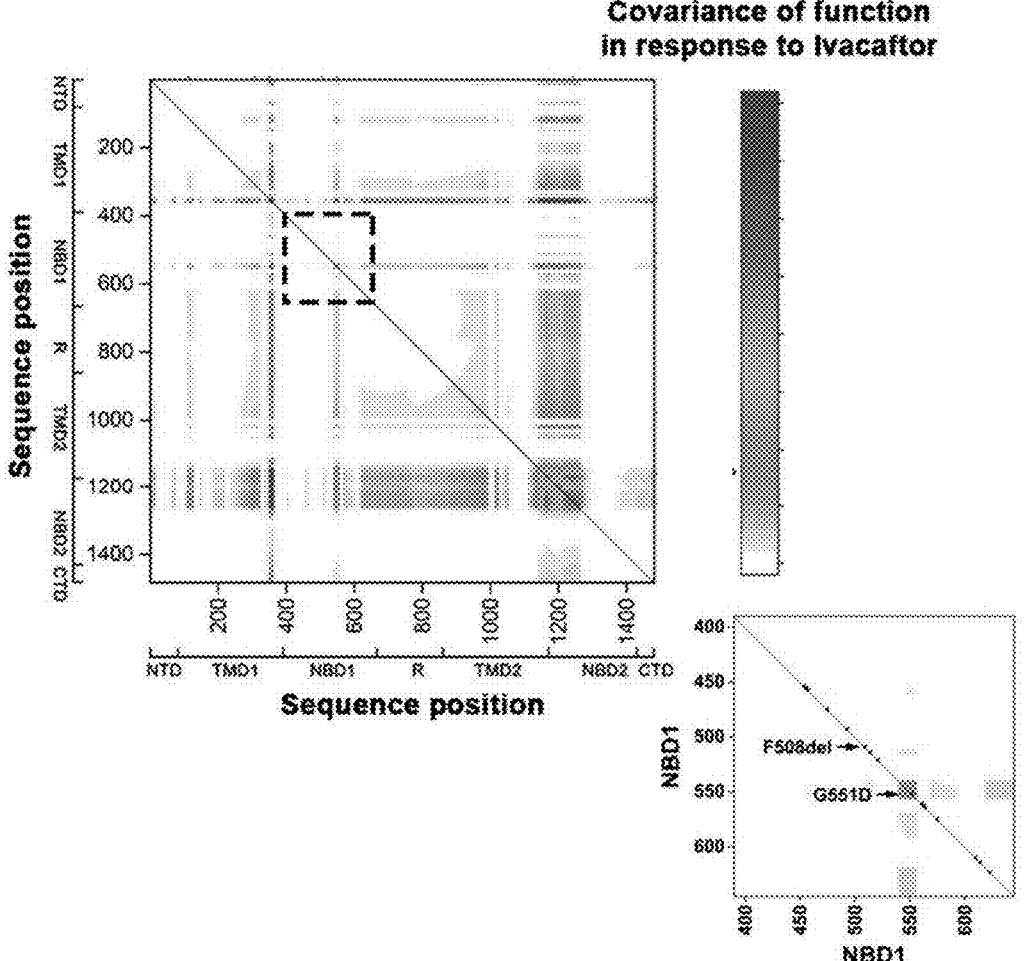

To capture both the local and long-range inter-residue relationships, we generated Var-C maps (FIGS. 8D-F) based on the covariance of pairwise residues in response to compound treatment derived from the SCV landscape (FIGS. 8A-C). Here, the value off the diagonal of Var-C map represents the covariance value of any pairwise combination of residues along the entire polypeptide chain in response to Ivacaftor (FIG. 8A), Lumacaftor (FIG. 8B) and Combo (FIG. 8C). The top 10 responsive variants under each treatment are labeled. Intriguingly, the most common CF variant F508del (*F508del) is not in the top 10 list of the responsive variants for any compound condition. The Var-C map of NBD1 domain harboring F508del is zoomed in to show the details of correction. The Var-C maps (FIGS. 8D-F) reveal differential connectivity of the residues driving functional correction by different compounds. The diagonal values in the Var-C maps (i.e., the variance of each residue in response to compounds) (FIGS. 8D-F) was mapped onto CFTR cryo-EM structures to validate local and long-range covariance association (FIGS. 8G-I).

The Ivacaftor Var-C map (FIG. 8D) demonstrates that Ivacaftor correction is mainly driven by the cooperative effect of multiple regions along the primary sequence including regions in TMD1 domain (reported by E116K/R117H and F311L/M348V/A349V), in NBD1 domain (reported by G551D) (FIG. 8D, insert), in TMD2 domain (reported by D979V and S1189F/P) and in NBD2 domain (reported by T1246I). Strikingly, mapping the predicted value onto CFTR functionalized structure (FIG. 8G) reveals a structural pathway connecting the ATP hydrolysis site to the channel region to the extracellular loop region, validating the high covariance of these regions observed in Var-C map (FIG. 8D). It is apparent that TM-NBD2 side is more corrected than TM-NBD1 side (FIG. 8G), consistent with the cryo-EM structure of CFTR-Ivacaftor complex where TM at NBD2 side is driving the correction. Furthermore, the high responsive regions contributed by F311L, D979V and S1159F/P are adjacent to the Ivacaftor binding site. These linked SCV relationships defining the functionalized structure of CFTR suggest that Ivacaftor functions via allosteric mechanisms to mediate channel gating properties to correct CFTR function.

Figure 8E:
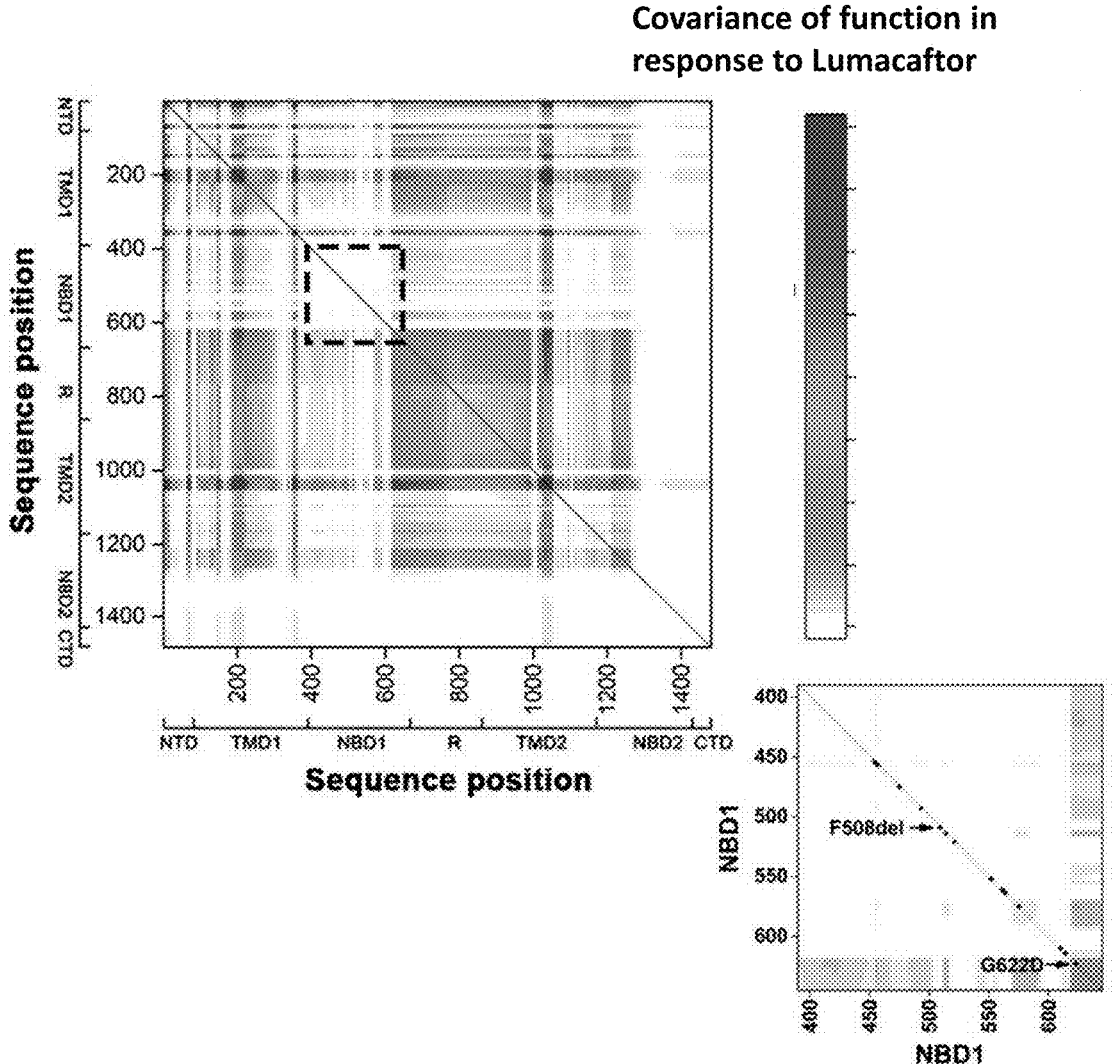
Figure 8F:
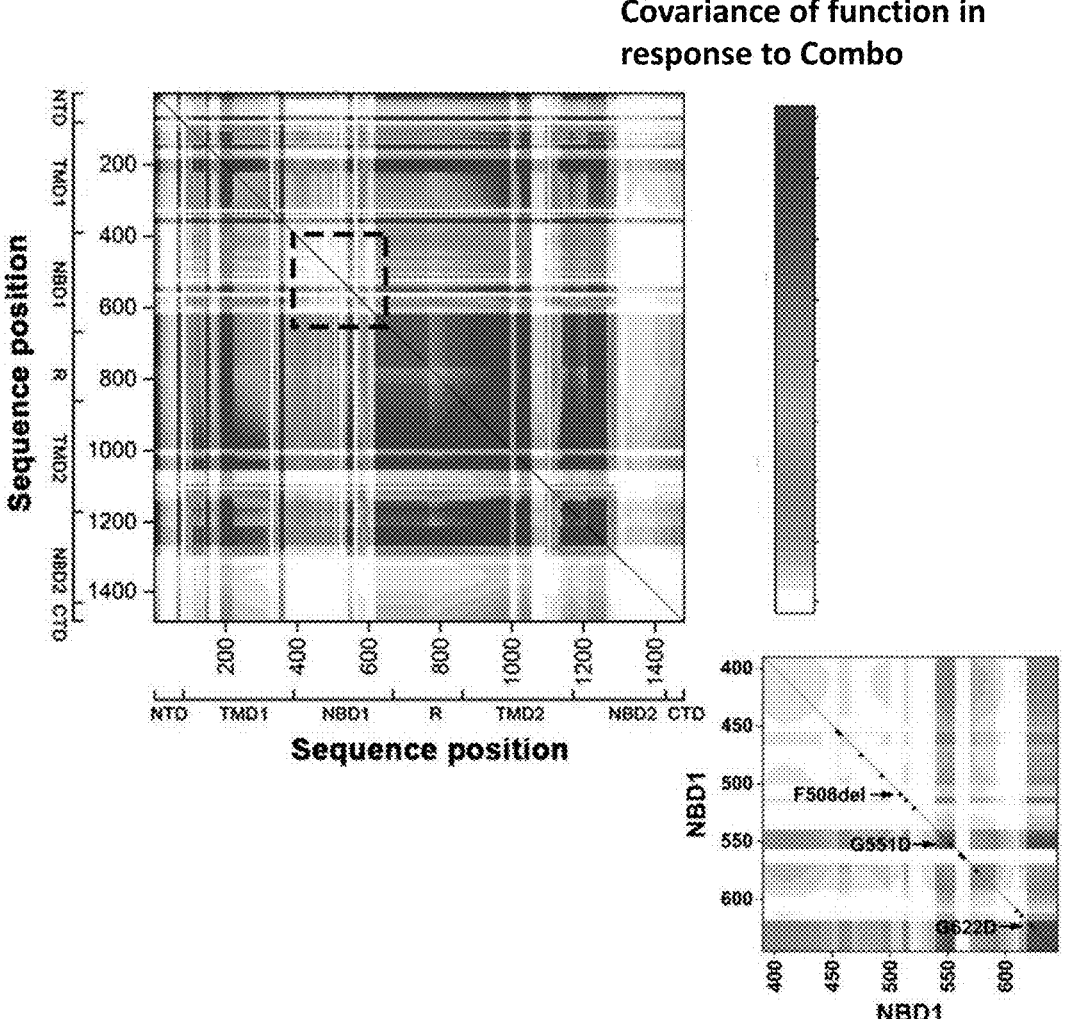
Figure 8G:
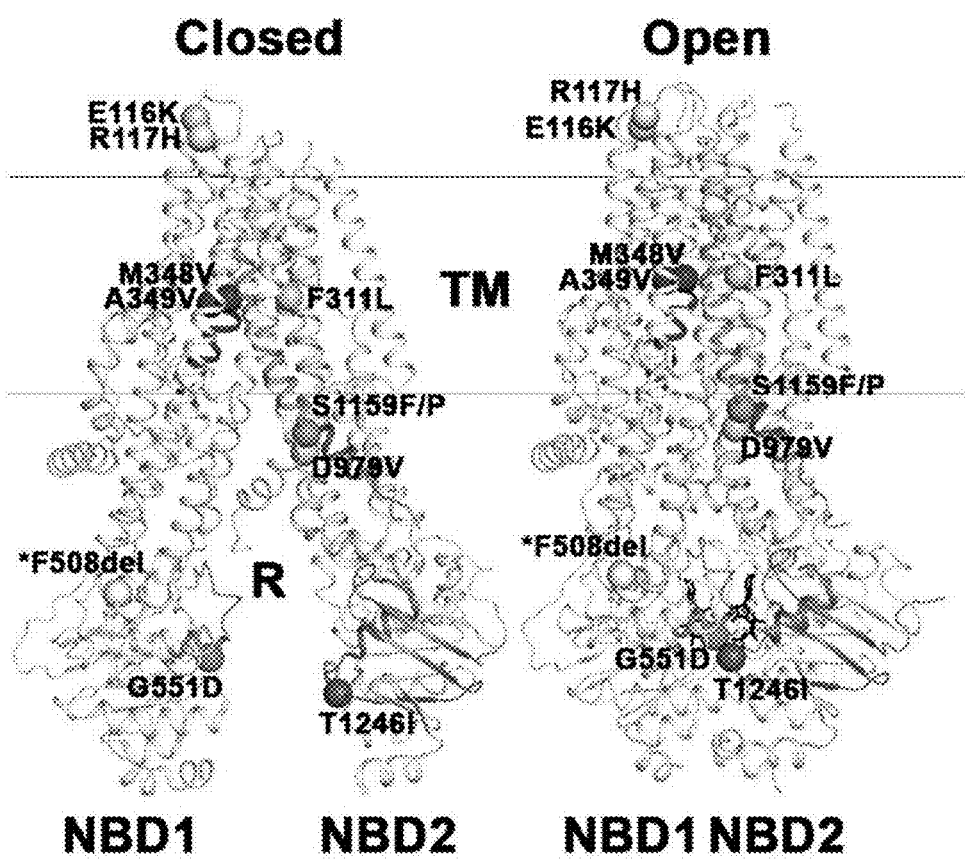
FIGS. 8G, 8H, and 8I show the diagonal value of the Var-C maps of FIGS. 8D, 8E, and 8F respectively projected to CFTR cryo-EM structures.
Figure 8H:
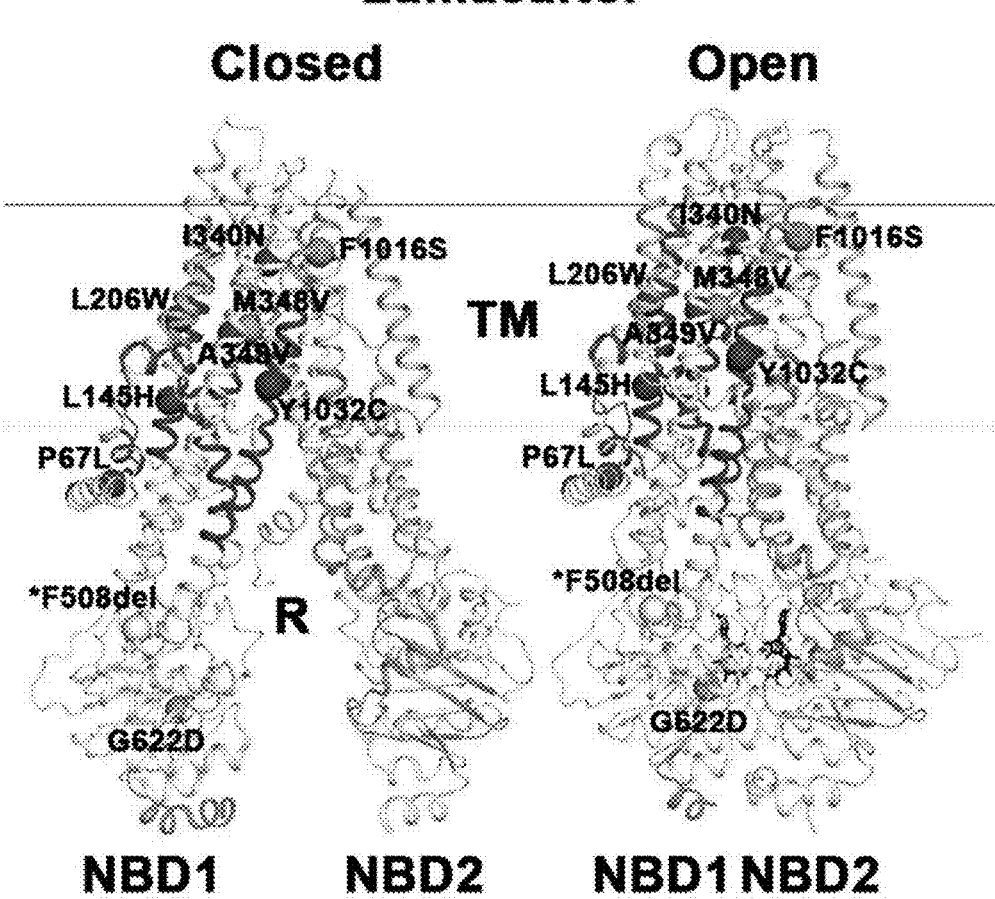
Figure 8I:
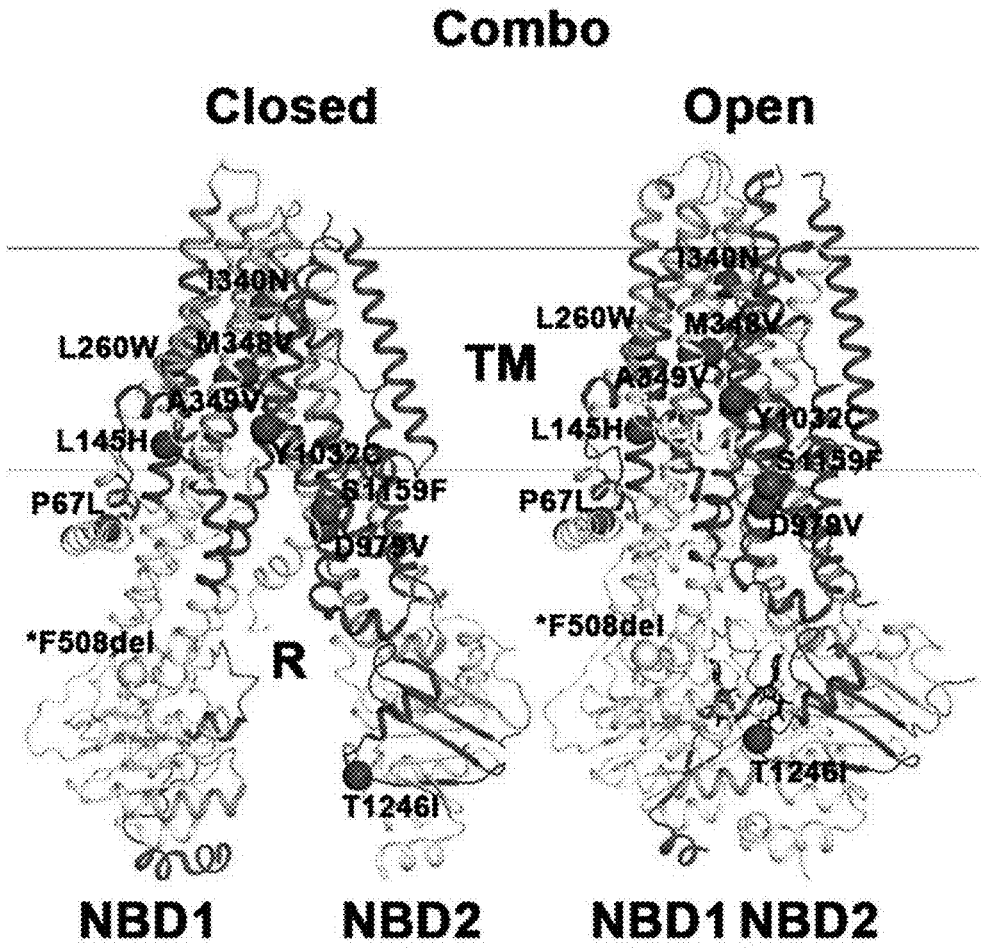

In contrast to Ivacaftor, the Lumacaftor Var-C map suggests high covariance connectivity between strong response regions that are distinct from Ivacaftor (FIG. 8E, blue regions). Remarkably, although they are spread along the primary sequence encompassing NTD, TMD1 and TMD2 domains, SCV modeling shows they are clustered in the CFTR functional-structure (FIG. 8E and 8H, blue regions). These results validate the covariance information derived from the primary sequence and function response based on GPR-ML based SCV analyses. The Lumacaftor Var-C maps and their functionalized structures suggest that Lumacaftor mainly targets the TM region at the NBD1 side (referred as the TM (NBD1-side) hereafter), including NTD, parts of TMD1 and a small region in TMD2 (FIG. 8E and 8H, blue regions). This result is consistent with a previous report showing the truncated NTD-TMD1 fragment can be stabilized by Lumacaftor. Given that the TMD2-NBD2 fragment alone cannot be stabilized by Lumacaftor, the moderate response observed for the TM region at the NBD2 side (referred as the TM (NBD2-side) hereafter) (FIG. 8E and 8H, green regions connecting TM to NBD2) is likely allosterically transduced from its stabilization effect in the TM (NBD1-side). This result suggests distinct binding site(s) and molecular mechanisms of Lumacaftor than Ivacaftor. Strikingly, the 'SCV thermodynamic core' (i.e. ICL4-NBD1-diacidic code centered on F508del) that can be corrected by low temperature has a very modest response to Lumacaftor (FIG. 8E, insert; FIG. 8H), indicating a very peripheral impact of Lumacaftor on F508del in most of the CF patients. An exception in NBD1 domain that is responsive to Lumacaftor is the C-terminal region in NBD1 domain reported by G622D (FIG. 8E, insert; FIG. 8H). This result is consistent with the chemical shift of this region observed in the titration of Lumacaftor on NBD1 domain using NMR, suggesting that besides the highly responsive TM (NBD1-side) region, the C-terminal of NBD1 domain could serve another potential interaction site for Lumacaftor.

The distinct response trajectories to Ivacaftor and Lumacaftor can be simultaneously targeted by the Combo treatment (FIGS. 8F and 8G, right panel) revealing the additive/synergistic effect of the drugs. For example, the TM (NBD2-side) shows a greater response to the Combo when compared to Ivacaftor or Lumacaftor alone, suggesting the TM (NBD2-side) may allosterically couple trafficking with gating. Because the correction of the most common F508del variant is very limited in response to all the modulator treatments (FIGS. 8D-F, insert; FIGS. 8G-I, *F508del), we increased the resolution of the Var-C map for those variants that have low residual function (0~10% of WT) by building the response phenotype landscapes and Var-C maps based on the $\log^{10}$ transformation of the data (r=0.96 for Ivacaftor, r=0.85 for Lumacaftor, r=0.85 for Combo) compared to landscapes using the linear form of the dataset (FIGS. 8A-C) The $\log^{10}$ landscapes show that Lumacaftor and Combo treatment only weakly correct the variants with residual function below 1% of WT. These high-resolution Var-C maps and their functionalized structures in response to Lumacaftor now capture a modest effect of the 'SCV thermodynamic core' connecting the strong impact of the TM (NBD1-side) to F508del through the interaction between ICL4 and NBD1, which is not present in the Ivacaftor response alone. Combo treatment brings a very modest global correction to NBD1 domain, except for a fragment contributed by R560, A561 and Y563 that includes the di-acidic ER exit code for coupling to COPII (Y563-KDAD). These results indicate that Combo treatment cannot correct the variants that are directly contributing to COPII recognition, residues that when mutated contribute to loss of export and accelerated CFTR degradation. Though the Var-C map illustrates the correction of F508del fold is increased in response to Combo treatment compared to either Ivacaftor or Lumacaftor alone, the modest correction (from residual function of 0.5% WT to 3% of WT in Combo treatment) demonstrates the impact of these modulators on F508del is peripheral and does not address the key problem defined by thermodynamic instability governed F508del that is driving disease uncoupling CFTR from COPII and leading to its degradation. Thus, SCV Var-C mapping quantitatively demonstrates based on the variation distributed in the CF population, which current drugs fail to impact the Achilles heel (i.e. the SCV thmodynamic core) of 90% disease affecting CF patients and point the way towards a cure. These results reinforce a conclusion that current therapeutics do not target the fold legitimately based on nature's design principles—hence accounting for their low and variable efficacy in clinical management of disease that is out of synchrony with 3.5 billion years of evolved SCV rules.

By linking human variants in the CF population through GPR-ML SCV and rigorously defining SCV states through Var-C mapping to define the intra- and inter-residue interactions dictating function, we are able to for the first time map the integrated molecular response of the entire CFTR fold to the environment (low temperature) and that induced by therapeutics (CFTR modulators). Strikingly, while temperature corrects the fundamental core of CFTR resulting in permissive function of its thermodynamically challenge fold distinctive of the NBD1, the peripheral impact of current therapeutic modulators, likely largely allosteric in design, provide fresh focus and suggest an urgent need to develop therapeutic approaches that target the F508del SCV core, a rate-limiting ER trafficking thermodynamic tolerance setpoint that is captured and corrected by low temperature shift. Learning how this SCV core is shaped and evolved through nature in terms of its stability[35] will be the key to management of CF disease and likely many genetic diseases whose fold impacts its fundamental ability to achieve a functional state following translation by the ribosome—whether in the ER or the cytosol. Our SCV analysis is validated by the numerous biochemical, biophysical and structural studies on isolated NBD1 and in molecular dynamic simulations that suggest the inner core defined by SCV relationships is key to the operation of CFTR for ER export- and function and stability at the surface. The critical SCV defined thermodynamic core is the critical energetically unfavorable state that serves as the key nidus in disease onset and progression and its defective tips the balance between export by COPII via the di-acidic code and degradation by the ERAD UPS system. While Low temperature is able to partially correct F508del, it is restoration of function achieves a level of 50% which is more than amble to cure CF patients if achieved through chemical biology. This points to the power of SCV to point to the underlying principle driving any disease. VSP and Var-C using only a sparse collection variants found in the population when functionalized from the point of view of clinical data, i.e., the human model, is projected to be game-changing approach to drug discovery, providing a robust high-throughput platform to see the endpoint before intervention in the human as the SCV paradigm is built on the human population in the context of its genetic diversity.

Figure 6C:
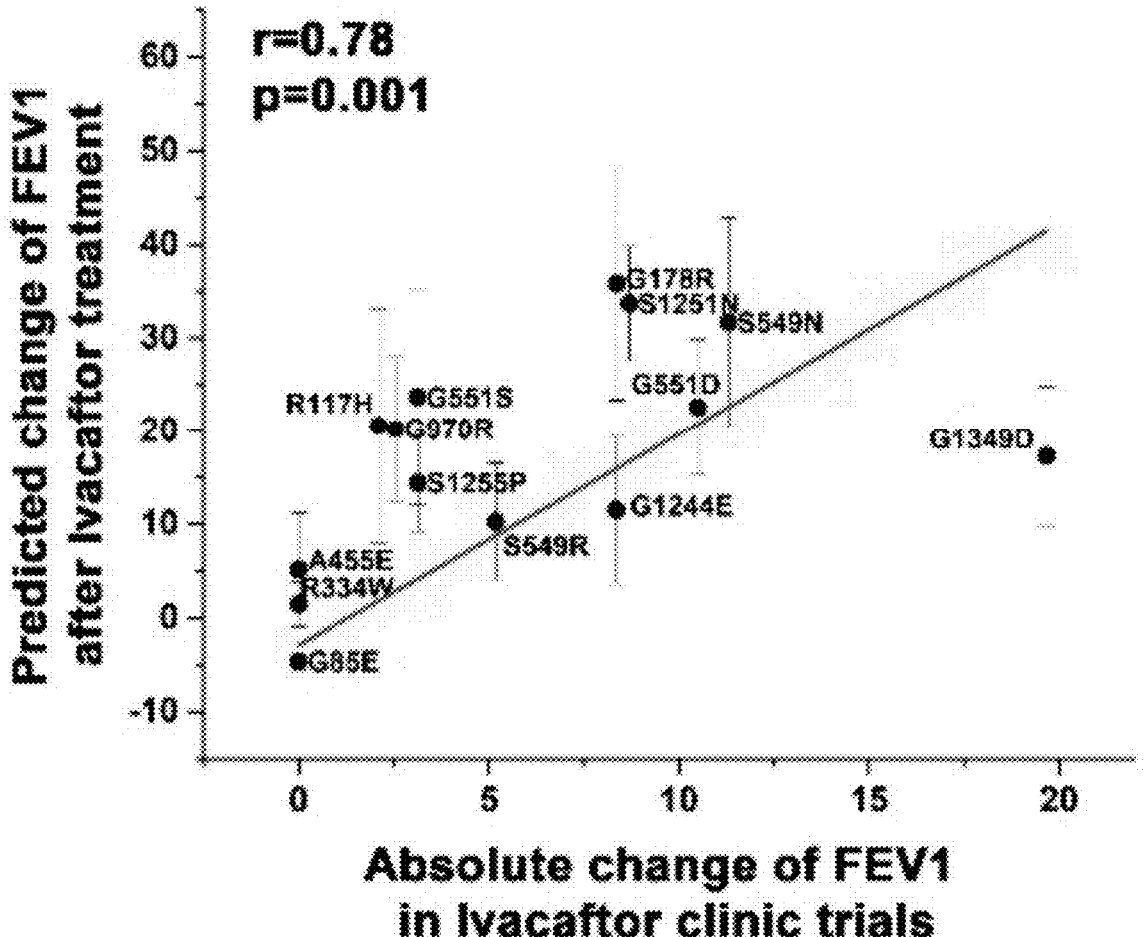
FIG 6C is a plot showing validation of predicted FEV1 correction after Ivacaftor treatment with clinic trial results. The standard deviation of the prediction is shown as error bar.
Figure 6D:
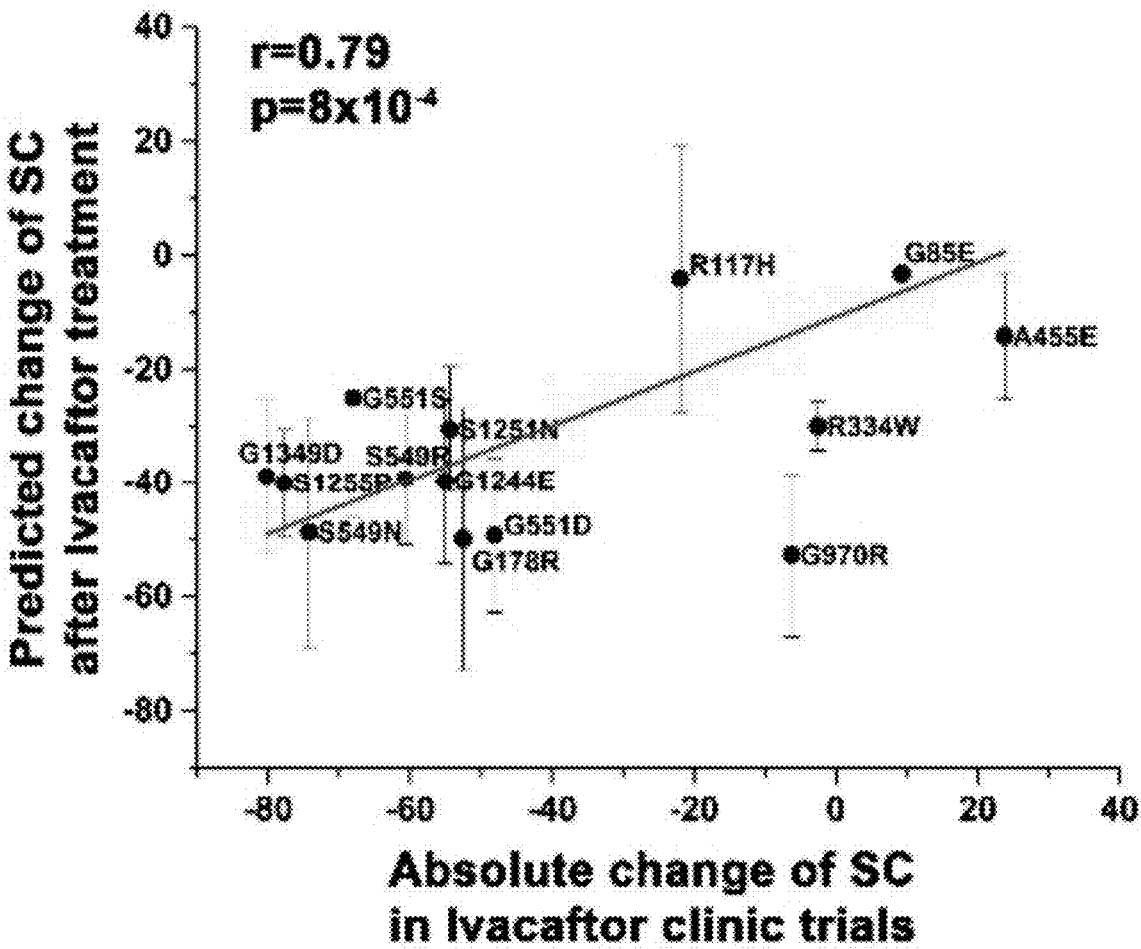
FIG 6D is a plot showing validation of predicted sweat chloride (SC) correction after Ivacaftor treatment with clinic trial results. The standard deviation of the prediction is shown as error bar.

We used VSP to learn the value of cell-based (bench) measurements as input to predict clinical measures (bedside) as output across the entire CF variant population (FIGS. 6A-B; top left quadrant). Such relationships present a fundamental challenge in translational medicine where most cell-based and animal models fail to predict clinical outcome, leading to substantial loss of time and financial resources. While all VSP bench to bedside predictions show weak, but statistically significant correlation (FIG. 6A-B; top left quadrant), the strongest correlation is seen when we use ClCon as the y-axis to predict SC (FIG. 6A-B; panel 17, Pearson's r=0.63, p-value=$3 \times 10^{-8}$). Thus, cell-based ClCon measurements largely captures SC responses recovered from the patient population, a prediction validated in the clinic for the prominent G551D and F508del variants. Indeed, by using the spatial relationships linking bench to bedside, we can now examine the clinical response of Ivacaftor for all patients based on cell-based ClCon measurements. Both FEV1 (FIG. 6C, Pearson's r-value=0.78, p-value=0.001) and SC (FIG. 6D, Pearson's r-value=0.79, p=$8 \times 10^{-4}$) responses predicted by VSP have strong statistical significance when correlated with clinic trial results, validating the utility of the VSP to serve as a guide to link cell-based models to clinical studies for therapeutic intervention with Ivacaftor.

Niemann-Pick C1 (NPC1) Example

Niemann-Pick C type 1 (NPC1) is a rare inherited autosomal recessive disorder caused by over 300 variants in the NPC1 gene. To understand the sequence-to-function-to-structure relationships contributing to NPC1 disease, we applied variation spatial profiling (VSP) to analyze the spatial-covariance (SCV) states of a sparse collection of NPC1 variants found in the population to generate a phenotype landscape that describes the function of individual variation across the entire NPC1 polypeptide sequence. Functional adaptive structures (FASTs) of NPC1 generated at atomic resolution by phenotype landscapes allow us to identify the critical structural features for NPC1 trafficking, cholesterol management and clinic presentation. The global changes in SCV spatial states in response to histone deacetylase inhibitors (HDACi) suggest an unanticipated level of plasticity of the NPC1 polypeptide fold for function, providing new insights into the role of HDAC in the cell and its potential application to precision management of biology and disease.

Pathogenic variation in polypeptides traversing the endomembrane system of eukaryotic cells give rise to disease that are largely a consequence of mismanagement of polypeptide stability, cellular location and/or function. NPC1 is a multi-membrane spanning protein that is translocated and folded in the endoplasmic reticulum (ER) and trafficked through the Golgi to late endosome (LE)/lysosome (LY) (LE/LY) compartments where it manages cellular cholesterol homeostasis. Defects in NPC1 lead to an autosomal recessive LE/LY cholesterol storage disease, Niemann-Pick C (NPC). The onset of disease is first triggered by loss-of-function in the central nervous system through progressive loss of Purkinje cells in the cerebellum and a rapid decline of neurological function. A majority of patients with NPC disease die before 25 years of age because of neurological complications.

NPC1 contains three luminal domains (SNLD1, MLD3 and CLD5) and three transmembrane domains (NTMD2, STMD4 and CTMD6) with 13 transmembrane helices (TM 1-13). NPC1 works with NPC2, a small soluble LE/LY localized cholesterol shuttle, to mediate cholesterol homeostasis in the cell. It has been shown that the middle luminal domain, MLD3, binds NPC2 to facilitates the transfer of cholesterol from NPC2 to the sterol binding site in the SNLD1 N-terminal luminal domain. A second sterol binding site is proposed in the sterol-sensing transmembrane domain, STMD4. How cholesterol is transferred from SNLD1 to STMD4 and then exported out of LE/LY remains unknown.

The NPC1$^{I1061T}$ mutation found in the C-terminal luminal domain (CLD5) contributes to 15~20% of NPC1 population in both homozygous (~5%) and heterozygous states harboring additional alleles. The I1061T variant is selected for ER-associated degradation resulting in deficient trafficking of NPC1 to LE/LY with the resultant accumulation of cholesterol. FDA-approved histone deacetylase inhibitors (HDACi) Vorinostat (SAHA) and Panobinostat (LBH589) have been shown to correct the I1061T phenotype by stabilizing the NPC1$^{I1061T}$ protein for export to the LE/LY where it contributes to improved cholesterol homeostasis. HDACi correct cholesterol storage in patient derived human fibroblast cells that express the homozygous NPC1$^{I1061T}$ mutation, in mouse embryo fibroblasts from a knock-in mouse model of NPC1$^{I1061T}$ and in Npc1$^{nmf164}$ mouse model that has NPC1D1005G mutation. In addition to NPC1$^{I1061T}$, more than 300 additional variants have been identified that are distributed across the polypeptide sequence and impact function in all domains triggering NPC1 disease. Our understanding of their contribution to age of disease onset, and clinical presentation/progression remains largely unknown. Surprisingly, given the diversity of variation responsible for disease, we recently found HDACi corrected the cholesterol storage defect for nearly 85% of known NPC1 variants. What remains unknown is which step(s) (i.e., protein stability, trafficking and/or the function in the LE/LY) are targeted by HDACi for each variant.

To generate a more complete understanding of variation contributing to disease in the Niemann-Pick C1 population, we have applied Variation Spatial Profiling (VSP), a new physics-based computational approach that captures and predicts polypeptide function in the individual in the context of the collective of variants found in the worldwide NPC1 population. As described above, VSP utilizes Gaussian process logic to assess spatial covariance (SCV) relationships among a sparse collection of fiduciary NPC1 variants. These spatial relationships allow us to generate phenotype landscapes for prediction of atomic resolution functional-adaptive-structure (FAST) states for the entire polypeptide chain in the context of complex physiological environments found in the different cell and tissue specific environments. Applying our VSP strategy, we have now uncovered a key role for the CLD5 and MLD3 handshake in mediating the trafficking of NPC1 from the ER, identified an unexpected role of CLD5 and CTMD6 in coordinating cholesterol export from the LE/LY, and demonstrated a region in CLD5 regulating age of neurological disease onset. Strikingly, examining the impact HDACi to correct the modular SCV relationships responsible for the genotype to phenotype transformation driving cholesterol homeostasis for the entire polypeptide fold suggests a critical role for acetylation/deacetyation balance in the differential management of the fold stability, trafficking and function of NPC1. Our results based on VSP yield for the first time an atomic resolution sequence-to-function-structure level of insight into the precision management of NPC1 in health and disease in the clinic.

Immunoblot analysis of patient-derived NPC1 primary fibroblasts harboring different alleles shows substantial heterogeneity in both polypeptide expression and stability compared to fibroblasts expressing the WT NPC1. NPC1 acquires up to 14 N-linked glycans during co-translational translocation into the ER. These ER-localized high mannose glycoforms are sensitive to digestion by endoglycosidase H (endo $H^S$) in cell lysates prepared by detergent solubilization. Following delivery from the ER to the Golgi, the N-linked glycans are progressively processed to endo H resistant (endo $H^R$) glycoforms by the Golgi, leading to slower migration on SDS-PAGE. When we examined the effect of endo H on folding and trafficking in primary fibroblasts, the WT NPC1 glycoform was highly resistant to endo H, indicating efficient transfer to the Golgi. In contrast, the fibroblasts expressing the P401T/I1061T and G673/I1061T alleles showed intermediate levels, whereas the most common I1061T homozygous variant fibroblast population was largely endo H sensitive. These results suggest a differential impact of each variant on the proteostasis-dependent NPC1 folding trajectory contributing degradation and/or trafficking from the ER (Wiseman et. al. 2007) and function in the LE/LY.

NPC1 is composed of multiple domains that harbor the different variants contributing to disease. Given the heterozygous allelic composition of most NPC1 primary fibroblasts that compromise interpretation of the impact of a specific allele on disease progression, we silenced NPC1 expression with shRNA to generate stable null cell lines. These null cell lines were transiently transfected with a sparse collection of plasmids that each harbor one of 48 distinct NPC1 disease-associated variants in NPC1 distributed among the various NPC1 domains. Based on the level of trafficking revealed by level of endo $H^S$ and endo $H^R$ glycoforms found for each variant, we generated an endo $H^R$/(endo $H^S$+endo $H^R$) ratio that reports on NPC1 variant ER versus post-ER distribution in the cell, referred to hereafter as the tafficking index (TrIdx). We binned this sparse collection of variants into 4 functional classes (Cass I-IV). Class I variants lack polypeptide expression in response to non-sense and/or splicing (truncation) mutations (null), Class II missense variants are largely ER retained (defined as <0.2 TrIdx), Class III missense variants show an intermediate level of trafficking (defined as 0.2 to 0.5 TrIdx) and Class IV missense variants have a level of trafficking >0.5 TrIdx indicating significant export from the ER. For example, expression of NPC1I1061T revealed that the variant was, as expected, unstable and largely sensitive to endo H digestion with a TrIdx of 0.13 (Class II), and localization to the ER, properties consistent with those found in patient fibroblasts and a mouse model of homozygous disease. The impact of cholesterol (ChoI) storage in the LE/LY for each of these variants was measured using automated high content screening image analysis based on filipin staining. The combined results revealed a gradient of cholesterol accumulation in the LE/LY compartments reflecting the differential impact of a specific variant on trafficking to and/or function in the LE/LY. Because each of the variants tested contribute to clinical disease, these results suggest that either nascent synthesis, ER stability, trafficking from the ER and/or function in LE/LY can differentially contribute to clinical presentation of disease.

Each of the 48 NPC1 variants was examined for the impact of SAHA on both TrIdx and ChoI in the LE/LY. Similar to $NPC1^{I1061T}$ fibroblasts, the majority of NPC1 variants with a TrIdx<0.2 were corrected by SAHA to at least a Class III TrIdx, while variants with >0.2 TrIdx showed a more variable impact of SAHA on TrIdx. In contrast, HDACi improved ChoI homeostasis for most of variants to a level comparable to or greater than that observed in either untreated or SAHA-treated WT-NPC1 cells. A similar result was observed for LBH589, a class I/II HDACi previously shown to correct I1061T at nM concentrations. The effects of HDACi were NPC1-dependent as restoration of ChoI homeostasis by SAHA was not observed in fibroblasts lacking NPC1 and in null cell-lines lacking NPC1. When we grouped variants by structural domains, both the luminal MLD3 and CLD5 variants showed a statistically significant correlation of TrIdx in their response to SAHA compared to all other domains, suggesting a potential central role of MLD3 and CLD5 in managing ER export. Strikingly, cholesterol homeostasis was significantly restored by either SAHA or LBH589 (Pearson's r-value 0.69 (p-value=$3\times10^{-8}$) in all domains. While ChoI homeostasis of NPC1 variants in the vehicle control showed a modest but significant correlation with TrIdx (Pearson's r-value=−0.36, p-value=0.01), SAHA completely eliminated this correlation by shifting most variants to a class Ill phenotype (Pearson's r-value=−0.07, p-value=0.64). Moreover, the correlation between the delta (Δ) of ChoI and Δ of Tridx in the absence or presence of SAHA, or the Δ of ChoI and the Δ of only the maureglycoform in response to SAHA showed low Pearson's r-values (0.18 and 0.23, respectively) and were not statistically significant. These results suggest that SAHA separately impacts the management of ER export and the function of NPC1 variants in achieving cholesterol homeostasis in the LE/LY.

To understand the complex dynamics of endomembrane trafficking pathways in response to inherited variation, and to assess the genotype to phenotype transformation responsible for NPC1 stability, cellular location and function in response to HDACi, we applied variation spatial profiling (VSP) to the 48 NPC1 variants. VSP treats variants as fiduciary markers of folding intermediate steps contributing to disease. VSP analyzes the spatial covariance (SCV) of a sparse collection of variant genotypes to one another and their functional features as input using a Gaussian process analysis to generate phenotype landscapes and sequence-to-function-to-structure relationships for the entire NPC1 polypeptide as output. VSP allows us to harness the collective insights of a sparse collection variants found distributed across the NPC1 patient population to understand the functional features of the complete polypeptide fold design at atomic resolution found in each individual presenting with disease.

To generate phenotype landscapes that allow us to discover sequence-to-function-to-structure relationships for the entire polypeptide chain at atomic resolution, the training set comprising each of the 48 variant's normalized linear position in the NPC1 polypeptide sequence (referred to as VarSeqP) was plotted as an input value on the x-axis genotype coordinate. To assess the relationship of each genotype to function, we assigned as the y-axis input the known value of each variant's ChoI measurement. Distance values defined by VarSeqP-ChoI spatial relationship provide the first layer of spatial information for the analysis and show how ChoI homeostasis is influenced by a variant's sequence position. These 2D plots illustrate the striking change that occurs in such simple spatial relationships in response to SAHA where we detect a compaction of spatial relationships reflecting a substantial decrease in the ability of most variants to disrupt cholesterol homeostasis.

To address the spatial relationship between VarSeqP-ChoI measurements and trafficking given the importance of cellular location in proper of management of cholesterol by NPC1, an input z-value was assigned the known TrIdx value for each variant. The spatial relationship of the z-axis to each VarSeqP-ChoI value provides the second layer of spatial information that can now link variant sequence position and its impact on ChoI to the TrIdx, that is, its cellular location. The spatial relationships based on both distance and spatial variance for all possible 1128 variant pairwise combinations were modeled by a molecular variogram. These results show that the spatial variance of TrIdx in the absence of SAHA increases according to the distance defined by VarSeqP-ChoI relationship, a value referred to as the 'range', until it reaches a plateau. Spatial relationships within the range are more dependent on one another (i.e., they covary with each other), while spatial relationships extending beyond the range are not correlated and of lower value in VSP in interpreting genotype to phenotype relationships. A range of 0.19 suggests that the spatial variance of the TrIdx is, surprisingly, only dependent on VarSeqP-ChoI relationship over a sequence range of ~250 amino acids, suggesting a modular design of the NPC1 polypeptide sequence that relates genotype to distinct features of the fold responsible for trafficking and function. Strikingly, SAHA significantly reduced the range to about 40 amino acids. Moreover, the spatial variance (the plateau) of the TrIdx is reduced by 40%. These results reveal for the first time that treatment with HDACi results in a significant decrease in the stringency of the known sequence relationships that contribute to the modularity and biological properties of the NPC1 polypeptide fold. Thus, the relationships defined by the molecular variogram suggests that HDACi reduces the overall rigor of the folding interactions, presumably by the altering the acetylation/deacetylation balance, that are responsible for variant loss-of-function activity in trafficking and/or cholesterol management, thereby imparting an improvement in cholesterol homeostasis.

To expand the spatial relationships modeled by the molecular variogram to all other residues spanning the NPC1 polypeptide sequence we performed molecular Kriging (MK), a Gaussian process that places weight on spatial state proximity as a critical parameter impacting polypeptide function. MK generates as an output a TrIdx-'phenotype landscape' that captures the hidden layers of information contributing to the genotype to phenotype transformation based on the sparse training input datasets for y- and z-coordinates (~1,070,000 predictions, r=0.41, p=0.003). The TrIdx-phenotype landscape quantitates both the known and the unknown (predicted) TrIdx values (z-axis) for each amino acid residue across the entire polypeptide chain as a heatmap in response to the VarSeqP-ChoI coordinates relationships, thereby linking sequence position to cellular location to function of NPC1. Confidence in relationships is defined by contour maps embedded in the landscape as a fingerprint that show the strength of all SCV relationships found in the range of the molecular variogram. For example, the TrIdx-phenotype landscape reveals diverse trafficking values where variants impacting trafficking are mainly localized in the luminal MLD3 and CLD5 domains. These variants are mainly clustered in the top 25% high confidence quartiles, indicating that these sequence regions are critical for export from the ER based on poor acquisition of endo $H^R$ glycoforms.

Strikingly, the TrIdx-phenotype landscape undergoes a general compaction in the presence of SAHA. These results reveal that the global improvement in cholesterol homeostasis in response to HDACi occurs, in part, through new SCV relationships that convert poor Class II TrIdx values to improved Class III TrIdx values. For example, SCV cluster 2 in CLD5, that has a severe defect for both TrIdx and ChoI, undergoes a coordinated shift towards WT-like ChoI function (y-axis) and a Class III TrIdx (z-axis) as highlighted in a 3D projection of the TrIdx-phenotype landscape. The response of variants in SCV cluster 1 in MLD3 that also has a severe TrIdx defect but only a modest cholesterol defect is more diverse in their response to SAHA. For example, the TrIdx and ChoI of P532L are both improved by SAHA. In contrast, the lack of significant correction of ChoI of H510P is due to the inability of SAHA to improve the its TrIdx. Moreover, the large improvement of TrIdx of R518Q does not significantly improve cholesterol homeostasis reflecting the critical role of this residue in binding of NPC2.

VSP-generated TrIdx phenotype landscapes provide the basis for an atomic resolution prediction of the function of both known (the sparse collection of input variants) and unknown (predicted output) amino acid residues that can be directly mapped onto the NPC1 structure. Directly mapping function to structure reveals for the first time the contribution of all the NPC1 residues to trafficking and cholesterol homeostasis with a prediction confidence, which we refer to as the TrIdx functional-adaptive structure (FAST) state. The TrIdx-FAST state clearly reveals the molecular handshake between MLD3 and CLD5 as a central feature determines the ER export of NPC1. Strikingly, atomic resolution mapping of the impact of SAHA on the TrIdx phenotype landscape reveals a significant improvement in cholesterol homeostasis for nearly all residues by shifting the Class II TrIdx to that of Class III indicative of significant export from the ER. Thus, the SCV relationships predicted from the collective of fiduciary NPC1 variants found in the patient population using VSP teach us for the first time the core structural features that define normal NPC1 trafficking.

To assign a value to cholesterol homeostasis based on the TrIdx response to NPC1 variants, we flipped the biological features used for y-axis and z-axis. The molecular variogram modeling of these relationships in the absence of SAHA shows that the spatial variance of ChoI increases according to the distance defined by the VarSeqP-TrIdx spatial relationship, revealing a range ~0.08. A range of ~0.08 suggests that the spatial variance of cholesterol homeostasis is, surprisingly, dependent on VarSeqP-TrIdx relationship over a shorter sequence range of ~100 amino acids when compared to the larger range observed in the TrIdx molecular variogram (~240 amino acids). These results suggest a more limited dependence of function between NPC1 sequence modules once achieving LE/LY localization, supporting the hierarchical relationships between ER and LE/LY compartments. Strikingly, SAHA decreases the range from 0.08 to 0.02 and significantly reduces the spatial variance of the ChoI value by nearly 70%. These results raise the possibility that SAHA largely eliminates the functional diversity imparted by inherited NPC1 variants affecting ChoI homeostasis in the clinic. By reducing the inter-dependency of sequence modules that leads to disease phenotype in untreated cells, SAHA resolves the problem imposed by variant disrupted folding intermediates.

We next performed MK to generate an output ChoI-phenotypelandscape that predicts cholesterol responses across the entire polypeptide sequence in the context of all VarSeqP-TrIdx spatial relationships (~1,400,000 predictions). Interestingly, the ChoI-phenotype landscape in the absence of SAHA reveals two SCV clusters in the top 25% confidence quartile that show Class III TrIdx yet have severe cholesterol homeostasis defects. One cluster is found in STMD4 (cluster 3) and the other spanning CLD5 and CTMD6 (cluster 4). These spatial relationships suggest that clusters 3 and 4 are critical in mediating cholesterol management in the LE/LY. Indeed, P691 in SCV cluster 3 has been shown to be involved in cholesterol binding. Thus, the ChoI-phenotype landscape now reveals that CLD5, CTMD6 and STMD4 contribute together to tuning cholesterol flow.

The ChoI-phenotype landscape undergoes a striking change in the presence of SAHA highlighting the ability of SAHA to improve cholesterol homeostasis for most of variants. Moreover, the predicted confidence contour intervals in the molecular variogram range decrease substantially indicating a substantial loss of spatial interdependency of variant residues triggering disease. The dramatic correction of cholesterol homeostasis (z-axis) of variants found in SCV clusters 3 and 4 even in the absence of improvement of their TrIdx (y-axis) indicates that SAHA can also adjust the function of NPC1 in the LE/LY to improve cholesterol management.

By projecting ChoI-phenotype landscape at atomic resolution, the ChoI-FAST can now be used to map the potential path of cholesterol flow in NPC1. Based on class 111 variants that are primarily defective in cholesterol homeostasis, ChoI-FAST reveals the critical residues for cholesterol export that include SCV cluster 4 residues in CLD5 and CTMD6, as well as SCV cluster 3 residues in STMD4, the later recently proposed to form a second cholesterol binding site. Moreover, the proline-rich liner between SNLD1 and the TM region that has been suggested to facilitate cholesterol transfer is now shown by spatial state analysis to have little impact on trafficking yet contribute directly to the flow path. All residues on the flow path are highly responsive to SAHA. The potential cholesterol flow path is highlighted in the TM region. R1077Q in CLD5, Y1088C and W1145R at the beginning of TM9 and TM11 are possibly disrupting the flow of cholesterol from CLD5 domain to TM region. Y634C in TM3, P691S in TM5 and L1191F in TM12 are possibly crucial for cholesterol binding and export. The cholesterol storage state of those variants along the flow path is improved to level of WT or even better than WT. These results for the first time assign a potential role for linked activities of CLD5 and CTMD6 in the cholesterol export function of NPC1 and illustrate the ability of HDACi to increase the flexibility (i.e., decrease the SCV dependence) of these regions to restore cholesterol homeostasis in LE/LY.

Given the differences in the TrIdx-FAST and ChoI-FAST states of NPC1 in both basal and HDACi conditions, we can generate FAST states reflecting their delta (11) values. The 11 TrIdx-FAST highlights that the trafficking properties conferred by MLD3 and CLD5 residues are largely corrected by SAHA. In contrast, SNLD1 is largely resistant to SAHA except for the N-terminal a-helix containing C63R variant. This a-helix has been previously shown to interact with CLD5, suggesting that the a-helix could play an important role in managing the stringency of ER-export via the CLD5-MLD3 handshake. The TM region is also largely resistant to SAHA, for example, the trafficking of the variants involved in the predicted path of cholesterol flow are not changed by SAHA.

In contrast the to the 11TrIdx-FAST, the 11 ChoI-FAST highlights residues involved in the global response of NPC1 to SAHA, particularly residues involved in the predicted path of cholesterol flow. The dramatic improvement of cholesterol homeostasis for TM3-4 in STMD4 and TM9-13 in CTMD6 is achieved without significant improvement of TrIdx, indicating that the dynamics of these TM helices in the LE/LY in response to SAHA contributes to the export of cholesterol. These results explain the many uncorrelated relationships between ER-associated folding/export system managing the intrinsic stability of the NPC1 fold for trafficking to post-ER compartments and the activity of NPC1 in the LE/LY facilitating cholesterol flow, suggesting that each endomembrane compartment is optimized for unique spatial state dependent functions.

To understand the spatial relationships defined by our bench-based experimental measurements to those observed in the clinic, we correlated the TrIdx phenotype landscapes based on acquisition of endo H resistance with the natural history of 27 NPC1 patients that overlap with the input variant dataset. While there is no significant correlation between trafficking and severity of disease presentation by all NPC1 patients, we found that Class III allele containing patients have a significant correlation with a late age of neurological onset when compared with all other patients that lack class Ill variants. These results are consistent with the observation that this spatial state relationship is not observed when we enrich for patients belonging to either Class II or Class IV variant alleles.

To map SCV relationships for residues spanning the entire NPC1 polypeptide chain to age of neurological onset (ANO), we used TrIdx as the y-axis coordinate to predict the phenotype landscape for the age of neurological onset (z-axis) (r=0.49, p=0.03). Strikingly, we found in the ANO-phenotype landscape a prominent SCV cluster in CLD5 with Class III TrIdx properties that shows a significant late ANO, likely due to their ability maintain a higher ratio of post-ER functional protein. The known variants that contributed to this predicted age-dependent SCV cluster (V950M, S954L, P1007A and T1036M) are highly responsive to SAHA treatment illustrating how VSP can be used to predict strong candidates for clinical trials (~70% percentile). Moreover, because SAHA also improves nearly all Class II CLD5 variants to a class Ill phenotype with the resultant improvement in cholesterol management, VSP predicts that improving even Class II CLD5 variants (e.g., I1061T) to a Class III trafficking through an early interventional strategy may significantly increase the age of onset and reduce the impact of disease in these early onset patients.

VSP captures sequence-to-function-to-structure relationships across the entire polypeptide chain using a sparse collection of evolutionary tuned fiduciary markers of polypeptide folding intermediates found in the population. It enables a comprehensive description of structure snapshots generated by in vitro methods, establishing that variants distributed in the population through natural selection can unlock an unanticipated view of the dynamics and modularity of the protein fold required to generate biological function and predict an individual's response to disease when information is lacking. For example, VSP revealed that CLD5 is a pivotal module in NPC1 where it forms a biological handshake with MLD3 to direct trafficking from the ER, a result analogous to the role of the NBD1-TMD2 interaction in the cystic fibrosis transmembrane conductance regulator (CFTR) that directs trafficking from the ER (Wang and Balch, 2017). VSP predicts the CLD5-MLD3 handshake organizes select clusters of residues in the transmembrane spanning STMD4-CTM6 modules that serve as a conduit to complete transfer of cholesterol from SNLD1 through the LE/LY bilayer, charting for the first time a path forward to understand more globally the biological dynamics of the protein fold in living organisms based on the genotype to phenotype transformation.

VSP reveals that many variants contributing to NPC1 disease have little impact on ER export, for example, the variants involved in the predicted path of cholesterol transfer that is critical for function. Moreover, we found that there are largely differential responses to HDACi treatment between the ER-export system and cholesterol management at LE/LY. Therefore, our analysis of SCV relationships suggests that the ER does not function on the basis of a quality control (QC) or a 'triage' metric that should, in principle, restrict export of all non-functional sequences and/or increase the export of corrected functional sequences. This conclusion is similar to that reached for CFTR where >40% of variants trafficking to the cell surface lack normal function. Here, we posit that the ER serves as a 'spatial state maturation' (SPAM) detector that only captures aberrant folding events based on yet to be determined physics-based spatial energetics SCV principles, rules that likely dictate an overall folding 'set-point' in a given cytosolic, endomembrane compartment and/or cell-type. As a SPAM manager, the ER provides unanticipated flexibility in generating downstream FAST states that routinely encounter diverse developmental and environmental challenges that generate and/or maintain biology. Our results are consistent with negligible impact of most other polypeptide variants traversing the exocytic pathway that contribute to human disease including Alzheimer's precursor protein (APP), low density lipoprotein receptor (LDL-R), G-protein coupled receptors (GPCRs), epidermal growth factor receptor (EGFR) and the abundant secreted soluble proteins including alpha-1-antirypsin (AAT) whose FAST states, like NPC1, are necessarily only realized in biochemically distinct downstream compartments such as the extreme acid pH of the LE/LY.

VSP provides substantial insight into the role of HDAC biology in health and disease. We demonstrated quantitatively that HDACi can globally alter the NPC1 polypeptide functional response by shortening the range and decreasing the spatial variance (the plateau) seen in the molecular variogram. In so doing, it is apparent that HDACi relaxes the stringency of the functional fold negatively perturbed by variation. This is in direct contrast to the impact of Ivacaftor-for a select group CFTR variants (Wang and Balch, 2017) where Ivacaftor functions as an 'SCV agonist' by not affecting the range, rather by increasing the plateau in the variogram, promoting robust chloride conductance in an privileged open state conformation. The new set of SCV relationships imposed on NPC1 by the modified HDAC environment in response to HDACi not only improves export to the Golgi and trafficking to the LE/LY, but NPC1 function in management of cholesterol homeostasis. Mechanistically, whether these HDACi sensitive events directly alter the acetylation pattern of the NPC1 polypeptide chain, and/or more indirectly, through transcriptional and/or post-translational mechanisms affecting HDAC sensitive proteostasis pathways, or even HDAC sensitive events facilitating endomembrane (ER-Golgi-LE/LY) compartment function, remains to be determined. The impact of HDACi on diverse features of NPC1 variant function could be similar to its effect on histone-based nucleosome assembly/disassembly pathways that necessarily balance diverse transcriptional programs contributing to development and responses to the environment.

By revealing links between the known and unknown through SCV relationships that can be mapped at atomic resolution to protein structure snapshots to capture the inherent dynamics and biology of the fold, VSP provides us with a fresh computational approach that could serve as a quantitative language base captured in genotype-based phenotype landscapes to begin to directly interpret the genotype to phenotype transformation evolved through natural selection. While we used structure for validation, it is evident that a complete understanding of high-resolution predictive phenotype landscapes should allow us to assess the genotype to phenotype transformation in the absence of structure. Routine implementation of an SCV-based approach using a sparse collection of variants for any protein from pharmacological and/or clinical perspectives could help to explain not only the general dynamic features of the protein fold responsible for human health and disease through analyses of FAST states as shown herein, but help us to calibrate ongoing efforts for clinical management disease from a precision medicine perspective. By defining the overall topology of the phenotype landscapes to a given therapeutic using a sparse collection of variants, VSP provides us with a paradigm that fully embraces the central role of a genome-based knowledge platform being acquired through whole genome sequencing of the population to, for the first time, provide precision benefit to the individual based on the same rules evolution has evolved to promote survival and fitness.

As described above, Variant Spatial Profiling (VSP) is a novel tool to read the genome to define the genotype to phenotype transformation responsible for biological sequence to function to structure relationships. Natural/disease variants may be used as fiduciary markers of evolved protein folding pathways that as a collective provide a means to read the genomic sequence to assign function of the encoded protein. Spatial covariance (SCV) relationships are useful to analyze genotype to phenotype, phenotype to genotype or phenotype to phenotype relationships. A phenotype landscape links variant position in primary sequence (x-axis) to phenotypes (y- and z-axis). It is possible to flip or change phenotypes on y- and z-axis or assigning x-axis as phenotype to use VSP from different perspectives for prediction of function. Confidence contours can be used to define the value of the fingerprint in phenotype landscape in the context of sequence to function to structure relationships. Sequence or functional modules (SCV clusters) can be revealed by fingerprint and predicted z-value. VSP can be used to predict 3D structural information of protein fold. The phenotype landscape can be mapped onto structure to explain the static structure in the context of function. Interpretation and prediction of therapeutic response can be performed by VSP. VSP can make prediction of phenotype or therapeutic response reflecting unique physiological condition of individual patient even for patients with the same genotype or the same patient at different age or environmental conditions. VSP is a platform to integrate, assess and predict the cell/animal-based measurements and clinical features of patients, and inter-relate these measurements to provide guidance for model relevance and development. VSP can be used to guide precision medicine and provide a platform for FDA approval of therapeutic intervention based on sequence to function to structure derived from human sequencing efforts. It may be a global mechanism to ascertain genotype to phenotype transformation for all non-human organisms and to define the evolved state of the fold for improved, targeted function in product development relevant broadly to understanding health and addressing disease.

As demonstrated above, the VSP strategy can be used to analyze and predict the genotype to phenotype transformation for any gene. The range and spatial variance relationships within and between sequences modules based on VSP strategy reveal the 3D functional structure information of polypeptide fold. VSP strategy can be used to predict the drug response and clinical features for patients with diverse and complex genetic or environmental backgrounds. It provides a universal platform to integrate and assess the data coming from variety sources, such as cell-based or animal-based models, and all the various clinical features from patients all over the world. It provides a novel proprietary platform for application of precision medicine.

The systems and methods described above may be operational with numerous general-purpose or special-purpose computing system environments, configurations, processors and/or microprocessors. Examples of well-known computing systems, environments, and/or configurations that may be suitable for use with the technology disclosed herein include, but are not limited to, personal computers, server computers, hand-held or laptop devices, multiprocessor systems, microprocessor-based systems, programmable consumer electronics, network PCs, minicomputers, mainframe computers, distributed computing environments that include any of the above systems or devices, and the like.

A microprocessor may be any conventional general-purpose single- or multi-chip microprocessor. In addition, the microprocessor may be any conventional special purpose microprocessor such as a digital signal processor or a graphics processor. The microprocessor typically has conventional address lines, conventional data lines, and one or more conventional control lines.

The system described above may comprises various modules and/or components. Since functionality of one module may be performed along with or by one or more other modules, the description of each of the modules is used for convenience to describe the functionality of the preferred system. Thus, the processes that are undergone by each of the modules may be arbitrarily redistributed to one of the other modules, combined together in a single module, or made available in, for example, a shareable dynamic link library.

Instructions or code utilized by or for the system may be written in any programming language such as but not limited to C, C++, BASIC, Pascal, or Java.

In one or more example embodiments, the functions and methods described may be implemented in hardware, software, or firmware executed on a processor, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

Further, it should be appreciated that modules and/or other appropriate means for performing the methods and techniques described herein can be downloaded and/or otherwise obtained by a user device/terminal and/or base station as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a user terminal and/or base station can obtain the various methods upon coupling or providing the storage means to the device. Moreover, any other suitable technique for providing the methods and techniques described herein to a device can be utilized.

General Interpretive Principles for the Present Disclosure

Various aspects of the novel systems, apparatuses, and methods are described more fully hereinafter with reference to the accompanying drawings. The teachings disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the novel systems, apparatuses, and methods disclosed herein, whether implemented independently of or combined with any other aspect of the disclosure. For example, a system or an apparatus may be implemented, or a method may be practiced using any one or more of the aspects set forth herein. In addition, the scope of the disclosure is intended to cover such a system, apparatus or method which is practiced using other structure, functionality, or structure and functionality in addition to or other than the various aspects of the disclosure set forth herein. It should be understood that any aspect disclosed herein may be set forth in one or more elements of a claim. Although some benefits and advantages of the preferred aspects are mentioned, the scope of the disclosure is not intended to be limited to particular benefits, uses, or objectives. The detailed description and drawings are merely illustrative of the disclosure rather than limiting, the scope of the disclosure being defined by the appended claims and equivalents thereof.

With respect to the use of plural vs. singular terms herein, those having skill in the art can translate from the plural to the singular and/or from the singular to the plural as is appropriate to the context and/or application. The various singular/plural permutations may be expressly set forth herein for sake of clarity.

When describing an absolute value of a characteristic or property of a thing or act described herein, the terms "substantial," "substantially," "essentially," "approximately," and/or other terms or phrases of degree may be used without the specific recitation of a numerical range. When applied to a characteristic or property of a thing or act described herein, these terms refer to a range of the characteristic or property that is consistent with providing a desired function associated with that characteristic or property.

In those cases where a single numerical value is given for a characteristic or property, it is intended to be interpreted as at least covering deviations of that value within one significant digit of the numerical value given.

If a numerical value or range of numerical values is provided to define a characteristic or property of a thing or act described herein, whether or not the value or range is qualified with a term of degree, a specific method of measuring the characteristic or property may be defined herein as well. In the event no specific method of measuring the characteristic or property is defined herein, and there are different generally accepted methods of measurement for the characteristic or property, then the measurement method should be interpreted as the method of measurement that would most likely be adopted by one of ordinary skill in the art given the description and context of the characteristic or property. In the further event there is more than one method of measurement that is equally likely to be adopted by one of ordinary skill in the art to measure the characteristic or property, the value or range of values should be interpreted as being met regardless of which method of measurement is chosen.

It will be understood by those within the art that terms used herein, and especially in the appended claims (e.g., bodies of the appended claims) are intended as "open" terms unless specifically indicated otherwise (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

In those instances where a convention analogous to "at least one of A, B, and C" is used, such a construction would include systems that have A alone, B alone, C alone, A and B together without C, A and C together without B, B and C together without A, as well as A, B, and C together. It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include A without B, B without A, as well as A and B together."

Various modifications to the implementations described in this disclosure can be readily apparent to those skilled in the art, and generic principles defined herein can be applied to other implementations without departing from the spirit or scope of this disclosure. Thus, the disclosure is not intended to be limited to the implementations shown herein but is to be accorded the widest scope consistent with the claims, the principles and the novel features disclosed herein. The word "exemplary" is used exclusively herein to mean "serving as an example, instance, or illustration." Any implementation described herein as "exemplary" is not necessarily to be construed as preferred or advantageous over other implementations.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

What is claimed is:

1. A method of estimating a biological or chemical property of one or more molecule variants, wherein the molecule variants are characterized by different molecular features, the method comprising:

receiving or computing a first plurality of position values for a first plurality of molecular features;

receiving or computing a first plurality of severity values for a first phenotypic property exhibited by a cell or animal or patient harboring the molecule when the molecule contains each of the first plurality of molecular features;

receiving or computing a first plurality of severity values for a second phenotypic property different from the first phenotypic property exhibited by a cell or animal or patient harboring the molecule when the molecule contains each of the first plurality of molecular features;

computing a first plurality of two-dimensional coordinates, one for each of the first plurality of molecular features using the first plurality of position values of the first plurality of molecular features on a first coordinate axis and the first plurality of severity values of the first phenotypic property corresponding to each of the first plurality of molecular features on a second coordinate axis;

computing a distance in the plane defined by the first coordinate axis and the second coordinate axis between each different pair of the first plurality of computed two dimensional coordinates;

computing at least one relationship between the variance of the first plurality of severity values of the second phenotypic property and distance in the plane defined by the first coordinate axis and the second coordinate axis using sets of the computed distances that fall within defined distance ranges;

computing a second plurality of severity values for the second phenotypic property for a second plurality of two dimensional coordinates in the plane defined by the first coordinate axis and the second coordinate axis that are not among the first plurality of two dimensional coordinates of the first plurality of molecular features, wherein the computing of a severity value for the second phenotypic property for each given one of the second plurality of two dimensional coordinates is based at least in part on (1) the distance between the given one of the second plurality of two dimensional coordinates and each of the first plurality of two dimensional coordinates corresponding to the first plurality of molecular features, and (2) the severity value for the second phenotypic property at each of the first plurality of two dimensional coordinates corresponding to the first plurality of molecular features; and generating a three-dimensional visualization of the computed severity values for the second phenotypic property at the second plurality of two-dimensional coordinates.

2. The method of claim 1, wherein the molecules are proteins, and the different molecular features are different amino acid sequence variants.

3. The method of claim 1, wherein the molecules are nucleic acids, and the different molecular features are different nucleotide sequence variants.

4. The method of claim 1, wherein the three-dimensional visualization associates different displayed colors with different severity levels for the second property.

5. The method of claim 1, additionally comprising computing confidence intervals for the estimated severity levels of the second property.

6. The method of claim 1, wherein the severity levels for the first property are normalized with respect to wild-type severity for the first property.

7. The method of claim 2, wherein the position values are normalized with respect to the length of the protein.

8. The method of claim 1, wherein the first phenotypic property is a first cellular level function associated with cells harboring molecules having each of the first plurality of molecular features.

9. The method of claim 8, wherein the second property is a second, different cellular level function associated with cells harboring molecules having each of the first plurality of molecular features.

10. The method of claim 8, wherein the second property is an organism level clinical property associated with an organism having cells harboring molecules having each of the first plurality of molecular features.

\* \* \* \* \*